(12) United States Patent
Howland et al.

(10) Patent No.: US 11,712,456 B2
(45) Date of Patent: Aug. 1, 2023

(54) HEMP EXTRACT FOR TREATMENT OF PAIN IN ANIMALS

(71) Applicant: Portland Technology Holdings LLC, South Portland, ME (US)

(72) Inventors: Amanda Howland, South Portland, ME (US); Christian Kjaer, South Portland, ME (US)

(73) Assignee: PORTLAND TECHNOLOGY HOLDINGS LLC, South Portland, ME (US)

(*) Notice: Subject to any disclaimer, the term of this patent is extended or adjusted under 35 U.S.C. 154(b) by 0 days.

(21) Appl. No.: 17/684,154

(22) Filed: Mar. 1, 2022

(65) Prior Publication Data

US 2022/0211790 A1 Jul. 7, 2022

Related U.S. Application Data

(63) Continuation of application No. 17/045,945, filed as application No. PCT/US2019/026631 on Apr. 9, 2019.

(60) Provisional application No. 62/655,170, filed on Apr. 9, 2018.

(51) Int. Cl.
| | |
|---|---|
| *A61K 36/185* | (2006.01) |
| *A61P 29/00* | (2006.01) |
| *A61K 31/01* | (2006.01) |
| *A61K 31/015* | (2006.01) |
| *A61K 31/045* | (2006.01) |
| *A61K 31/05* | (2006.01) |
| *A61K 31/192* | (2006.01) |
| *A61K 31/352* | (2006.01) |
| *A61K 31/353* | (2006.01) |
| *A61K 47/44* | (2017.01) |
| *A23K 50/40* | (2016.01) |
| *A61K 9/00* | (2006.01) |

(52) U.S. Cl.
CPC ............ *A61K 36/185* (2013.01); *A23K 50/40* (2016.05); *A61K 9/0056* (2013.01); *A61K 31/01* (2013.01); *A61K 31/015* (2013.01); *A61K 31/045* (2013.01); *A61K 31/05* (2013.01); *A61K 31/192* (2013.01); *A61K 31/352* (2013.01); *A61K 31/353* (2013.01); *A61K 47/44* (2013.01); *A61P 29/00* (2018.01)

(58) Field of Classification Search
CPC ................................................ A61K 31/352
See application file for complete search history.

(56) References Cited

U.S. PATENT DOCUMENTS

| | | | |
|---|---|---|---|
| 8,895,078 B2 | 11/2014 | Mueller | |
| 9,955,716 B1 | 5/2018 | Nordahl | |
| 10,272,051 B2 | 4/2019 | Changoer et al. | |
| 10,597,348 B1 | 3/2020 | Nordahl | |
| 10,918,686 B2 * | 2/2021 | Siurkus | A61K 47/00 |
| 10,940,173 B2 | 3/2021 | Finley et al. | |
| 2005/0165088 A1 | 7/2005 | Whittle et al. | |
| 2005/0266108 A1 | 12/2005 | Flockhart et al. | |
| 2010/0168448 A1 | 7/2010 | Flockhart et al. | |
| 2010/0249223 A1 | 9/2010 | Di Marzo et al. | |
| 2010/0292345 A1 | 11/2010 | Pertwee | |
| 2013/0059018 A1 | 3/2013 | Parolaro et al. | |
| 2013/0209483 A1 | 8/2013 | McAllister | |
| 2014/0039043 A1 | 2/2014 | Musty et al. | |
| 2014/0221469 A1 | 8/2014 | Ross et al. | |
| 2015/0057342 A1 | 2/2015 | Koren et al. | |
| 2016/0000843 A1 | 1/2016 | Lowe et al. | |
| 2016/0053220 A1 | 2/2016 | Peet et al. | |
| 2016/0106705 A1 | 4/2016 | Verzura et al. | |
| 2016/0228385 A1 | 8/2016 | Sievers et al. | |
| 2016/0296464 A1 | 10/2016 | Lindsay | |
| 2016/0346339 A1 | 12/2016 | Finley et al. | |
| 2017/0143642 A1 | 5/2017 | Stott et al. | |
| 2017/0172977 A1 | 6/2017 | Kleidon et al. | |
| 2017/0290870 A1 | 10/2017 | Schaneville | |
| 2017/0348306 A1 | 12/2017 | Creasy et al. | |
| 2018/0104214 A1 | 4/2018 | Raichman | |
| 2018/0116998 A1 | 5/2018 | Sinai et al. | |
| 2018/0228751 A1 | 8/2018 | Stott et al. | |
| 2018/0258439 A1 | 9/2018 | Boudko et al. | |
| 2018/0263952 A1 | 9/2018 | Biro et al. | |
| 2018/0338930 A1 | 11/2018 | Small-Howard et al. | |
| 2018/0353461 A1 | 12/2018 | Perez Simon et al. | |
| 2019/0077782 A1 | 3/2019 | Raber et al. | |
| 2019/0091144 A1 | 3/2019 | McGarrah et al. | |
| 2019/0117619 A1 | 4/2019 | Guy et al. | |
| 2019/0133966 A1 | 5/2019 | Koren | |
| 2019/0167749 A1 | 6/2019 | Siurkus | |
| 2019/0201372 A1 | 7/2019 | McKay | |

(Continued)

FOREIGN PATENT DOCUMENTS

| | | |
|---|---|---|
| EP | 2044935 A1 | 4/2009 |
| EP | 2995302 A1 | 3/2016 |

(Continued)

OTHER PUBLICATIONS

Citti et al. Journal of Pharmaceutical and Biomedical Analysis, 2018, 149, p. 532-540 (Year: 2018).*
Kitryte et al. Food Chemistry, 2018, 267, pp. 420-429 (Year: 2018).*
Ibrahim et al. Planta Med., 2018; 84: 250-259 (Year: 2018).*
MacLean et. al., "Skyline: an open source document editor for creating and analyzing targeted proteomics experiments," Bioinformatics. 2010;26(7):966-8.

(Continued)

*Primary Examiner* — James D. Anderson
(74) *Attorney, Agent, or Firm* — Dechert LLP

(57) ABSTRACT

The present disclosure relates to methods of treating pain in veterinary subjects using pharmaceutical compositions and dosage forms comprising hemp extract.

24 Claims, 9 Drawing Sheets

(56) References Cited

U.S. PATENT DOCUMENTS

| | | |
|---|---|---|
| 2019/0297821 A1 | 10/2019 | Crawford et al. |
| 2019/0298683 A1 | 10/2019 | Friedman |
| 2020/0009109 A1 | 1/2020 | Macaluso et al. |
| 2020/0015440 A1 | 1/2020 | Crawford et al. |
| 2020/0015441 A1 | 1/2020 | Crawford et al. |
| 2020/0038305 A1 | 2/2020 | Garrison et al. |
| 2020/0039908 A1 | 2/2020 | ElSohly et al. |
| 2020/0093785 A1 | 3/2020 | Stauff |
| 2020/0123125 A1 | 4/2020 | Mayo et al. |
| 2020/0163900 A1 | 5/2020 | Hossain et al. |
| 2020/0253919 A1 | 8/2020 | Raz et al. |
| 2020/0262806 A1 | 8/2020 | Webb et al. |
| 2020/0270623 A1 | 8/2020 | Pauli et al. |
| 2020/0282062 A1 | 9/2020 | Naheed |
| 2020/0288659 A1 | 9/2020 | Crawford et al. |
| 2020/0405685 A1 | 12/2020 | Lewis et al. |
| 2021/0000791 A1 | 1/2021 | Levy |
| 2021/0023316 A1 | 1/2021 | Schorr et al. |
| 2021/0205236 A1 | 7/2021 | Garabagi et al. |
| 2021/0220323 A1 | 7/2021 | Levy et al. |

FOREIGN PATENT DOCUMENTS

| | | | |
|---|---|---|---|
| EP | 2146731 B1 | 1/2019 | |
| EP | 3449914 A1 | 3/2019 | |
| EP | 3449916 A1 | 3/2019 | |
| EP | 3010498 B1 | 3/2020 | |
| EP | 3258942 B1 | 1/2021 | |
| EP | 3160455 B1 | 5/2021 | |
| WO | WO-2005072719 A1 | 8/2005 | |
| WO | WO-2012144892 A1 | 10/2012 | |
| WO | 2015068052 A2 | 5/2015 | |
| WO | 2016141056 A1 | 9/2016 | |
| WO | WO-2017025712 A1 | 2/2017 | |
| WO | WO-2017091764 A1 * | 6/2017 | ............ A61K 31/05 |
| WO | WO-2017178937 A1 * | 10/2017 | ........... A61K 31/192 |
| WO | WO-2018023166 A1 * | 2/2018 | ............ A61K 31/01 |
| WO | 2018061007 A1 | 4/2018 | |
| WO | PCT/US2019/026631 | 4/2018 | |
| WO | WO-2018130682 A1 * | 7/2018 | ........... A61K 31/352 |
| WO | WO-2018175259 A1 * | 9/2018 | ............ A23K 10/00 |
| WO | WO-2018217803 A2 | 11/2018 | |
| WO | WO-2019021191 A1 | 1/2019 | |
| WO | WO-2019043259 A1 | 3/2019 | |
| WO | WO-2019071302 A1 | 4/2019 | |
| WO | 2019104442 A1 | 6/2019 | |
| WO | WO-2019159176 A1 | 8/2019 | |
| WO | WO-2019195752 A1 | 10/2019 | |
| WO | WO-2019210401 A1 | 11/2019 | |
| WO | WO-2019227167 A1 | 12/2019 | |
| WO | WO-2020016875 A1 | 1/2020 | |
| WO | WO-2020044118 A1 | 3/2020 | |
| WO | WO-2020051284 A1 | 3/2020 | |
| WO | WO-2020084427 A1 | 4/2020 | |
| WO | WO-2020121312 A1 | 6/2020 | |
| WO | WO-2020123383 A1 | 6/2020 | |
| WO | WO-2020171713 A1 | 8/2020 | |

OTHER PUBLICATIONS

PCT International Search Report from PCT/US2019/026631 dated Aug. 2, 2019.

Sulak et. al., "The current status of artisanal cannabis for the treatment of epilepsy in the United States," Epilepsy Behav. 2017;70(Pt B):328-333.

Wu et. al., "Receptor-mediated in vitro gene transformation by a soluble DNA carrier system," J. Biol. Chem. 1987;262(10):4429-4432.

U.S. Appl. No. 17/045,945, filed Apr. 9, 2019, Amanda Howland.

Bouquié et. al., "Cannabis and anticancer drugs: societal usage and expected pharmacological interactions—a review," Fund Clin Pharm. 2018;32(5):462-484.

Broccardo et. al. "Multiplexed analysis of steroid hormones in human serum using novel microflow tile technology and LC-MS/MS," J Chromatogr B Analyt Technol Biomed Life Sci. 2013;934:16-21.

Giuffrida et. al., "Development and psychometric testing of the Canine Owner-Reported Quality of Life questionnaire, an instrument designed to measure quality of life in dogs with cancer," J Am Vet Med Assoc. 2018;252(9):1073-83.

Iliopoulou et. al., "Development of a survey instrument to assess health-related quality of life in small animal cancer patients treated with chemotherapy," J Am Vet Med Assoc. 2013;242(12):1679-87.

Mason et. al., "Gastrointestinal toxicity after vincristine or cyclophosphamide administered with or without maropitant in dogs: a prospective randomised controlled study," J Small Anim Pract. 2014;55(8):391-8.

"Nerolidol 2," 2018, retrieved Nov. 2, 2020 from https://web.archive.org/web/20181019021317/htps://www.restek.com/compound/view/142-50-7/Nerolidol2.

Schrivastava, "Methods for the detemination of limit of detection and limit of quanitation of the analytical methods," Chron Young Sci. 2011;2:21-5.

Tomiyasu et. al., "Gastrointestinal and hematologic adverse events after administration of vincristine, cyclophosphamide, and doxorubicin in dogs with lymphoma that underwent a combination multidrug chemotherapy protocol," J Vet Med Sci. 2010;72(11):1391-7.

Whittenburg et. al., "Development of a limited-sampling model for predication of doxorubicin exposure iin dogs," Vet Comp Oncol. 2014;12(2):114-119.

Manallack et. al. "The Significance of Acid/Base Properties in Drug Discovery," Chem. Soc Rev. 2013;42(2):485-496.

Nadel et. al., "Tetrahydrocannabinolic acid is a potent PPARg agonist with neuroprotective activity,"Br. J. Pharmacol. 2017:174(23):4263-4276.

Perola, "An Analysis of the Binding Efficiencies of Drugs and Their Leads in Successful Drug Discovery Programs," J. Med. Chem. 2010;53(7):2986-2997.

Rock and Parker, "Effect of low doses of cannabidiolic acid and ondansetron on LiCl-induced conditioned gaping (a model of nausea-induced behaviour) in rats," Br. J. Pharmacol. 2013:169(3):685-692.

* cited by examiner

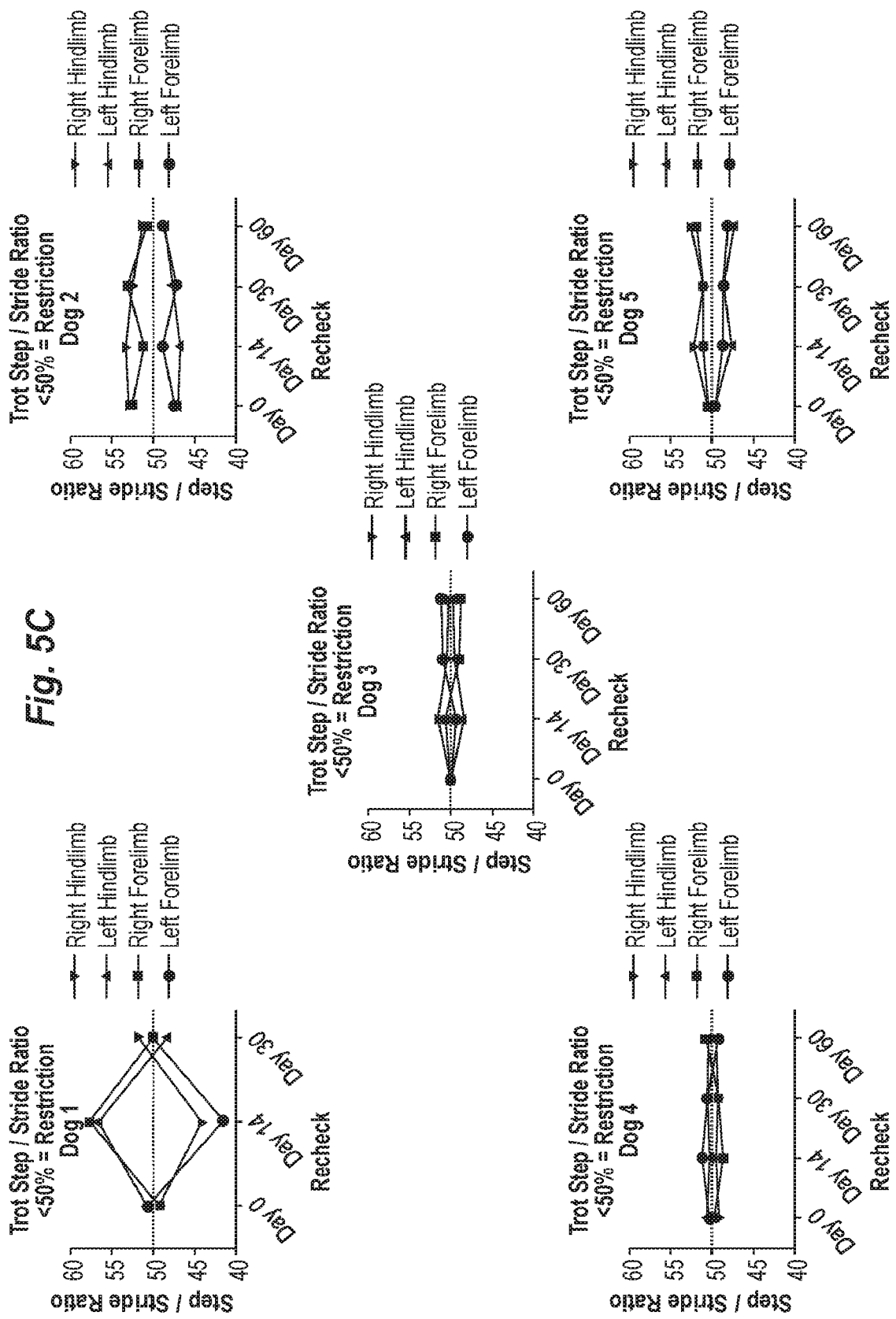

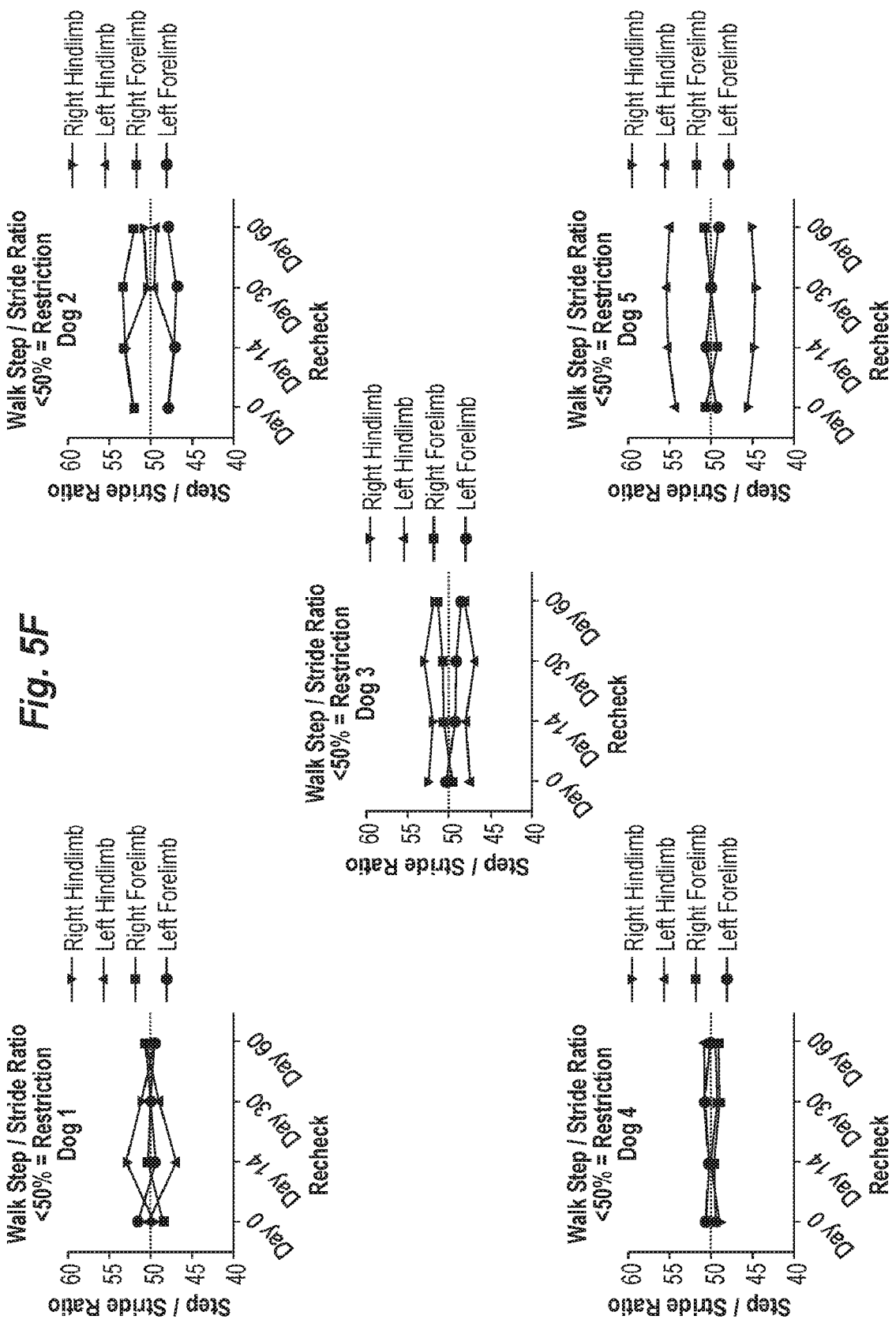

HEMP EXTRACT FOR TREATMENT OF PAIN IN ANIMALS

CROSS-REFERENCE TO RELATED APPLICATIONS

This application is a continuation of U.S. patent application Ser. No. 17/045,945, filed on Oct. 7, 2020, which is a 35 U.S.C. § 371 filing of International Patent Application No. PCT/US2019/026631, filed Apr. 9, 2019, which claims the benefit of U.S. Provisional Application No. 62/655,170, filed on Apr. 9, 2018, each of which is hereby incorporated by reference herein in its entirety.

BACKGROUND

Routine nonsteroidal anti-inflammatory drug (NSAID) treatments, though efficacious, may not provide adequate relief of pain due to osteoarthritis (OA) and might have potential side effects that preclude its use, particularly in patients with certain comorbidities. In a systematic review of 35 canine models of OA and 29 clinical trials in dogs, treatment with NSAIDs caused adverse effects in 35 of the 64 (55%) studies, most common being gastro-intestinal signs. Although other pharmacological agents are advocated, there is little evidence regarding their efficacy in dogs with chronic or neuropathic pain related to OA. In the absence of an optimal treatment for these dogs, other potentially efficacious pharmacological agents, including cannabinoids, are often sought.

SUMMARY

The present disclosure is directed toward compositions comprising cannabidiol and their use for the treatment of pain in animals. In an aspect, provided herein is a pharmaceutical composition comprising hemp extract and a carrier, wherein the hemp extract comprises:
  cannabidiol;
  cannabidiolic acid;
  cannabigerolic acid;
  Δ9-tetrahydrocannabinol; and
  cannabichromene;
  wherein the ratio of cannabidiol to cannabidiolic acid is about 0.6:1 to about 1:0.6.

In an embodiment, the hemp extract further comprises four or more of the following:
  α-pinene;
  β-myrcene;
  β-pinene;
  δ-limonene;
  linalool;
  β-caryophyllene;
  α-humulene;
  nerolidol 2;
  guaiol;
  caryophyllene oxide; and
  α-bisabolol.

In an embodiment, the concentration of Δ9-tetrahydrocannabinol is insufficient to produce a psychotropic effect. In an embodiment, the ratio of Δ9-tetrahydrocannabinol to the other cannabinoids is about 1:25. In another embodiment, the concentration of Δ9 tetrahydrocannabinol is less than about 1 mg/mL. In another embodiment, the concentration of Δ9-tetrahydrocannabinol is less than about 0.5 mg/mL. In another embodiment, the concentration of Δ9-tetrahydrocannabinol is less than about 0.3 mg/mL. In another embodiment, the concentration of Δ9-tetrahydrocannabinol is less than about 0.2 mg/mL. In another embodiment, the concentration of Δ9-tetrahydrocannabinol is less than about 0.1 mg/mL. In another embodiment, the concentration of Δ9-tetrahydrocannabinol is about 0 mg/mL.

In an embodiment, the ratio of cannabidiol to cannabidiolic acid is selected from the group consisting of about 1:100, about 1:50, about 1:10, and about 1:1. In another embodiment, the ratio of cannabidiol to cannabidiolic acid is about 1:1.

In an embodiment, the hemp extract comprises:
  about 1-10 mg/mL of cannabidiol;
  about 1-10 mg/mL of cannabidiolic acid;
  about 0.05-0.2 mg/mL cannabigerolic acid;
  about 0.1-0.3 mg/mL Δ9-tetrahydrocannabinol; and
  about 0.1-0.4 mg/mL cannabichromene.

In another embodiment, the hemp extract comprises:
  about 5 mg/mL of cannabidiol;
  about 5 mg/mL of cannabidiolic acid;
  about 0.11 mg/mL cannabigerolic acid;
  about 0.25 mg/mL Δ9-tetrahydrocannabinol; and
  about 0.27 mg/mL cannabichromene.

In another embodiment, the hemp extract comprises:
  about 0.09-0.13% α-pinene;
  about 0.23-0.44% β-myrcene;
  about 0.04-0.09% β-pinene;
  about 0.05-0.09% δ-limonene;
  about 0.03-0.06% linalool;
  about 0.04-0.07% β-caryophyllene;
  about 0.02-0.04% α-humulene;
  about 0.04-0.07% nerolidol 2;
  about 0.02-0.04% guaiol;
  about 0.04-0.08% caryophyllene oxide; and
  about 0.01-0.04% α-bisabolol.

In another embodiment, the hemp extract further comprises:
  camphene;
  β-ocimene;
  eucalyptol;
  isopulegol; and/or
  nerolidol 1.

In another embodiment, the hemp extract comprises:
  about 0.02% camphene;
  about 0.02-0.03% β-ocimene;
  about 0.02-0.05% eucalyptol;
  about 0.02% isopulegol; and/or
  about 0.02-0.04% nerolidol 1.

In an embodiment, the hemp extract comprises 5, 6, 7, 8, 9, 10, 11, 12, 13, 14, 15 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the composition is formulated in a carrier. In another embodiment, the carrier is selected from the group consisting of linseed oil, olive oil, fish oil, salmon oil, coconut oil, catnip oil, and grapeseed oil. In another embodiment, the carrier is grapeseed oil. In another embodiment, the carrier is catnip oil. In another embodiment, the composition comprises nepetalactone. In another embodiment, wherein the composition comprises taurine.

In an embodiment, the hemp extract comprises:
  cannabidiol;
  cannabidiolic acid;
  cannabigerolic acid;
  Δ9-tetrahydrocannabinol; and
  cannabichromene;

wherein the carrier is grapeseed oil.

In an embodiment, the composition is formulated for administration using a nebulizer. In another embodiment, the composition is formulated for administration using a diffuser. In another embodiment, the composition is formulated for administration using a pet collar. In another embodiment, the composition is formulated as a pet food for oral administration.

In an embodiment, the composition is formulated as a chew for oral administration. In another embodiment, the weight of the chew is about 0.5-10 g. In another embodiment, the weight of the chew is about 4 g, about 6 g, about 9 g, or about 10 g. In another embodiment, the weight of the chew is about 4 g.

In another embodiment, the chew comprises:
about 7 mg of cannabidiol;
about 6 mg of cannabidiolic acid;
about 0.12 mg cannabigerolic acid;
about 0.32 mg Δ9-tetrahydrocannabinol; and
about 0.36 mg cannabichromene.

In an embodiment, a dosage form comprises:
cannabidiol;
cannabidiolic acid;
cannabigerolic acid;
Δ9-tetrahydrocannabinol;
cannabichromene; and
one or more pharmaceutically acceptable additives, flavoring agents, surfactants, and adjuvants.

In another embodiment, the dosage form comprises:
about 1-10 mg/mL of cannabidiol;
about 1-10 mg/mL of cannabidiolic acid;
about 0.05-0.2 mg/mL cannabigerolic acid;
about 0.1-0.3 mg/mL Δ9-tetrahydrocannabinol; and
about 0.1-0.4 mg/mL cannabichromene.

In another embodiment, the dosage form comprises:
about 5 mg/mL of cannabidiol;
about 5 mg/mL of cannabidiolic acid;
about 0.11 mg/mL cannabigerolic acid;
about 0.25 mg/mL Δ9-tetrahydrocannabinol; and
about 0.27 mg/mL cannabichromene.

In an embodiment, the dosage form comprises:
α-pinene;
β-myrcene;
β-pinene;
δ-limonene;
linalool;
β-caryophyllene;
α-humulene;
nerolidol 2;
guaiol;
caryophyllene oxide; and
α-bisabolol.

In another embodiment, the dosage form comprises:
about 0.09-0.13% α-pinene;
about 0.23-0.44% β-myrcene;
about 0.04-0.09% β-pinene;
about 0.05-0.09% δ-limonene;
about 0.03-0.06% linalool;
about 0.04-0.07% β-caryophyllene;
about 0.02-0.04% α-humulene;
about 0.04-0.07% nerolidol 2;
about 0.02-0.04% guaiol;
about 0.04-0.08% caryophyllene oxide; and
about 0.01-0.04% α-bisabolol.

In another embodiment, the dosage form further comprises:
camphene;
β-ocimene;
eucalyptol;
isopulegol; and/or
nerolidol 1.

In another embodiment, the dosage form comprises:
about 0.02% camphene;
about 0.02-0.03% β-ocimene;
about 0.02-0.05% eucalyptol;
about 0.02% isopulegol; and/or
about 0.02-0.04% nerolidol 1.

In another embodiment, the dosage form comprises 5, 6, 7, 8, 9, 10, 11, 12, 13, 14, 15 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises a flavoring agent selected from the group consisting of catnip oil, peppermint oil, mango extract, beef, poultry, and seafood. In an embodiment, the flavoring agent is catnip oil. In an embodiment, the flavoring agent is selected from the group consisting of catnip oil, chicken liver powder, poultry extract, maltodextrin, butter, and bacon. In an embodiment, the flavoring agent is chicken liver powder.

In an embodiment, the dosage form comprises nepetalactone. In an embodiment, the dosage form comprises taurine.

In an embodiment, the dosage form is formulated as a chew for oral administration. In an embodiment, the chew is produced using cold extrusion. In another embodiment, the dosage form is formulated as a sublingual spray. In another embodiment, the dosage form is formulated as a water or alcohol soluble solution, a gel, or a cream for transdermal application. In another embodiment, the dosage form is formulated as a gel for buccal or mucosal administration. In another embodiment, the dosage form is formulated as a powder. In another embodiment, the dosage form is formulated as a solution for subcutaneous injection. In another embodiment, the dosage form is formulated as a tablet. In another embodiment, the dosage form is formulated as a capsule. In another embodiment, the dosage form is formulated as a hard chewable. In another embodiment, the dosage form is formulated for inhalation. In another embodiment, the dosage form is formulated for administration using a nebulizer. In another embodiment, the dosage form is formulated for administration using a diffuser. In another embodiment, the dosage form is formulated for administration using a pet collar.

In an embodiment, the dosage form is formulated in a carrier for oral administration. In an embodiment, the carrier is selected from the group consisting of linseed oil, olive oil, fish oil, salmon oil, coconut oil, catnip oil, and grapeseed oil. In another embodiment, the carrier is grapeseed oil. In another embodiment, the carrier is catnip oil.

In an embodiment, a dosage form comprises:
glucosamine HCl;
chondroitin sulfate (76%);
brewer's yeast;
arabic gum;
guar gum;
a flavoring agent;
Verdilox;
Previon;
hemp extract;
glycerin;
sunflower lecithin; and
water.

In another embodiment, the dosage form comprises:
about 12-17% glucosamine HCl;
about 1-4% chondroitin sulfate (76%);
about 29-33% brewer's yeast;
about 3-6% arabic gum;
about 0.5-2% guar gum;
about 12-16% of a flavoring agent;
about 0.01-0.1% Verdilox;
about 0.5-1.5% Previon;
about 3-6% hemp extract;
about 13-17% glycerin;
about 3-7% sunflower lecithin; and
about 3-7% water.
In another embodiment, the dosage form comprises:
about 15.6% glucosamine HCl;
about 2.6% chondroitin sulfate (76%);
about 30% brewer's yeast;
about 4.7% arabic gum;
about 0.9% guar gum;
about 14.2% of a flavoring agent;
about 0.05% Verdilox;
about 0.9% Previon;
about 4.7% hemp extract;
about 15.1% glycerin;
about 5.7% sunflower lecithin; and
about 5.7% water.
In an embodiment, a dosage form comprises:
glucosamine HCl;
hyaluronic acid;
brewer's yeast;
arabic gum;
guar gum;
a flavoring agent;
Verdilox;
Previon;
hemp extract;
glycerin;
sunflower lecithin; and
water.
In another embodiment, the dosage form comprises:
about 12-17% glucosamine HCl;
about 0.01-1% hyaluronic acid;
about 29-33% brewer's yeast;
about 3-6% arabic gum;
about 0.5-2% guar gum;
about 12-16% of a flavoring agent;
about 0.01-0.1% Verdilox;
about 0.5-1.5% Previon;
about 3-6% hemp extract;
about 13-17% glycerin;
about 3-7% sunflower lecithin; and
about 3-7% water.
In another embodiment, the dosage form comprises:
about 16% glucosamine HCl;
about 0.1% hyaluronic acid;
about 30.6% brewer's yeast;
about 4.8% arabic gum;
about 0.97% guar gum;
about 14.5% of a flavoring agent;
about 0.05% Verdilox;
about 0.97% Previon;
about 4.8% hemp extract;
about 15.5% glycerin;
about 5.8% sunflower lecithin; and
about 5.8% water.
In an embodiment, a dosage form comprises:
hemp extract;
peanut butter;
rice bran;
glucosamine HCL;
sweet potato;
dry molasses;
sorbic acid
brewer's yeast;
sugar;
water;
glycerin;
potato starch;
dehydrated peanut butter;
rice starch; and
guar gum.
In another embodiment, the dosage form comprises:
about 5.0% hemp extract;
about 15.0% peanut butter;
about 12.5% rice bran;
about 12.75% glucosamine HCL;
about 5.5% sweet potato;
about 8.0% dry molasses;
about 1% sorbic acid;
about 5.0% brewer's yeast;
about 6.0% sugar;
about 9.25% water;
about 13.0 glycerin;
about 2.0% potato starch;
about 1.0% dehydrated peanut butter;
about 2.0% rice starch; and
about 2.0% guar gum.
In another embodiment, the dosage form comprises:
about 5.0% hemp extract;
about 15.0% peanut butter;
about 13.0% rice bran;
about 8.5% glucosamine HCL;
about 6.0% sweet potato;
about 9.0% dry molasses;
about 1% sorbic acid;
about 5.0% brewer's yeast;
about 6.0% sugar;
about 9.5% water;
about 13.0 glycerin;
about 4.0% potato starch;
about 1.0% dehydrated peanut butter;
about 2.0% rice starch; and
about 2.0% guar gum.
In another embodiment, the dosage form comprises:
about 3.0-10.0% hemp extract;
about 10.0-20.0% peanut butter;
about 10.0-15.0% rice bran;
about 5.0-15.0% glucosamine HCL;
about 4.0-10.0% sweet potato;
about 6.0-13.0% dry molasses;
about 0.5-5.0% sorbic acid;
about 2.0-8.0% brewer's yeast;
about 3.0-8.0% sugar;
about 5.0-15.0% water;
about 8.0-18.0% glycerin;
about 1.0-8.0% potato starch;
about 0.5-5.0% dehydrated peanut butter;
about 1.0-5.0% rice starch; and
about 1.0-5.0% guar gum.
In an aspect, provided herein is a method for treating or reducing pain in a veterinary subject in need thereof, comprising administering to the subject a therapeutically effective amount of the compositions or a dosage forms described above. In an embodiment, the pain is associated with arthritis, post-operative pain, acute pain, dental pain, pain associated with gingivitis, or multi-joint pain.

In an embodiment, the pharmaceutical composition or dosage form is administered at a dosage of about 1.0 mg/kg twice daily. In another embodiment, the pharmaceutical composition or dosage form is administered at a dosage of about 1.0 mg/kg three times daily. In another embodiment, the pharmaceutical composition or dosage form is administered at a dosage of about 2.0 mg/kg twice daily. In another embodiment, the pharmaceutical composition or dosage form is administered at a dosage of about 2.0 mg/kg three times daily. In another embodiment, the pharmaceutical composition or dosage form is administered at a dosage of about 0.1-8.0 mg/kg.

In another embodiment, the pharmaceutical composition or dosage form is administered at twice the therapeutically effective dosage for one week, and then subsequently administered at a therapeutically effective dosage. In another embodiment, the therapeutically effective dosage is about 0.1-0.5 mg/kg. In another embodiment, the therapeutically effective dosage is about 2 mg/kg. In another embodiment, the therapeutically effective dosage is about 8 mg/kg. In another embodiment, the pharmaceutical composition or dosage form is administered at a dosage of about 1 mg/kg for one week, and then subsequently administered at a dosage of about 0.1-0.5 mg/kg. In another embodiment, the pharmaceutical composition or dosage form is administered at a dosage of about 4 mg/kg for one week, and then subsequently administered at a dosage of about 2 mg/kg.

In an embodiment, the method results in a therapeutically effective median maximal serum concentration of cannabidiol. In an embodiment, the median maximal serum concentration of cannabidiol is about 102 ng/mL. In another embodiment, the median maximal serum concentration of cannabidiol is about 590 ng/mL.

In an aspect, provided herein is a method for treating or reducing pain associated with arthritis, post-operative pain, acute pain, dental pain, pain associated with gingivitis, or multi-joint pain in a veterinary subject in need thereof, comprising administering to the subject a therapeutically effective amount of hemp extract.

In an embodiment, the hemp extract is administered at a dosage of about 0.1-8.0 mg/kg. In another embodiment, the hemp extract is administered at twice the therapeutically effective dosage for one week, and then subsequently administered at a therapeutically effective dosage. In another embodiment, the therapeutically effective dosage is about 0.1-0.5 mg/kg. In another embodiment, the therapeutically effective dosage is about 1 mg/kg. In another embodiment, the therapeutically effective dosage is about 2 mg/kg. In another embodiment, the therapeutically effective dosage is about 8 mg/kg.

In an embodiment, the hemp extract is administered at a dosage of about 1 mg/kg for one week, and then subsequently administered at a dosage of about 0.1-0.5 mg/kg. In another embodiment, the hemp extract is administered at a dosage of about 4 mg/kg for one week, and then subsequently administered at a dosage of about 2 mg/kg.

In an embodiment, the method results in a therapeutically effective median maximal serum concentration of cannabidiol. In another embodiment, the median maximal serum concentration of cannabidiol is about 102 ng/mL. In another embodiment, the median maximal serum concentration of cannabidiol is about 590 ng/mL.

In an embodiment, the veterinary subject is canine, feline, bovine, porcine, or equine. In another embodiment, the veterinary subject is canine. In another embodiment, the veterinary subject is feline.

In an aspect, provided herein is a method of achieving an area under the curve from 0 time to 24 hours of between 42.4 and 3048 ng hr/ml for cannabidiol in a veterinary subject comprising administering to the subject an effective amount of hemp extract. In an embodiment, the subject is canine or feline.

BRIEF DESCRIPTION OF THE FIGURES

FIGS. 5A-5F: Graphs showing trot stance % gait cycle symmetry (FIG. 5A), trot stance % gait cycle (FIG. 5B), trot step/stride ratio (FIG. 5C), walk stance % gait cycle symmetry (FIG. 5D), walk stance % gait cycle (FIG. 5E), and walk step/stride ratio (FIG. 5F) for five dogs treated with CBD.

DETAILED DESCRIPTION

Figure 1:
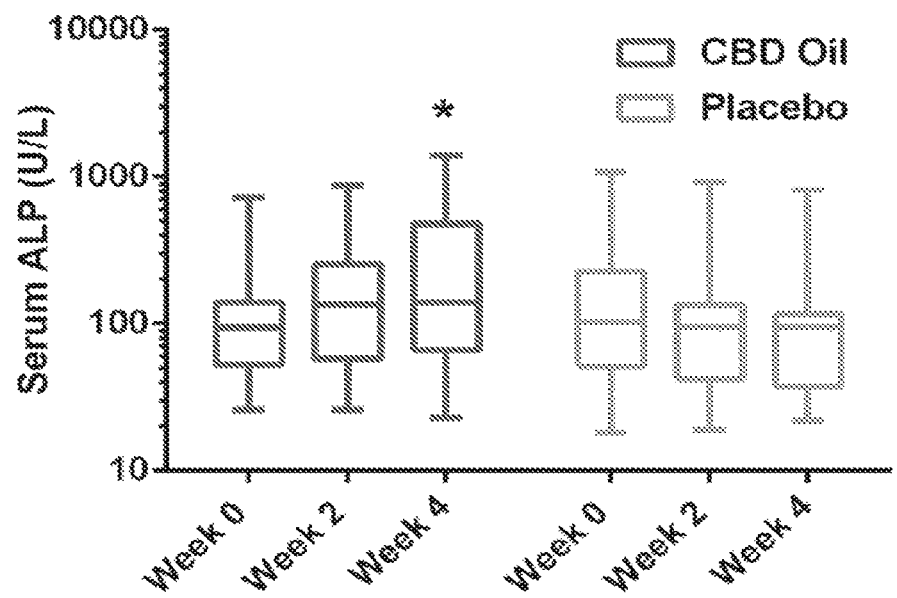
FIG. 1: Box-and-whisker plot of serum alkaline phosphatase (ALP) activity at each time for treatment and placebo oils. Box represents the mean and 25th and 75th percentile and the whiskers represent the 99th and 1st percentiles.

The endocannabinoid receptor system is known to play a role in pain modulation and attenuation of inflammation. Cannabinoid receptors (CB1 and CB2) are widely distributed throughout the central and peripheral nervous system and are also present in the synovium. However, the psychotropic effects of certain cannabinoids prevent extensive research into their use as single agents for pain relief. The cannabinoids are a group of as many as 60 different compounds that may or may not act at CB receptors. One class of cannabinoids, cannabidiol (CBD), may actually be an antagonist of the CB receptors. In lower vertebrates, CBD can also have immunomodulatory, anti-hyperalgesic, antinociceptive, and anti-inflammatory actions, making it an attractive therapeutic option in dogs with OA.

The present disclosure is directed toward compositions comprising hemp extract and their use for the treatment of pain in animals. Also provided herein are methods for treatment of pain in veterinary subjects. The efficacy of these compositions and treatment methods has not previously been demonstrated. Clinical trial and pharmacokinetic data regarding dosing is also provided herein.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±5%, from the specified value, as such variations are appropriate to perform the disclosed methods.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

All ranges disclosed herein are inclusive of the recited endpoint and independently combinable (for example, the range of "from 50 mg to 500 mg" is inclusive of the endpoints, 50 mg and 500 mg, and all the intermediate values). The endpoints of the ranges and any values disclosed herein are not limited to the precise range or value; they are sufficiently imprecise to include values approximating these ranges and/or values.

As used herein, the term "treatment" or "treating," is defined as the application or administration of a therapeutic agent, i.e., a compound provided herein (alone or in combination with another pharmaceutical agent), to a patient, or application or administration of a therapeutic agent to an isolated tissue or cell line from a patient (e.g., for diagnosis or ex vivo applications), with the purpose to cure, heal, alleviate, relieve, alter, remedy, ameliorate, improve or affect the symptoms of a disease, disorder, syndrome, or condition. Such treatments can be specifically tailored or modified, based on knowledge obtained from the field of pharmacogenomics.

In certain embodiments, the compositions described herein reduce pain in a subject. Pain can be measured using any metric known in the art. For example, pain can be measured using the canine brief pain inventory (CBPI), the Hudson activity scale, flexion and tension measurements and gait analysis. A reduction in any of these metrics shows a treatment of or reduction in pain.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "use" includes any one or more of the following embodiments of the invention, respectively: the use in the treatment of pain the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise.

As used herein, the term "patient," "individual," or "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from, schizophrenia. In another embodiment, the subject is a cell.

When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated.

In some embodiments, the individual is a mammal, including, but not limited to, bovine, equine, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. The term "individual" does not denote a particular age or sex.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" or "carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it can perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other nontoxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds can also be incorporated into the compositions. The "pharmaceutically acceptable carrier" or "carrier" can further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "stabilizer," as used herein, refers to polymers capable of chemically inhibiting or preventing degradation. Stabilizers are added to formulations of compounds to improve chemical and physical stability of the compound.

As used herein, the term "adjuvant" may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "weight percent" is meant to refer to the quantity by weight of a compound and/or component in a composition as the quantity by weight of a constituent component of the composition as a percentage of the weight of the total composition. The weight percent can also be calculated by multiplying the mass fraction by 100. The "mass fraction" is the ratio of one substance of a mass $m_1$ to the mass of the total composition $m_T$ such that weight percent=$(m_1/m_T)*100$.

"Aqueous buffer" refers to a water solution which resists change in hydronium ion and the hydroxide ion concentration (and consequent pH) upon addition of small amounts of acid or base, or upon dilution. Buffer solutions consist of a weak acid and its conjugate base (more common) or a weak base and its conjugate acid (less common). The buffer can be prepared by methods well known in the art with the appropriate buffering agents to give the desired pH value. Examples of the suitable buffering agents include hydrochloric acid, lactic acid, acetic acid, citric acid, malic acid, maleic acid, pyruvic acid, succinic acid, tris-hydroxymethylaminomethane, sodium hydroxide, sodium bicarbonate, phosphoric acid, sodium phosphate, and other biologically acceptable buffering agents. Aqueous buffers are readily available commercially and they can be used in preparation of the compositions of this invention without further treatment.

As used herein, the term "hemp extract" refers to a composition of cannabinoids and terpenes that are isolated from a hemp plant. The hemp extract can be obtained by any method known in the art. For example, the hemp extract can be obtained by supercritical (or subcritical) $CO_2$ extraction, which uses carbon dioxide under high pressure and low temperatures to isolate, preserve and maintain the purity of hemp extract. In an embodiment, the hemp extract is obtained from a supercritical $CO_2$ extraction. For example, supercritical $CO_2$ extraction may be performed as described in U.S. Pat. No. 8,895,078, which is incorporated herein by reference in its entirety. Alternatively, a solvent such as petroleum ether, ethanol, methanol, butanol, acetone, dry ice, or olive oil can be used, at room temperature (ambient temperature) with stirring, by passive extraction, heated to a temperature above room temperature, or under reflux, as known in the art to provide the hemp extract. In another embodiment, hemp extract from a butanol extraction is employed as starting material for methods disclosed herein.

As used herein, the term "flavoring agent" refers to an ingredient that is added to a composition to impart a particular flavor, smell, or other organoleptic property.

As used herein, the term "oil" refers to a nonpolar viscous liquid that is both hydrophobic and lipophilic. Oils may be isolated from animal, vegetable, or petrochemical products.

As used herein, the term "chew" refers to a product or a portion thereof that has rheological and other texture and organoleptic properties which tend to promote chewing upon the article by a target animal. Generally speaking, a chewable matrix will exhibit sufficient ductility that it is at least slightly malleable when bitten by the target animal and sufficient palatability that the target animal is not deterred by its taste from biting it multiple times. By contrast, "chewable" does not mean merely that an article can be chewed by an animal (i.e., it does not mean merely that some portion of the article will fit within an animal's mouth sufficiently to permit engagement of the animal's teeth against the portion).

The "maximal serum concentration level" of a substance, as used herein, refers to the maximal level of the substance found in a plasma sample following a single administration.

As used herein, the term "cold extrusion" refers to a process for producing edible food products comprising several unit operations including mixing, kneading, shearing, shaping, and forming, all of which are conducted at or near ambient temperature.

As used herein, the term "psychotropic effect" refers to a modification of brain function that results in an alteration of perception, mood, consciousness, or behavior.

Pharmaceutical Compositions

In an aspect, provided herein is a pharmaceutical composition comprising hemp extract and a carrier, wherein the hemp extract comprises:
  cannabidiol;
  cannabidiolic acid;
  cannabigerolic acid;
  Δ9-tetrahydrocannabinol; and
  cannabichromene.

In another embodiment, the ratio of Δ9-tetrahydrocannabinol to the other cannabinoids is from about 1:50 to about 1:20. In an embodiment, the ratio of cannabidiol to cannabidiolic acid is about 0.1:1 to about 1:0.1. In another embodiment, the ratio of cannabidiol to cannabidiolic acid is about 0.1:1, about 0.2:1, about 0.3:1, about 0.4:1, about 0.5:1, about 0.6:1, about 0.7:1, about 0.8:1, about 0.9:1, about 1:1, about 1:0.9, about 1:0.8, about 1:0.7, about 1:0.6, about 1:0.5, about 1:0.4, about 1:0.3, about 1:0.2, or about 1:0.1. In yet another embodiment, the ratio of cannabidiol to cannabidiolic acid is about 0.6:1 to about 1:0.6. In still another embodiment, the ratio of cannabidiol to cannabidiolic acid is about 1:1.

In an embodiment, the concentration of Δ9-tetrahydrocannabinol is insufficient to produce a psychotropic effect. In another embodiment, the ratio of Δ9-tetrahydrocannabinol to the other cannabinoids is from about 1:50 to about 1:20. In yet another embodiment, the ratio of Δ9-tetrahydrocannabinol to the other cannabinoids is about 1:50. In still another embodiment, the ratio of Δ9-tetrahydrocannabinol to the other cannabinoids is about 1:45. In an embodiment, the ratio of Δ9-tetrahydrocannabinol to the other cannabinoids is about 1:40. In another embodiment, the ratio of Δ9-tetrahydrocannabinol to the other cannabinoids is about 1:35. In yet another embodiment, the ratio of Δ9-tetrahydrocannabinol to the other cannabinoids is about 1:30. In still another embodiment, the ratio of Δ9-tetrahydrocannabinol to the other cannabinoids is about 1:25. In an embodiment, the ratio of Δ9-tetrahydrocannabinol to the other cannabinoids is about 1:20.

In an embodiment, the concentration of Δ9-tetrahydrocannabinol is less than about 2 mg/mL. In another embodiment, the concentration of Δ9-tetrahydrocannabinol is less than about 1.5 mg/mL. In yet another embodiment, the concentration of Δ9-tetrahydrocannabinol is less than about 1 mg/mL. In still another embodiment, the concentration of Δ9-tetrahydrocannabinol is less than about 0.9 mg/mL. In yet another embodiment, the concentration of Δ9-tetrahydrocannabinol is less than about 0.8 mg/mL. In an embodiment, the concentration of Δ9-tetrahydrocannabinol is less than about 0.7 mg/mL. In another embodiment, the concentration of Δ9-tetrahydrocannabinol is less than about 0.6 mg/mL. In yet another embodiment, the concentration of Δ9-tetrahydrocannabinol is less than about 0.5 mg/mL. In still another embodiment, the concentration of Δ9-tetrahydrocannabinol is less than about 0.4 mg/mL. In an embodiment, the concentration of Δ9-tetrahydrocannabinol is less than about 0.3 mg/mL. In another embodiment, the concentration of Δ9-tetrahydrocannabinol is less than about 0.2 mg/mL. In yet another embodiment, the concentration of Δ9-tetrahydrocannabinol is less than about 0.1 mg/mL. In another embodiment, the concentration of Δ9-tetrahydrocannabinol is about 0 mg/mL.

In an embodiment, the hemp extract comprises:
  about 0.1-20 mg/mL of cannabidiol;
  about 0.1-20 mg/mL of cannabidiolic acid;
  about 0.01-0.5 mg/mL cannabigerolic acid;
  about 0.01-0.5 mg/mL Δ9-tetrahydrocannabinol; and
  about 0.01-0.5 mg/mL cannabichromene.

In another embodiment, the hemp extract comprises:
  about 1-10 mg/mL of cannabidiol;
  about 1-10 mg/mL of cannabidiolic acid;
  about 0.05-0.2 mg/mL cannabigerolic acid;
  about 0.1-0.3 mg/mL Δ9-tetrahydrocannabinol; and
  about 0.1-0.4 mg/mL cannabichromene.

In yet another embodiment, the hemp extract comprises:
  about 5 mg/mL of cannabidiol;
  about 5 mg/mL of cannabidiolic acid;
  about 0.11 mg/mL cannabigerolic acid;
  about 0.25 mg/mL Δ9-tetrahydrocannabinol; and
  about 0.27 mg/mL cannabichromene.

In an embodiment, provided herein is a pharmaceutical composition comprising hemp extract and a carrier, wherein the hemp extract comprises:
  α-pinene;
  β-myrcene;
  β-pinene;
  δ-limonene;
  linalool;
  β-caryophyllene;
  α-humulene;
  nerolidol 2;
  guaiol;
  caryophyllene oxide; and
  α-bisabolol.

In another embodiment, the hemp extract comprises:
  about 0.09-0.13% α-pinene;
  about 0.23-0.44% β-myrcene;
  about 0.04-0.09% β-pinene;
  about 0.05-0.09% δ-limonene;
  about 0.03-0.06% linalool;

about 0.04-0.07% β-caryophyllene;
about 0.02-0.04% α-humulene;
about 0.04-0.07% nerolidol 2;
about 0.02-0.04% guaiol;
about 0.04-0.08% caryophyllene oxide; and
about 0.01-0.04% α-bisabolol.

In another embodiment, the hemp extract comprises:
about 0.07-0.30% α-pinene;
about 0.10-0.60% β-myrcene;
about 0.02-0.20% β-pinene;
about 0.03-0.20% δ-limonene;
about 0.01-0.08% linalool;
about 0.03-0.09% β-caryophyllene;
about 0.01-0.06% α-humulene;
about 0.02-0.09% nerolidol 2; and
about 0.01-0.06% guaiol;

In another embodiment, the hemp extract comprises:
about 0.01-0.50% α-pinene;
about 0.01-0.90% β-myrcene;
about 0.01-0.50% β-pinene;
about 0.01-0.50% δ-limonene;
about 0.01-0.50% linalool;
about 0.01-0.50% β-caryophyllene;
about 0.01-0.50% α-humulene;
about 0.01-0.50% nerolidol 2;
about 0.01-0.50% guaiol;
about 0.01-0.50% caryophyllene oxide; and
about 0.01-0.50% α-bisabolol.

In another embodiment, the hemp extract further comprises:
camphene;
β-ocimene;
eucalyptol;
isopulegol; and/or
nerolidol 1.

In another embodiment, the hemp extract comprises:
about 0.02% camphene;
about 0.02-0.03% β-ocimene;
about 0.02-0.05% eucalyptol;
about 0.02% isopulegol; and/or
about 0.02-0.04% nerolidol 1.

In another embodiment, the hemp extract comprises:
about 0.01-0.04% camphene;
about 0.01-0.05% β-ocimene;
about 0.01-0.07% eucalyptol;
about 0.01-0.04% isopulegol; and/or
about 0.01-0.05% nerolidol 1.

In another embodiment, the hemp extract comprises:
about 0.01-0.50% camphene;
about 0.01-0.50% β-ocimene;
about 0.01-0.50% eucalyptol;
about 0.01-0.50% isopulegol; and/or
about 0.01-0.50% nerolidol 1.

In an embodiment, the hemp extract comprises 1 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 2 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 3 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 4 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 5 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 6 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 7 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 8 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 9 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 10 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 11 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 12 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 13 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 14 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 15 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the composition is formulated as an oil. In another embodiment, the carrier is selected from the group consisting of linseed oil, olive oil, fish oil, salmon oil, coconut oil, catnip oil and grapeseed oil. In yet another embodiment, the carrier is grapeseed oil.

In an embodiment, the dosage form comprises nepetalactone.

In an embodiment, the dosage form comprises taurine.

In an embodiment, the pharmaceutical composition is formulated as a sublingual spray. In still another embodiment, the pharmaceutical composition is formulated as a water or alcohol soluble solution, a gel, or a cream for transdermal application. In an embodiment, the dosage form is formulated as a gel for buccal or mucosal administration. In an embodiment, the pharmaceutical composition is formulated as a powder. In another embodiment, the pharmaceutical composition is formulated as a solution for subcutaneous injection. In yet another embodiment, the pharmaceutical composition is formulated as a tablet. In still another embodiment, the pharmaceutical composition is formulated as a capsule. In an embodiment, the pharmaceutical composition is formulated as a hard chewable.

In an embodiment, the composition is formulated as a chew for oral administration. In another embodiment, the chew is produced using cold extrusion. In another embodiment, the weight of the chew is about 0.5-10 g. In yet another embodiment, the weight of the chew is about 4 g, about 6 g, about 9 g, or about 10 g. In still another embodiment, the weight of the chew is about 0.5 g. In an embodiment, the weight of the chew is about 1 g. In another embodiment, the weight of the chew is about 1.5 g. In yet another embodiment, the weight of the chew is about 2 g. In still another embodiment, the weight of the chew is about 3 g. In an embodiment, the weight of the chew is about 4 g. In another embodiment, the weight of the chew is about 5 g. In yet another embodiment, the weight of the chew is about 6 g. In still another embodiment, the weight of the chew is about 7 g. In an embodiment, the weight of the chew is about 8 g. In another embodiment, the weight of the chew is about 9 g. In yet another embodiment, the weight of the chew is about 10 g.

In an embodiment, the 4 g chew comprises:
about 7 mg of cannabidiol;
about 6 mg of cannabidiolic acid;
about 0.12 mg cannabigerolic acid;
about 0.32 mg Δ9-tetrahydrocannabinol; and
about 0.36 mg cannabichromene.

The pharmaceutical compositions of the present disclosure may be manufactured by processes well known in the art, e.g., by means of conventional mixing, dissolving, granulating, grinding, pulverizing, dragee-making, levigating, emulsifying, encapsulating, entrapping or by lyophilizing processes.

The compositions for use in accordance with the present disclosure thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

Dosage Forms

In an aspect, provided herein is a dosage form comprising:
cannabidiol;
cannabidiolic acid;
cannabigerolic acid;
Δ9-tetrahydrocannabinol;
cannabichromene; and
one or more pharmaceutically acceptable additives, flavoring agents, surfactants, and adjuvants.

In an embodiment, the ratio of cannabidiol to cannabidiolic acid is selected from the group consisting of about 1:100, about 1:50, about 1:10, and about 1:1. In an embodiment, the ratio of cannabidiol to cannabidiolic acid is about 0.1:1 to about 1:0.1. In another embodiment, the ratio of cannabidiol to cannabidiolic acid is about 0.1:1, about 0.2:1, about 0.3:1, about 0.4:1, about 0.5:1, about 0.6:1, about 0.7:1, about 0.8:1, about 0.9:1, about 1:1, about 1:0.9, about 1:0.8, about 1:0.7, about 1:0.6, about 1:0.5, about 1:0.4, about 1:0.3, about 1:0.2, or about 1:0.1. In yet another embodiment, the ratio of cannabidiol to cannabidiolic acid is about 0.6:1 to about 1:0.6. In still another embodiment, the ratio of cannabidiol to cannabidiolic acid is about 1:1.

In an embodiment, the concentration of Δ9-tetrahydrocannabinol is insufficient to produce a psychotropic effect. In another embodiment, the ratio of Δ9-tetrahydrocannabinol to the other cannabinoids is from about 1:50 to about 1:20. In yet another embodiment, the ratio of Δ9-tetrahydrocannabinol to the other cannabinoids is about 1:50. In still another embodiment, the ratio of Δ9-tetrahydrocannabinol to the other cannabinoids is about 1:45. In an embodiment, the ratio of Δ9-tetrahydrocannabinol to the other cannabinoids is about 1:40. In another embodiment, the ratio of Δ9-tetrahydrocannabinol to the other cannabinoids is about 1:35. In yet another embodiment, the ratio of Δ9-tetrahydrocannabinol to the other cannabinoids is about 1:30. In still another embodiment, the ratio of Δ9-tetrahydrocannabinol to the other cannabinoids is about 1:25. In an embodiment, the ratio of Δ9-tetrahydrocannabinol to the other cannabinoids is about 1:20.

In an embodiment, the concentration of Δ9-tetrahydrocannabinol is less than about 2 mg/mL. In another embodiment, the concentration of Δ9-tetrahydrocannabinol is less than about 1.5 mg/mL. In yet another embodiment, the concentration of Δ9-tetrahydrocannabinol is less than about 1 mg/mL. In still another embodiment, the concentration of Δ9-tetrahydrocannabinol is less than about 0.9 mg/mL. In yet another embodiment, the concentration of Δ9-tetrahydrocannabinol is less than about 0.8 mg/mL. In an embodiment, the concentration of Δ9-tetrahydrocannabinol is less than about 0.7 mg/mL. In another embodiment, the concentration of Δ9-tetrahydrocannabinol is less than about 0.6 mg/mL. In yet another embodiment, the concentration of Δ9-tetrahydrocannabinol is less than about 0.5 mg/mL. In still another embodiment, the concentration of Δ9-tetrahydrocannabinol is less than about 0.4 mg/mL. In an embodiment, the concentration of Δ9-tetrahydrocannabinol is less than about 0.3 mg/mL. In another embodiment, the concentration of Δ9-tetrahydrocannabinol is less than about 0.2 mg/mL. In yet another embodiment, the concentration of Δ9-tetrahydrocannabinol is less than about 0.1 mg/mL. In another embodiment, the concentration of Δ9-tetrahydrocannabinol is about 0 mg/mL.

In an embodiment, the dosage form comprises:
about 0.1-20 mg/mL of cannabidiol;
about 0.1-20 mg/mL of cannabidiolic acid;
about 0.01-0.5 mg/mL cannabigerolic acid;
about 0.01-0.5 mg/mL Δ9-tetrahydrocannabinol; and
about 0.01-0.5 mg/mL cannabichromene.

In another embodiment, the dosage form comprises:
about 1-10 mg/mL of cannabidiol;
about 1-10 mg/mL of cannabidiolic acid;
about 0.05-0.2 mg/mL cannabigerolic acid;
about 0.1-0.3 mg/mL Δ9-tetrahydrocannabinol; and
about 0.1-0.4 mg/mL cannabichromene.

In yet another embodiment, the dosage form comprises:
about 5 mg/mL of cannabidiol;
about 5 mg/mL of cannabidiolic acid;
about 0.11 mg/mL cannabigerolic acid;
about 0.25 mg/mL Δ9-tetrahydrocannabinol; and
about 0.27 mg/mL cannabichromene.

In some embodiments, the dosage form comprises:
α-pinene;
β-myrcene;
β-pinene;
δ-limonene;
linalool;
β-caryophyllene;
α-humulene;
nerolidol 2;
guaiol;
caryophyllene oxide; and
α-bisabolol.

In another embodiment, the dosage form comprises:
about 0.09-0.13% α-pinene;
about 0.23-0.44% β-myrcene;
about 0.04-0.09% β-pinene;
about 0.05-0.09% δ-limonene;
about 0.03-0.06% linalool;
about 0.04-0.07% β-caryophyllene;
about 0.02-0.04% α-humulene;
about 0.04-0.07% nerolidol 2;
about 0.02-0.04% guaiol;
about 0.04-0.08% caryophyllene oxide; and
about 0.01-0.04% α-bisabolol.

In another embodiment, the dosage form comprises:
about 0.07-0.30% α-pinene;
about 0.10-0.60% β-myrcene;
about 0.02-0.20% β-pinene;
about 0.03-0.20% δ-limonene;
about 0.01-0.08% linalool;
about 0.03-0.09% β-caryophyllene;
about 0.01-0.06% α-humulene;
about 0.02-0.09% nerolidol 2; and
about 0.01-0.06% guaiol;

In another embodiment, the dosage form comprises:
about 0.01-0.50% α-pinene;
about 0.01-0.90% β-myrcene;
about 0.01-0.50% β-pinene;
about 0.01-0.50% δ-limonene;
about 0.01-0.50% linalool;
about 0.01-0.50% β-caryophyllene;
about 0.01-0.50% α-humulene;
about 0.01-0.50% nerolidol 2;
about 0.01-0.50% guaiol;
about 0.01-0.50% caryophyllene oxide; and
about 0.01-0.50% α-bisabolol.

In another embodiment, the dosage form further comprises:
camphene;
β-ocimene;
eucalyptol;
isopulegol; and/or
nerolidol 1.

In another embodiment, the dosage form comprises:
about 0.02% camphene;
about 0.02-0.03% β-ocimene;
about 0.02-0.05% eucalyptol;
about 0.02% isopulegol; and/or
about 0.02-0.04% nerolidol 1.

In another embodiment, the dosage form comprises:
about 0.01-0.04% camphene;
about 0.01-0.05% β-ocimene;
about 0.01-0.07% eucalyptol;
about 0.01-0.04% isopulegol; and/or
about 0.01-0.05% nerolidol 1.

In another embodiment, the dosage form comprises:
about 0.01-0.50% camphene;
about 0.01-0.50% β-ocimene;
about 0.01-0.50% eucalyptol;
about 0.01-0.50% isopulegol; and/or
about 0.01-0.50% nerolidol 1.

In an embodiment, the hemp extract comprises 1 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 2 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 3 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the hemp extract comprises 4 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 5 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 6 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 7 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 8 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 9 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 10 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 11 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 12 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 13 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 14 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises 15 or more of the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1.

In an embodiment, the dosage form comprises the following: α-pinene, β-myrcene, β-pinene, δ-limonene, linalool, β-caryophyllene, α-humulene, nerolidol 2, guaiol, caryophyllene oxide, α-bisabolol, camphene, β-ocimene, eucalyptol, isopulegol, and nerolidol 1

In an embodiment, the flavoring agent is selected from the group consisting of catnip oil, peppermint oil, mango extract, beef, poultry, and seafood.

In an embodiment, the dosage form is formulated as a sublingual spray. In still another embodiment, the dosage form is formulated as a water or alcohol soluble solution, a gel, or a cream for transdermal application. In an embodiment, the dosage form is formulated as a powder. In an embodiment, the dosage form is formulated as a gel for buccal or mucosal administration. In another embodiment, the dosage form is formulated as a solution for subcutaneous injection. In yet another embodiment, the dosage form is formulated as a tablet. In still another embodiment, the dosage form is formulated as a capsule. In an embodiment, the dosage form is formulated as a hard chewable.

In some embodiments, the invention includes infusing edible products with hemp extract. In another embodiment, the edible product is an extruded food product, baked food product, nut butter, spread, pelleted feed, or processed food. In another embodiment, the edible product is a pet food. In another embodiment the pet food is in a dry, shelf-stable form such as dried meals, dried fish, dried dairy products, fish meal, fish flour, cereals, flours, carbohydrates, dried fruits, etc. In another embodiment, the pet food is moist or semi-moist. In another embodiment, the pet food contains food additives or supplements such as vitamins, minerals, medicinals, etc., for example chemicals, enzymes, etc., capable of removing plaque or tartar from the animal's teeth, etc.

In an embodiment, the hemp extract is administered with catnip oil. In another embodiment, any of the dosage forms described can also include catnip.

In another embodiment, hemp extracts are administered using a nebulizer. In another embodiment, the nebulizer delivery device and system is capable of effectively and efficiently administering one or more nebulized drug to an animal. In another embodiment, the nebulizer system can easily be used on animals without removing them from their natural environment. In another embodiment, the nebulizer delivery device and system enables animals to be easily treated daily or multiple times a day without undue stress or the need for extensive resources. In another embodiment, the nebulizer delivery device and system can be used on animals having varying levels of training.

In one embodiment, hemp extract is administered using a diffuser. The diffuser can be any device which disperses hemp extract into the air. Hemp extract may be dispersed by any method, including by natural convection, by forced convection, by heating a wick or pad, for example, holding the hemp extract, by using pumps, or with fans.

In one embodiment, hemp extract is administered by a pet collar. The pet collar may comprise a belt with a buckle on one side, a free end on the other side and an attachment means, such as apertures disposed longitudinally within the central portion of the belt, or a quick release clasp mechanism, for securing the collar in a closed loop configuration. The pet collar may be made from a variety of materials including nylon, polyester leather or other suitable material. The belt material may be treated with a water-proofing compound. The nylon or polyester belt may be interwoven with reflective fibers to enhance the visibility of the pet collar during nighttime hours. In one embodiment, the collar is infused with hemp extract.

Chews

In an embodiment, the dosage form is formulated as a chew for oral administration. In another embodiment, the chew is produced using cold extrusion. In another embodiment, the weight of the chew is about 0.5-10 g. In yet another embodiment, the weight of the chew is about 4 g, about 6 g, about 9 g, or about 10 g. In still another embodiment, the weight of the chew is about 0.5 g. In an embodiment, the weight of the chew is about 1 g. In another embodiment, the weight of the chew is about 1.5 g. In yet another embodiment, the weight of the chew is about 2 g. In still another embodiment, the weight of the chew is about 3 g. In an embodiment, the weight of the chew is about 4 g. In another embodiment, the weight of the chew is about 5 g. In yet another embodiment, the weight of the chew is about 6 g. In still another embodiment, the weight of the chew is about 7 g. In an embodiment, the weight of the chew is about 8 g. In another embodiment, the weight of the chew is about 9 g. In yet another embodiment, the weight of the chew is about 10 g.

In one embodiment, the dosage form comprises:
glucosamine HCl;
chondroitin sulfate (76%);
brewer's yeast;
arabic gum;
guar gum;
a flavoring agent;
Verdilox;
Previon;
hemp extract;
glycerin;
sunflower lecithin; and
water.

In another embodiment, the dosage form comprises:
about 10-20% glucosamine HCl;
about 0.1-7% chondroitin sulfate (76%);
about 25-35% brewer's yeast;
about 1-10% arabic gum;
about 0.1-4% guar gum;
about 10-20% of a flavoring agent;
about 0.01-1% Verdilox;
about 0.1-2% Previon;
about 1-10% hemp extract;
about 10-20% glycerin;
about 1-10% sunflower lecithin; and
about 1-10% water.

In another embodiment, the dosage form comprises:
about 12-17% glucosamine HCl;
about 1-4% chondroitin sulfate (76%);
about 29-33% brewer's yeast;
about 3-6% arabic gum;
about 0.5-2% guar gum;
about 12-16% of a flavoring agent;
about 0.01-0.1% Verdilox;
about 0.5-1.5% Previon;
about 3-6% hemp extract;
about 13-17% glycerin;
about 3-7% sunflower lecithin; and
about 3-7% water.
In yet another embodiment, the dosage form comprises:
about 15.6% glucosamine HCl;
about 2.6% chondroitin sulfate (76%);
about 30% brewer's yeast;
about 4.7% arabic gum;
about 0.9% guar gum;
about 14.2% of a flavoring agent;
about 0.05% Verdilox;
about 0.9% Previon;
about 4.7% hemp extract;
about 15.1% glycerin;
about 5.7% sunflower lecithin; and
about 5.7% water.
In another embodiment, the dosage form comprises:
glucosamine HCl;
hyaluronic acid;
brewer's yeast;
arabic gum;
guar gum;
a flavoring agent;
Verdilox;
Previon;
hemp extract;
glycerin;
sunflower lecithin; and
water.
In another embodiment, the dosage form comprises:
about 10-20% glucosamine HCl;
about 0.01-3% hyaluronic acid;
about 25-35% brewer's yeast;
about 1-10% arabic gum;
about 0.1-5% guar gum;
about 10-20% of a flavoring agent;
about 0.01-1% Verdilox;
about 0.1-3% Previon;
about 1-10% hemp extract;
about 10-20% glycerin;
about 1-10% sunflower lecithin; and
about 1-10% water.
In another embodiment, the dosage form comprises:
about 12-17% glucosamine HCl;
about 0.01-1% hyaluronic acid;
about 29-33% brewer's yeast;
about 3-6% arabic gum;
about 0.5-2% guar gum;
about 12-16% of a flavoring agent;
about 0.01-0.1% Verdilox;
about 0.5-1.5% Previon;
about 3-6% hemp extract;
about 13-17% glycerin;
about 3-7% sunflower lecithin; and
about 3-7% water.

In yet another embodiment, the dosage form comprises:
about 16% glucosamine HCl;
about 0.1% hyaluronic acid;
about 30.6% brewer's yeast;
about 4.8% arabic gum;
about 0.97% guar gum;
about 14.5% of a flavoring agent;
about 0.05% Verdilox;
about 0.97% Previon;
about 4.8% hemp extract;
about 15.5% glycerin;
about 5.8% sunflower lecithin; and
about 5.8% water.
In yet another embodiment, the dosage form comprises:
hemp extract;
peanut butter;
rice bran;
glucosamine HCL;
sweet potato;
dry molasses;
sorbic acid
brewer's yeast;
sugar;
water;
glycerin;
potato starch;
dehydrated peanut butter;
rice starch; and
guar gum.
In yet another embodiment, the dosage form comprises:
about 5.0% hemp extract;
about 15.0% peanut butter;
about 12.5% rice bran;
about 12.75% glucosamine HCL;
about 5.5% sweet potato;
about 8.0% dry molasses;
about 1% sorbic acid;
about 5.0% brewer's yeast;
about 6.0% sugar;
about 9.25% water;
about 13.0 glycerin;
about 2.0% potato starch;
about 1.0% dehydrated peanut butter;
about 2.0% rice starch; and
about 2.0% guar gum.
In yet another embodiment, the dosage form comprises:
about 5.0% hemp extract;
about 15.0% peanut butter;
about 13.0% rice bran;
about 8.5% glucosamine HCL;
about 6.0% sweet potato;
about 9.0% dry molasses;
about 1% sorbic acid;
about 5.0% brewer's yeast;
about 6.0% sugar;
about 9.5% water;
about 13.0 glycerin;
about 4.0% potato starch;
about 1.0% dehydrated peanut butter;
about 2.0% rice starch; and
about 2.0% guar gum.
In yet another embodiment, the dosage form comprises:
about 3.0-10.0% hemp extract;
about 10.0-20.0% peanut butter;
about 10.0-15.0% rice bran;
about 5.0-15.0% glucosamine HCL;
about 4.0-10.0% sweet potato;

about 6.0-13.0% dry molasses;
about 0.5-5.0% sorbic acid;
about 2.0-8.0% brewer's yeast;
about 3.0-8.0% sugar;
about 5.0-15.0% water;
about 8.0-18.0% glycerin;
about 1.0-8.0% potato starch;
about 0.5-5.0% dehydrated peanut butter;
about 1.0-5.0% rice starch; and
about 1.0-5.0% guar gum.

In another embodiment, the dosage form comprises 2.0% hemp extract. In another embodiment, the dosage form comprises 3.0% hemp extract. In another embodiment, the dosage form comprises 4.0% hemp extract. In another embodiment, the dosage form comprises 5.0% hemp extract. In another embodiment, the dosage form comprises 6.0% hemp extract. In another embodiment, the dosage form comprises 7.0% hemp extract. In another embodiment, the dosage form comprises 8.0% hemp extract. In another embodiment, the dosage form comprises 9.0% hemp extract. In another embodiment, the dosage form comprises 10.0% hemp extract.

In an embodiment, the hemp extract comprises:
cannabidiol;
cannabidiolic acid;
cannabigerolic acid;
Δ9-tetrahydrocannabinol; and
cannabichromene.

In an embodiment, the ratio of cannabidiol to cannabidiolic acid is selected from the group consisting of about 1:100, about 1:50, about 1:10, and about 1:1. In an embodiment, the ratio of cannabidiol to cannabidiolic acid is about 0.1:1 to about 1:0.1. In another embodiment, the ratio of cannabidiol to cannabidiolic acid is about 0.1:1, about 0.2:1, about 0.3:1, about 0.4:1, about 0.5:1, about 0.6:1, about 0.7:1, about 0.8:1, about 0.9:1, about 1:1, about 1:0.9, about 1:0.8, about 1:0.7, about 1:0.6, about 1:0.5, about 1:0.4, about 1:0.3, about 1:0.2, or about 1:0.1. In yet another embodiment, the ratio of cannabidiol to cannabidiolic acid is about 0.6:1 to about 1:0.6. In still another embodiment, the ratio of cannabidiol to cannabidiolic acid is about 1:1.

In an embodiment, the concentration of Δ9-tetrahydrocannabinol is insufficient to produce a psychotropic effect. In another embodiment, the ratio of Δ9-tetrahydrocannabinol to the other cannabinoids is from about 1:50 to about 1:20. In yet another embodiment, the ratio of Δ9-tetrahydrocannabinol to the other cannabinoids is about 1:50. In still another embodiment, the ratio of Δ9-tetrahydrocannabinol to the other cannabinoids is about 1:45. In an embodiment, the ratio of Δ9-tetrahydrocannabinol to the other cannabinoids is about 1:40. In another embodiment, the ratio of Δ9-tetrahydrocannabinol to the other cannabinoids is about 1:35. In yet another embodiment, the ratio of Δ9-tetrahydrocannabinol to the other cannabinoids is about 1:30. In still another embodiment, the ratio of Δ9-tetrahydrocannabinol to the other cannabinoids is about 1:25. In an embodiment, the ratio of Δ9-tetrahydrocannabinol to the other cannabinoids is about 1:20.

In an embodiment, the concentration of Δ9-tetrahydrocannabinol is less than about 2 mg/mL. In another embodiment, the concentration of Δ9-tetrahydrocannabinol is less than about 1.5 mg/mL. In yet another embodiment, the concentration of Δ9-tetrahydrocannabinol is less than about 1 mg/mL. In still another embodiment, the concentration of Δ9-tetrahydrocannabinol is less than about 0.9 mg/mL. In yet another embodiment, the concentration of Δ9-tetrahydrocannabinol is less than about 0.8 mg/mL. In an embodiment, the concentration of Δ9-tetrahydrocannabinol is less than about 0.7 mg/mL. In another embodiment, the concentration of Δ9-tetrahydrocannabinol is less than about 0.6 mg/mL. In yet another embodiment, the concentration of Δ9-tetrahydrocannabinol is less than about 0.5 mg/mL. In still another embodiment, the concentration of Δ9-tetrahydrocannabinol is less than about 0.4 mg/mL. In an embodiment, the concentration of Δ9-tetrahydrocannabinol is less than about 0.3 mg/mL. In another embodiment, the concentration of Δ9-tetrahydrocannabinol is less than about 0.2 mg/mL. In yet another embodiment, the concentration of Δ9-tetrahydrocannabinol is less than about 0.1 mg/mL. In yet another embodiment, the concentration of Δ9-tetrahydrocannabinol is about 0 mg/mL.

In an embodiment, the hemp extract comprises:
about 0.1-20 mg/mL of cannabidiol;
about 0.1-20 mg/mL of cannabidiolic acid;
about 0.01-0.5 mg/mL cannabigerolic acid;
about 0.01-0.5 mg/mL Δ9-tetrahydrocannabinol; and
about 0.01-0.5 mg/mL cannabichromene.

In another embodiment, the hemp extract comprises:
about 1-10 mg/mL of cannabidiol;
about 1-10 mg/mL of cannabidiolic acid;
about 0.05-0.2 mg/mL cannabigerolic acid;
about 0.1-0.3 mg/mL Δ9-tetrahydrocannabinol; and
about 0.1-0.4 mg/mL cannabichromene.

In yet another embodiment, the hemp extract comprises:
about 5 mg/mL of cannabidiol;
about 5 mg/mL of cannabidiolic acid;
about 0.11 mg/mL cannabigerolic acid;
about 0.25 mg/mL Δ9-tetrahydrocannabinol; and
about 0.27 mg/mL cannabichromene.

In an embodiment, the hemp extract comprises:
α-pinene;
β-myrcene;
β-pinene;
δ-limonene;
linalool;
β-caryophyllene;
α-humulene;
nerolidol 2;
guaiol;
caryophyllene oxide; and
α-bisabolol.

In another embodiment, the hemp extract comprises:
about 0.09-0.13% α-pinene;
about 0.23-0.44% β-myrcene;
about 0.04-0.09% β-pinene;
about 0.05-0.09% δ-limonene;
about 0.03-0.06% linalool;
about 0.04-0.07% β-caryophyllene;
about 0.02-0.04% α-humulene;
about 0.04-0.07% nerolidol 2;
about 0.02-0.04% guaiol;
about 0.04-0.08% caryophyllene oxide; and
about 0.01-0.04% α-bisabolol.

In another embodiment, the hemp extract comprises:
about 0.07-0.30% α-pinene;
about 0.10-0.60% β-myrcene;
about 0.02-0.20% β-pinene;
about 0.03-0.20% δ-limonene;
about 0.01-0.08% linalool;
about 0.03-0.09% β-caryophyllene;
about 0.01-0.06% α-humulene;
about 0.02-0.09% nerolidol 2; and
about 0.01-0.06% guaiol;

In another embodiment, the hemp extract comprises:
about 0.01-0.50% α-pinene;
about 0.01-0.90% β-myrcene;
about 0.01-0.50% β-pinene;
about 0.01-0.50% δ-limonene;
about 0.01-0.50% linalool;
about 0.01-0.50% β-caryophyllene;
about 0.01-0.50% α-humulene;
about 0.01-0.50% nerolidol 2;
about 0.01-0.50% guaiol;
about 0.01-0.50% caryophyllene oxide; and
about 0.01-0.50% α-bisabolol.

In another embodiment, the hemp extract further comprises:
camphene;
β-ocimene;
eucalyptol;
isopulegol; and/or
nerolidol 1.

In another embodiment, the hemp extract comprises:
about 0.02% camphene;
about 0.02-0.03% β-ocimene;
about 0.02-0.05% eucalyptol;
about 0.02% isopulegol; and/or
about 0.02-0.04% nerolidol 1.

In another embodiment, the hemp extract comprises:
about 0.01-0.04% camphene;
about 0.01-0.05% β-ocimene;
about 0.01-0.07% eucalyptol;
about 0.01-0.04% isopulegol; and/or
about 0.01-0.05% nerolidol 1.

In another embodiment, the hemp extract comprises:
about 0.01-0.50% camphene;
about 0.01-0.50% β-ocimene;
about 0.01-0.50% eucalyptol;
about 0.01-0.50% isopulegol; and/or
about 0.01-0.50% nerolidol 1.

In an embodiment, the composition is formulated as an oil. In another embodiment, the carrier is selected from the group consisting of linseed oil, olive oil, fish oil, salmon oil, coconut oil, catnip oil and grapeseed oil. In yet another embodiment, the carrier is grapeseed oil.

In an embodiment, the flavoring agent is selected from the group consisting of catnip oil, chicken liver powder, poultry extract, maltodextrin, butter, and bacon. In another embodiment, the flavoring agent is chicken liver powder.

In an embodiment, the composition is formulated as a chew for oral administration. In another embodiment, the chew is produced using cold extrusion. In another embodiment, the weight of the chew is about 0.5-10 g. In yet another embodiment, the weight of the chew is about 4 g, about 6 g, about 9 g, or about 10 g. In still another embodiment, the weight of the chew is about 0.5 g. In an embodiment, the weight of the chew is about 1 g. In another embodiment, the weight of the chew is about 1.5 g. In yet another embodiment, the weight of the chew is about 2 g. In still another embodiment, the weight of the chew is about 3 g. In an embodiment, the weight of the chew is about 4 g. In another embodiment, the weight of the chew is about 5 g. In yet another embodiment, the weight of the chew is about 6 g. In still another embodiment, the weight of the chew is about 7 g. In an embodiment, the weight of the chew is about 8 g. In another embodiment, the weight of the chew is about 9 g. In yet another embodiment, the weight of the chew is about 10 g.

In an embodiment, the 4 g chew comprises:
about 7 mg of cannabidiol;
about 6 mg of cannabidiolic acid;
about 0.12 mg cannabigerolic acid;
about 0.32 mg Δ9-tetrahydrocannabinol; and
about 0.36 mg cannabichromene.

Methods of Treatment

In an aspect, provided herein is a method for treating or reducing pain in a veterinary subject in need thereof, comprising administering to the subject a therapeutically effective amount of any of the compositions or dosage forms described above.

In an embodiment, the pain is associated with arthritis, post-operative pain, acute pain, dental pain, pain associated with gingivitis, or multi-joint pain.

In an embodiment, the pharmaceutical composition or dosage form is administered at a dosage of about 0.1-15.0 mg/kg. In another embodiment, the pharmaceutical composition or dosage form is administered at a dosage of about 0.1-10.0 mg/kg. In yet another embodiment, the pharmaceutical composition or dosage form is administered at a dosage of about 0.1 mg/kg. In still another embodiment, the pharmaceutical composition or dosage form is administered at a dosage of about 0.2 mg/kg. In yet another embodiment, the pharmaceutical composition or dosage form is administered at a dosage of about 0.3 mg/kg. In an embodiment, the pharmaceutical composition or dosage form is administered at a dosage of about 0.4 mg/kg. In another embodiment, the pharmaceutical composition or dosage form is administered at a dosage of about 0.5 mg/kg. In yet another embodiment, the pharmaceutical composition or dosage form is administered at a dosage of about 0.6 mg/kg. In still another embodiment, the pharmaceutical composition or dosage form is administered at a dosage of about 0.7 mg/kg. In yet another embodiment, the pharmaceutical composition or dosage form is administered at a dosage of about 0.8 mg/kg. In an embodiment, the pharmaceutical composition or dosage form is administered at a dosage of about 0.9 mg/kg. In another embodiment, the pharmaceutical composition or dosage form is administered at a dosage of about 1 mg/kg. In yet another embodiment, the pharmaceutical composition or dosage form is administered at a dosage of about 1.5 mg/kg. In still another embodiment, the pharmaceutical composition or dosage form is administered at a dosage of about 2 mg/kg. In an embodiment, the pharmaceutical composition or dosage form is administered at a dosage of about 3 mg/kg. In another embodiment, the pharmaceutical composition or dosage form is administered at a dosage of about 4 mg/kg. In yet another embodiment, the pharmaceutical composition or dosage form is administered at a dosage of about 5 mg/kg. In still another embodiment, the pharmaceutical composition or dosage form is administered at a dosage of about 6 mg/kg. In an embodiment, the pharmaceutical composition or dosage form is administered at a dosage of about 7 mg/kg. In another embodiment, the pharmaceutical composition or dosage form is administered at a dosage of about 8 mg/kg. In yet another embodiment, the pharmaceutical composition or dosage form is administered at a dosage of about 9 mg/kg. In still another embodiment, the pharmaceutical composition or dosage form is administered at a dosage of about 10 mg/kg. In an embodiment, the pharmaceutical composition or dosage form is administered at a dosage of about 11 mg/kg. In another embodiment, the pharmaceutical composition or dosage form is administered at a dosage of about 12 mg/kg. In yet another embodiment, the pharmaceutical composition or dosage form is administered at a dosage of about 13 mg/kg.

In still another embodiment, the pharmaceutical composition or dosage form is administered at a dosage of about 14 mg/kg. In an embodiment, the pharmaceutical composition or dosage form is administered at a dosage of about 15 mg/kg.

In another embodiment, the pharmaceutical composition or dosage form is administered at twice the therapeutically effective dosage for one week, and then subsequently administered at a therapeutically effective dosage. In yet another embodiment, the therapeutically effective dosage is about 0.1-0.5 mg/kg. In still another embodiment, the therapeutically effective dosage is about 2 mg/kg. In an embodiment, the therapeutically effective dosage is about 8 mg/kg.

In an embodiment, the pharmaceutical composition or dosage form is administered at a dosage of about 1 mg/kg for one week, and then subsequently administered at a dosage of about 0.1-0.5 mg/kg. In another embodiment, the pharmaceutical composition or dosage form is administered at a dosage of about 4 mg/kg for one week, and then subsequently administered at a dosage of about 2 mg/kg.

In an embodiment, the pharmaceutical composition or dosage form is administered at a dosage of about 2 mg/kg every 12 hours for two weeks, then subsequently administered at a dosage of about 1 mg/kg every 12 hours for two weeks, and then subsequently administered at a dosage of about 2 mg/kg every 12 hours for four weeks.

In an embodiment, the pharmaceutical composition or dosage form is administered at a dosage of about 1.0 mg/kg once daily. In an embodiment, the pharmaceutical composition or dosage form is administered at a dosage of about 1.0 mg/kg twice daily. In an embodiment, the pharmaceutical composition or dosage form is administered at a dosage of about 1.0 mg/kg three times daily. In an embodiment, the pharmaceutical composition or dosage form is administered at a dosage of about 1.0 mg/kg four times daily.

In an embodiment, the pharmaceutical composition or dosage form is administered at a dosage of about 2.0 mg/kg once daily. In an embodiment, the pharmaceutical composition or dosage form is administered at a dosage of about 2.0 mg/kg twice daily. In an embodiment, the pharmaceutical composition or dosage form is administered at a dosage of about 2.0 mg/kg three times daily. In an embodiment, the pharmaceutical composition or dosage form is administered at a dosage of about 2.0 mg/kg four times daily.

In an embodiment, the pharmaceutical composition or dosage form is administered at a dosage of about 3.0 mg/kg once daily. In an embodiment, the pharmaceutical composition or dosage form is administered at a dosage of about 3.0 mg/kg twice daily. In an embodiment, the pharmaceutical composition or dosage form is administered at a dosage of about 3.0 mg/kg three times daily. In an embodiment, the pharmaceutical composition or dosage form is administered at a dosage of about 3.0 mg/kg four times daily.

In an embodiment, the pharmaceutical composition or dosage form is administered at a dosage of about 4.0 mg/kg once daily. In an embodiment, the pharmaceutical composition or dosage form is administered at a dosage of about 4.0 mg/kg twice daily. In an embodiment, the pharmaceutical composition or dosage form is administered at a dosage of about 4.0 mg/kg three times daily. In an embodiment, the pharmaceutical composition or dosage form is administered at a dosage of about 4.0 mg/kg four times daily. In an embodiment, the pharmaceutical composition or dosage form is administered at a dosage of about 5.0 mg/kg once daily. In an embodiment, the pharmaceutical composition or dosage form is administered at a dosage of about 5.0 mg/kg twice daily. In an embodiment, the pharmaceutical composition or dosage form is administered at a dosage of about 5.0 mg/kg three times daily. In an embodiment, the pharmaceutical composition or dosage form is administered at a dosage of about 5.0 mg/kg four times daily.

In an embodiment, the pharmaceutical composition or dosage form is administered at a dosage of about 6.0 mg/kg once daily. In an embodiment, the pharmaceutical composition or dosage form is administered at a dosage of about 6.0 mg/kg twice daily. In an embodiment, the pharmaceutical composition or dosage form is administered at a dosage of about 6.0 mg/kg three times daily. In an embodiment, the pharmaceutical composition or dosage form is administered at a dosage of about 6.0 mg/kg four times daily.

In an embodiment, the pharmaceutical composition or dosage form is administered at a dosage of about 7.0 mg/kg once daily. In an embodiment, the pharmaceutical composition or dosage form is administered at a dosage of about 7.0 mg/kg twice daily. In an embodiment, the pharmaceutical composition or dosage form is administered at a dosage of about 7.0 mg/kg three times daily. In an embodiment, the pharmaceutical composition or dosage form is administered at a dosage of about 7.0 mg/kg four times daily.

In an embodiment, the pharmaceutical composition or dosage form is administered at a dosage of about 8.0 mg/kg once daily. In an embodiment, the pharmaceutical composition or dosage form is administered at a dosage of about 8.0 mg/kg twice daily. In an embodiment, the pharmaceutical composition or dosage form is administered at a dosage of about 8.0 mg/kg three times daily. In an embodiment, the pharmaceutical composition or dosage form is administered at a dosage of about 8.0 mg/kg four times daily.

In an embodiment, the pharmaceutical composition or dosage form is administered at a dosage of about 9.0 mg/kg once daily. In an embodiment, the pharmaceutical composition or dosage form is administered at a dosage of about 9.0 mg/kg twice daily. In an embodiment, the pharmaceutical composition or dosage form is administered at a dosage of about 9.0 mg/kg three times daily. In an embodiment, the pharmaceutical composition or dosage form is administered at a dosage of about 9.0 mg/kg four times daily.

In an embodiment, the pharmaceutical composition or dosage form is administered at a dosage of about 10.0 mg/kg once daily. In an embodiment, the pharmaceutical composition or dosage form is administered at a dosage of about 10.0 mg/kg twice daily. In an embodiment, the pharmaceutical composition or dosage form is administered at a dosage of about 10.0 mg/kg three times daily. In an embodiment, the pharmaceutical composition or dosage form is administered at a dosage of about 10.0 mg/kg four times daily.

In an embodiment, the method results in a therapeutically effective median maximal serum concentration of cannabidiol. In another embodiment, the median maximal serum concentration of cannabidiol is about 90-310 ng/mL. In yet another embodiment, the median maximal serum concentration of cannabidiol is about 90 ng/mL. In still another embodiment, the median maximal serum concentration of cannabidiol is about 100 ng/mL. In still another embodiment, the median maximal serum concentration of cannabidiol is about 102 ng/mL. In an embodiment, the median maximal serum concentration of cannabidiol is about 200 ng/mL. In another embodiment, the median maximal serum concentration of cannabidiol is about 300 ng/mL. In yet another embodiment, the median maximal serum concentration of cannabidiol is about 400 ng/mL. In still another embodiment, the median maximal serum concentration of cannabidiol is about 500 ng/mL. In an embodiment, the median maximal serum concentration of cannabidiol is about 590 ng/mL. In another embodiment, the median maximal serum concentration of cannabidiol is about 600 ng/mL.

In an embodiment, the veterinary subject is canine, feline, bovine, porcine, or equine. In another embodiment, the veterinary subject is canine. In yet another embodiment, the veterinary subject is feline.

In an aspect, provided herein is a method for treating or reducing pain associated with arthritis, post-operative pain, acute pain, dental pain, pain associated with gingivitis, or multi-joint pain in a veterinary subject in need thereof, comprising administering to the subject a therapeutically effective amount of hemp extract.

In an embodiment, the hemp extract is administered at a dosage of about 0.1-15.0 mg/kg. In another embodiment, the hemp extract is administered at a dosage of about 0.1-10.0 mg/kg. In yet another embodiment, the hemp extract is administered at a dosage of about 0.1 mg/kg. In still another embodiment, the hemp extract is administered at a dosage of about 0.2 mg/kg. In yet another embodiment, the hemp extract is administered at a dosage of about 0.3 mg/kg. In an embodiment, the hemp extract is administered at a dosage of about 0.4 mg/kg. In another embodiment, the hemp extract is administered at a dosage of about 0.5 mg/kg. In yet another embodiment, the hemp extract is administered at a dosage of about 0.6 mg/kg. In still another embodiment, the hemp extract is administered at a dosage of about 0.7 mg/kg. In yet another embodiment, the hemp extract is administered at a dosage of about 0.8 mg/kg. In an embodiment, the hemp extract is administered at a dosage of about 0.9 mg/kg. In another embodiment, the hemp extract is administered at a dosage of about 1 mg/kg. In yet another embodiment, the hemp extract is administered at a dosage of about 1.5 mg/kg. In still another embodiment, the hemp extract is administered at a dosage of about 2 mg/kg. In an embodiment, the hemp extract is administered at a dosage of about 3 mg/kg. In another embodiment, the hemp extract is administered at a dosage of about 4 mg/kg. In yet another embodiment, the hemp extract is administered at a dosage of about 5 mg/kg. In still another embodiment, the hemp extract is administered at a dosage of about 6 mg/kg. In an embodiment, the hemp extract is administered at a dosage of about 7 mg/kg. In another embodiment, the hemp extract is administered at a dosage of about 8 mg/kg. In yet another embodiment, the hemp extract is administered at a dosage of about 9 mg/kg. In still another embodiment, the hemp extract is administered at a dosage of about 10 mg/kg. In an embodiment, the hemp extract is administered at a dosage of about 11 mg/kg. In another embodiment, the hemp extract is administered at a dosage of about 12 mg/kg. In yet another embodiment, the hemp extract is administered at a dosage of about 13 mg/kg. In still another embodiment, the hemp extract is administered at a dosage of about 14 mg/kg. In an embodiment, the hemp extract is administered at a dosage of about 15 mg/kg.

In another embodiment, the hemp extract is administered at twice the therapeutically effective dosage for one week, and then subsequently administered at a therapeutically effective dosage. In yet another embodiment, the therapeutically effective dosage is about 0.1-0.5 mg/kg. In still another embodiment, the therapeutically effective dosage is about 2 mg/kg. In an embodiment, the therapeutically effective dosage is about 8 mg/kg.

In an embodiment, the hemp extract is administered at a dosage of about 1 mg/kg for one week, and then subsequently administered at a dosage of about 0.1-0.5 mg/kg. In another embodiment, the hemp extract is administered at a dosage of about 4 mg/kg for one week, and then subsequently administered at a dosage of about 2 mg/kg.

In an embodiment, the method results in a therapeutically effective median maximal serum concentration of cannabidiol. In another embodiment, the median maximal serum concentration of cannabidiol is about 90-310 ng/mL. In yet another embodiment, the median maximal serum concentration of cannabidiol is about 90 ng/mL. In still another embodiment, the median maximal serum concentration of cannabidiol is about 100 ng/mL. In still another embodiment, the median maximal serum concentration of cannabidiol is about 102 ng/mL. In an embodiment, the median maximal serum concentration of cannabidiol is about 200 ng/mL. In another embodiment, the median maximal serum concentration of cannabidiol is about 300 ng/mL. In yet another embodiment, the median maximal serum concentration of cannabidiol is about 400 ng/mL. In still another embodiment, the median maximal serum concentration of cannabidiol is about 500 ng/mL. In an embodiment, the median maximal serum concentration of cannabidiol is about 590 ng/mL. In another embodiment, the median maximal serum concentration of cannabidiol is about 600 ng/mL.

In an embodiment, the veterinary subject is canine, feline, bovine, porcine, or equine. In another embodiment, the veterinary subject is canine. In yet another embodiment, the veterinary subject is feline.

The pharmaceutical compositions and dosage forms of the present disclosure may be administered by any convenient route, for example, by infusion or bolus injection, by absorption through epithelial or mucocutaneous linings (e.g., oral mucosa, rectal and intestinal mucosa, etc.) and may be administered together with any other therapeutic agent. Administration can be systemic or local.

The therapeutic compositions of the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the weight of a subject to be administered, target disease, conditions, route of administration, and the like. Various delivery systems are known and can be used to administer the pharmaceutical composition of the invention, e.g., encapsulation in liposomes, microparticles, microcapsules, receptor mediated endocytosis (see, e.g., Wu et al. (1987) J. Biol. Chem. 262:4429-4432). Methods of introduction include, but are not limited to, intradermal, intramuscular, intraperitoneal, intravenous, transdermal, buccal, sublingual, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum, methyl cellulose, hydroxypropylmethyl-cellulose, sodium carbomethylcellulose, and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the pharmaceutical composition or dosage form in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active components may be dissolved or suspended in suitable liquids, such as fatty oils, liquid paraffin, or liquid polyethylene glycols.

Alternatively, the composition may be in a powder form for constitution before use with a suitable vehicle, e.g., sterile, pyrogen-free water. The exact formulation, route of administration and dosage may be chosen by the physician familiar with the patient's condition. (See for example Fingl, et al., 1975, in "The Pharmacological Basis of Therapeutics", Chapter I, p. 1). Depending on the severity and responsiveness of the condition treated, dosing can also be a single administration of a slow release composition, with course of treatment lasting from several days to several weeks or until cure is effected or diminution of the disease state is achieved.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, chews, pet food, etc. In certain embodiments, for the dosages provided above, they are administered in one serving of pet food, e.g. 1 mg/kg of hemp extract provided in one serving of pet food.

In accordance with the methods disclosed herein, pharmaceutical formulations can be administered to the patient using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer a pharmaceutical formulation.

In an embodiment for non-human animal administration, the term "pharmaceutical" as used herein may be replaced by "veterinary."

EXAMPLES

Example 1

CBD Oil and Protocols Approval

The industrial hemp strain used in this study was a proprietary hemp strain utilizing ethanol and heat extraction with the final desiccated product reconstituted into an olive oil base containing approximately 10 mg/ml of CBD as an equal mix of CBD and carboxylic acid of CBD (CBDa), 0.24 mg/ml tetrahydrocannabinol (THC), 0.27 mg/ml cannabichromene (CBC), and 0.11 mg/ml cannabigerol (CBG) which is dehydrated; all other cannabinoids were less than 0.01 mg/ml. Analysis of 5 different production runs using a commercial analytical laboratory (MCR Laboratories, Framingham, Mass.) show less than a 9% difference across batches for each of the detected cannabinoids listed above. The study was performed after the Cornell University institutional animal care and use committee (IACUC) approved the study which follows the guidelines for animal use according to the IACUC. Client owned dogs were enrolled after informed consent in accordance with the Declaration of Helsinki.

Example 2

Terpene Profiles

Terpene profiles were examined for four separate oil extractions, prepared as described above. All oils contained 0.09-0.13% α-pinene, 0.23-0.44% β-myrcene, 0.04-0.09% β-pinene, 0.05-0.09% δ-limonene, 0.03-0.06% linalool, 0.04-0.07% β-caryophyllene, 0.02-0.04% α-humulene, 0.04-0.07% nerolidol 2, 0.02-0.04% guaiol, 0.04-0.08% caryophyllene oxide, and 0.01-0.04% α-bisabolol. In addition, some of the oils tested contained 0.02% camphene, 0.02-0.03% β-ocimene, 0.02-0.05% eucalyptol, 0.02% isopulegol, and/or 0.02-0.04% nerolidol 1. Total terpenes ranged from 0.73-1.10%, Example 3

Pharmacokinetics

An initial investigation into single-dose oral pharmacokinetics was performed with 4 beagles (3.5-7 years, male castrated, 10.7-11.9 kg). Each dog received a 2 mg/kg and an 8 mg/kg oral dosage of CBD oil, with a 2-week washout period between each experiment. The dogs were fed two hours after dosing. Physical examination was performed at 0, 4, 8 and 24 hours after dosing. Attitude, behavior, proprioception, and gait were subjectively evaluated at each time point during free running/walking and navigation around standard traffic cones (weaving). Five ml of blood was collected at time 0, 0.5, 1, 2, 4, 8, 12 and 24 hours after oil administration. Blood samples were obtained via jugular venipuncture and transferred to a coagulation tube for 20 minutes. Samples were centrifuged (VWR, Clinical Centrifuge) at 3,600×g for 10 minutes; serum was removed and stored at −80° C. until analysis using liquid chromatography-mass spectrometry (LC-MS) at Colorado State University Core Mass Spectrometry facility.

Example 4

Extraction of CBD from Canine Serum and Mass Spectrometry Analysis

CBD was extracted from canine serum using a combination of protein precipitation and liquid-liquid extraction using n-hexane, with minor modifications for microflow ultra-high pressure liquid chromatography (UHPLC). Briefly, 0.05 ml of canine serum was subjected to protein precipitation in the presence of ice-cold acetonitrile (80% final concentration), spiked with deuterated CBD as the internal standard (0.06 mg/ml, CDB-$d_3$ Cerilliant, Round Rock, Tex., USA). 0.2 ml of water was added to each sample prior to the addition of 1.0 ml of hexane to enhance liquid-liquid phase separation. Hexane extract was removed and concentrated to dryness under laboratory nitrogen. Prior to LC-MS analysis, samples were resuspended in 0.06 mL of 100% acetonitrile. A standard curve using the CBD analytical standard was prepared in canine serum non-exposed to CBD and extracted as above. Cannabidiol concentration in serum was quantified using a chromatographically coupled triple-quadropole mass spectrometer (UHPLC-QQQ-MS).

Example 5

CBD Serum Concentration Data Analysis

From the UHPLC-QQQ-MS data, peak areas were extracted for CBD detected in biological samples and normalized to the peak area of the internal standard CBD-$d_3$, in each sample using Skyline as well as an in-house R Script (www.r-project.org). CBD concentrations were calculated to nanograms per mL of serum as determined by the line of regression of the standard curve ($r2=0.9994$, 0-1000 ng/mL). For this assay, the limits of detection (LOD) and limits of quantification (LOQ) represent the lower limits of detection and quantification for each compound in the matrix of this study. Pharmacokinetic variables were estimated by means of non-compartmental analysis, utilizing a pharmacokinetic software package (PK Solution, version 2.0, Montrose, Colo., USA).

Example 6

Inclusion and Exclusion Criteria for Clinical Trial

The study population consisted of client-owned dogs presenting to Cornell University Hospital for Animals for evaluation and treatment of a lameness due to OA. Dogs were considered for inclusion in the study if they had radiographic evidence of OA, signs of pain according to assessment by their owners, detectable lameness on visual gait assessment and painful joint(s) on palpation. Each dog had an initial complete blood count ([CBC] Bayer Advia 120, Siemens Corp., New York, N.Y., USA) and serum chemistry analysis (Hitachi 911, Roche Diagnostics, Indianapolis, Ind., USA) performed to rule out any underlying disease that might preclude enrolment. Elevations in alkaline phosphatase (ALP), alanine aminotransferase (ALT) and aspartate aminotransferase (AST) were allowed if prior hepatic ultrasound was deemed within normal limits except for potential non-progressive nodules (possible hepatic nodular hyperplasia).

All owners completed a brief questionnaire to define the affected limb(s), duration of lameness, and duration of analgesic or other medications taken.

All dogs underwent radiographic examination of affected joints and a radiologist confirmed the presence or absence of OA, and excluded the presence of concomitant disease that might preclude them from enrolment (i.e. lytic lesions).

During the trial, dogs were only allowed to receive NSAIDs, fish oil, and/or glucosamine/chondroitin sulphate without any change in these medications for 4 weeks prior to or during the 10-week study period as standard of care for the disease process. Other analgesic medications used, such as gabapentin and tramadol, were discontinued at least 2 weeks prior to enrollment. Dogs were excluded if they had evidence of renal, uncontrolled endocrine, neurologic, or neoplastic disease, or if they had a temperament not suited for gaiting on a lead or were undergoing physical therapy. Every dog was fed its regular diet with no change allowed during the trial.

Example 7

Clinical Trial

The study was a placebo-controlled, double-blind, crossover clinical trial. Dogs received each of two treatments in random order (Randomizer iPhone Application): CBD, 2 mg/kg every 12 hours, or placebo (an equivalent volume of olive oil with 10 parts per thousands of anise oil and 5 parts per thousands of peppermint oil to provide a similar herbal smell) every 12 hours. Each treatment was administered for 4 weeks with a 2-week washout period in between treatments. Blood was collected to repeat complete blood counts and chemistry analysis at weeks 2 and 4 for each treatment.

At each visit, each dog was evaluated by a veterinarian based on a scoring system, as well as by its owner (canine brief pain inventory [CBPI], Hudson activity scale) before treatment initiation and at weeks 2 and 4 thereafter.

Example 8

Statistical Analysis

Initial power analysis was performed to assess number of dogs needed for this study as a cross over design with a power set 0.80 and alpha of 0.05 using prior data suggesting a baseline CBPI or Hudson score change of approximately 15 points (two tailed) with a standard deviation of 20. When calculated it was assumed that 14 dogs would be necessary to find significance.

Statistical analysis was performed with a commercially available software package (JMP 12.0, Cary, N.C., USA). All data was assessed utilizing a Shapiro-Wilks test for normality. Considering a majority of our blood, serum and scoring data was normally distributed a mixed model analysis of variance was used. Cross-over study variables included in the model were: fixed effects of treatment, time, sequence of oil, gender, age, NSAID usage, treatment x time; as well as random effects of observation period, period nested within dog, time point nested within period nested within dog. To control for difference and relative change in CBPI pain and activity interference assessments and Hudson scoring across dogs, the fixed effect of initial CPBI or Hudson Score was also included for these analyses. Dunnett's tests were performed post hoc on any significant effects of time x treatment to assess differences with week 0 of CBD oil or placebo oil as the baseline time point for comparison. A p value of less than 0.05 was determined to be significant for all analyses.

Example 9

Pharmacokinetic Results

Figure 2:
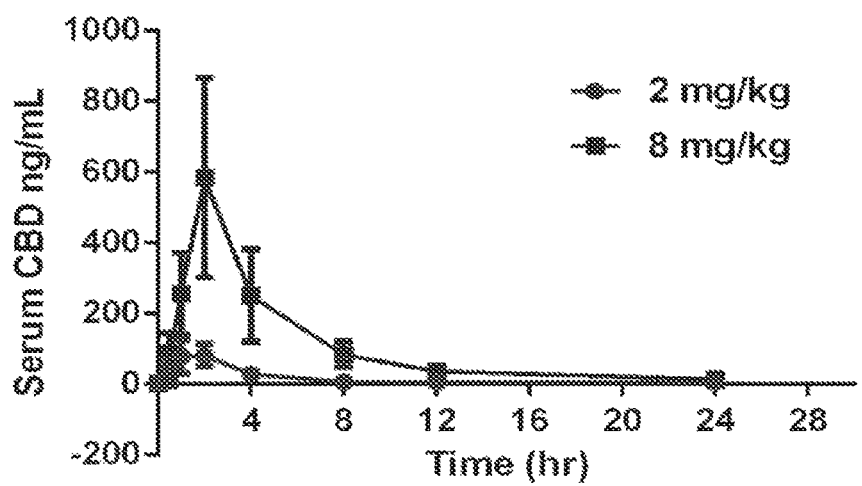
FIG. 2: Serum concentration (ng/mL) of 2 mg/kg and 8 mg/kg oral dosage of CBD oil in time (min)

Pharmacokinetics demonstrated that CBD half-life of elimination median was 4.2 hours (3.8-6.8 hours) with the 2 mg/kg dose, and 4.2 hours (3.8-4.8 hours) with the 8 mg/kg dose (Table 1). Median maximal concentration of CBD oil (FIG. 2) was 102.3 mg/ml (60.7-132.0 ng/mL; 180 nM) and 590.8 ng/mL (389.5-904.5 ng/mL; 1.2 uM) and was reached after 1.5 hours and 2 hours, respectively, for 2 and 8 mg/kg doses. No obvious psychoactive properties were observed on evaluation at any time point during the 2 and 8 mg/kg doses over 24 hours. These results led to a practical dosing during the clinical trial of 2 mg/kg body weight every 12 hours.

TABLE 1

Serum pharmacokinetic of 2 mg/kg and 8 mg/kg oral dosage of CBD oil medians and ranges after 2 mg/kg and 8 mg/kg single oral dosing

|  | Cmax (ng/ml) | Tmax (h) | T½ elim (h) | AUC 0-t (ng-hr/ml) | MRT (h) |
| --- | --- | --- | --- | --- | --- |
| Dose (2 mg/kg) | | | | | |
| Dog 1 | 60.7 | 1 | 4.4 | 183 | 6 |
| Dog 2 | 132 | 1 | 3.9 | 351 | 4.2 |
| Dog 3 | 102.7 | 2 | 3.8 | 382 | 5.1 |
| Dog 4 | 101.9 | 2 | 6.8 | 437 | 9.1 |
| Median | 102.3 | 1.5 | 4.2 | 367.2 | 5.6 |
| (Range) | (60.7-132.0) | (1.0-2.0) | (3.8-6.8) | (183.5-437.4) | (4.2-9.1) |
| Dose (8 mg/kg) | | | | | |
| Dog 1 | 499 | 2 | 3.8 | 2928 | 5.7 |
| Dog 2 | 389 | 1 | 4.8 | 1753 | 7 |
| Dog 3 | 904 | 2 | 4.2 | 3048 | 5.1 |
| Dog 4 | 682 | 2 | 4.1 | 2389 | 5.2 |
| Median | 590.8 | 2.0 | 4.2 | 2658.6 | 5.6 |
| (Range) | (389.5-904.5) | (1.0-2.0) | (3.8-4.8) | (1753.6-3048.6) | (5.1-7.0) |

Legend: Cmax = maximum concentration; Tmax = time of maximum concentration; T½ el = half-life of elimination; AUC 0-t = area under the curve (time 0 to 24h); MRT = median residence time.

Example 10

Dogs Included in Clinical Trial

Twenty-two client-owned dogs with clinically and radiographically confirmed evidence of osteoarthritis were recruited. Sixteen of these dogs completed the trial and were included in the analyses; their breed, weight, age, sex, worse affected limb, radiographic findings, use of NSAIDs and sequence of treatments are summarized in Table 2. Dogs were removed due to osteosarcoma at the time of enrolment, gastric torsion (placebo), prior aggression issues (CBD oil), pyelonephritis/kidney insufficiency (CBD oil), recurrent pododermatitis (placebo oil), and diarrhea (placebo oil).

TABLE 2

Characteristics (breed, weight, age, sex, affected limbs, radiographic findings, concomitant utilization of NSAID and sequence of treatment) of the dogs included in this study.

| Breed | Weight (kg) | Age (years) | Sex | Worse limb | Radiographic Findings and OA localization | NSAID |
| --- | --- | --- | --- | --- | --- | --- |
| Rottweiler | 35.31 | 10 | FS | | Moderate, intracapsular swelling with moderate osteophytosis, left stifle | Carprofen (2.1 mg/kg BID) |
| Mix | 30.6 | 13 | MC | RF | Moderate-to-severe, right-shoulder osteoarthrosis; mild, left-shoulder | No |

TABLE 2-continued

Characteristics (breed, weight, age, sex, affected limbs, radiographic findings, concomitant utilization of NSAID and sequence of treatment) of the dogs included in this study.

| Breed | Weight (kg) | Age (years) | Sex | Worse limb | Radiographic Findings and OA localization | NSAID |
|---|---|---|---|---|---|---|
| | | | | | osteoarthrosis<br>Moderate-to-severe, bilateral hip osteoarthrosis | |
| Mix | 27.2 | 9 | FS | LF | Moderate medial coronoid remodeling (with fragmentation on the right) and bilateral elbow osteoarthrosis | No |
| Mix | 30.5 | 14 | MC | | Moderate enthesopathies on right carpus; mild, left-antebrachiocarpal osteoarthrosis<br>Bilateral moderate coxofemoral osteoarthrosis | No |
| Mix | 23.5 | 10 | FS | | Moderate bilateral stifle osteoarthrosis and moderate intracapsular swelling | Carprofen (2.2 mg/kg) |
| Mix | 28.1 | 10 | FS | LF | Moderate bilateral elbow osteoarthrosis<br>Moderate left-stifle osteoarthrosis with intracapsular swelling | Metacam (0.1 mg/kg) |
| English Bulldog | 25.2 | 8 | MC | LF | Severe osteoarthrosis, left elbow<br>Moderate intracapsular swelling and mild osteoarthrosis, right stifle | Vetprofen (2.0 mg/kg BID) |
| German Shorthaired Pointer | 21.5 | 14 | FS | RH | Moderate bilateral elbow osteoarthrosis | Carprofen (2.4 mg/kg BID) |
| Labrador Retriever | 26.1 | 13 | FS | | Bilateral severe stifle osteoarthrosis due to cranial cruciate ligament disease | Metacam (0.1 mg/kg SID) |
| Mix | 18.2 | 13 | FS | RF | Bilateral moderate elbow osteoarthrosis and medial epicondylitis | Metacam (0.1 mg/kg SID) |
| Mix | 22 | 9 | FS | RH | Moderate, stifle osteoarthrosis with moderate intracapsular swelling | No |
| Bernese Mountain Dog | 50 | 3 | M | RF | Bilateral severe elbow osteoarthritis, medial coronoid disease, and medial epicondylitis | Carprofen (20.0 mg/kg SID) |
| Belgian Malinois | 25.1 | 9 | FS | RF | Severe bilateral elbow osteoarthrosis<br>Bilateral moderate hip osteoarthrosis | Carprofen (2 mg/kg BID) |
| Mix | 28.6 | 13 | FS | | Severe bilateral elbow osteoarthritis<br>Severe bilateral hip osteoarthritis | No |
| Border Collie | 22 | 14 | MC | | Severe thoracolumbosacral osteophytosis<br>Multifocal carpal enthesiophytes | No |
| Beagle | 17.6 | 5 | MC | | Mild left elbow osteoarthrosis, with possible medial coronoid disease<br>Moderate-to-severe bilateral stifle osteoarthrosis | No |

Example 11

Clinical Trial Results

Figure 3A:
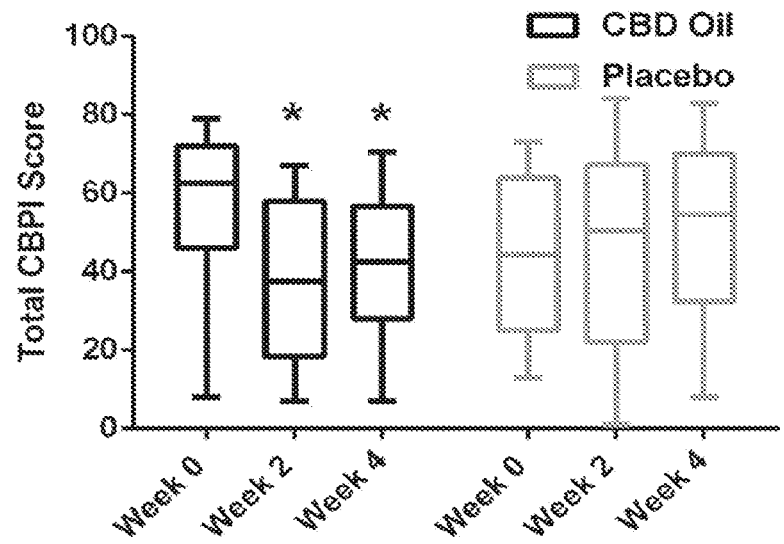
FIG. 3A: Box-and-whisker plot of total CBPI score at each time for treatment and placebo oils. Box represents the mean and 25th and 75th percentile and the whiskers represent the 99th and 1st percentiles.
Figure 3B:
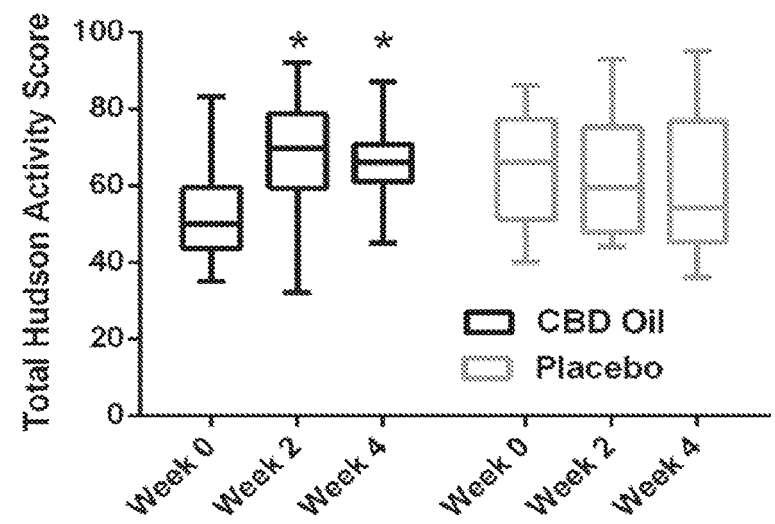
FIG. 3B: Box-and-whisker plot of total Hudson score at each time for treatment and placebo oils. Box represents the mean and 25th and 75th percentile and the whiskers represent the 99th and 1st percentiles.
Figure 4:
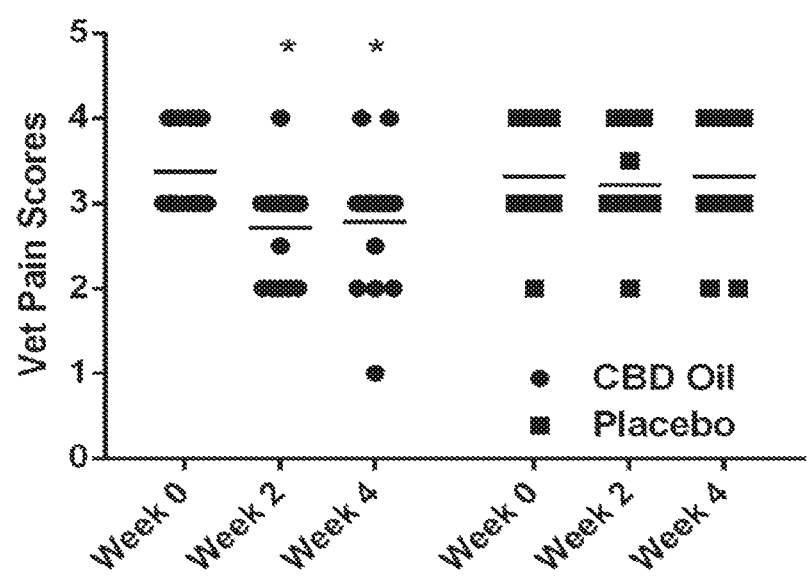
FIG. 4: Box-and-whisker plot of total vet pain assessment at each time for treatment and placebo oils.
Figure 5A:
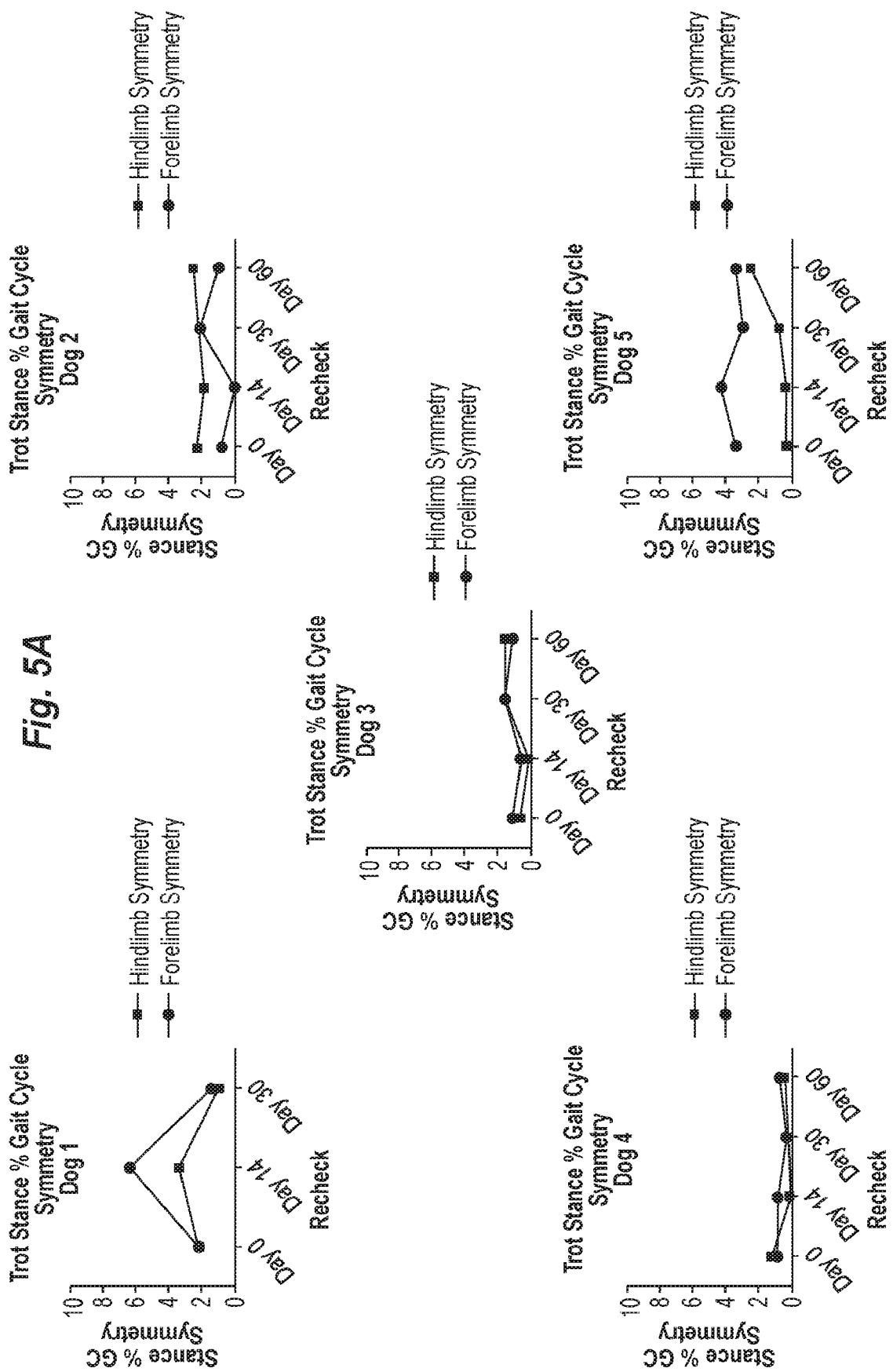
Figure 5B:
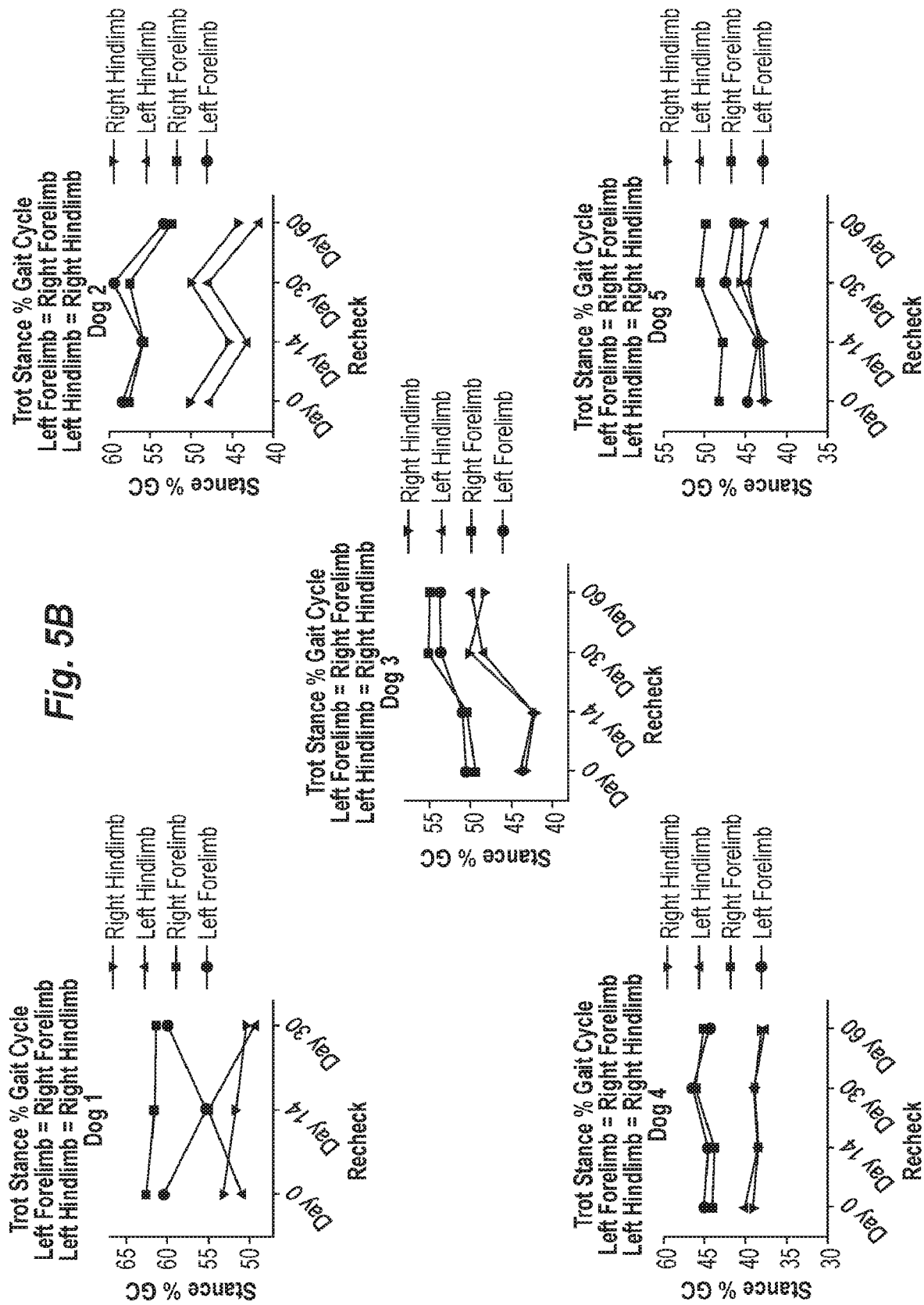
Figure 5D:
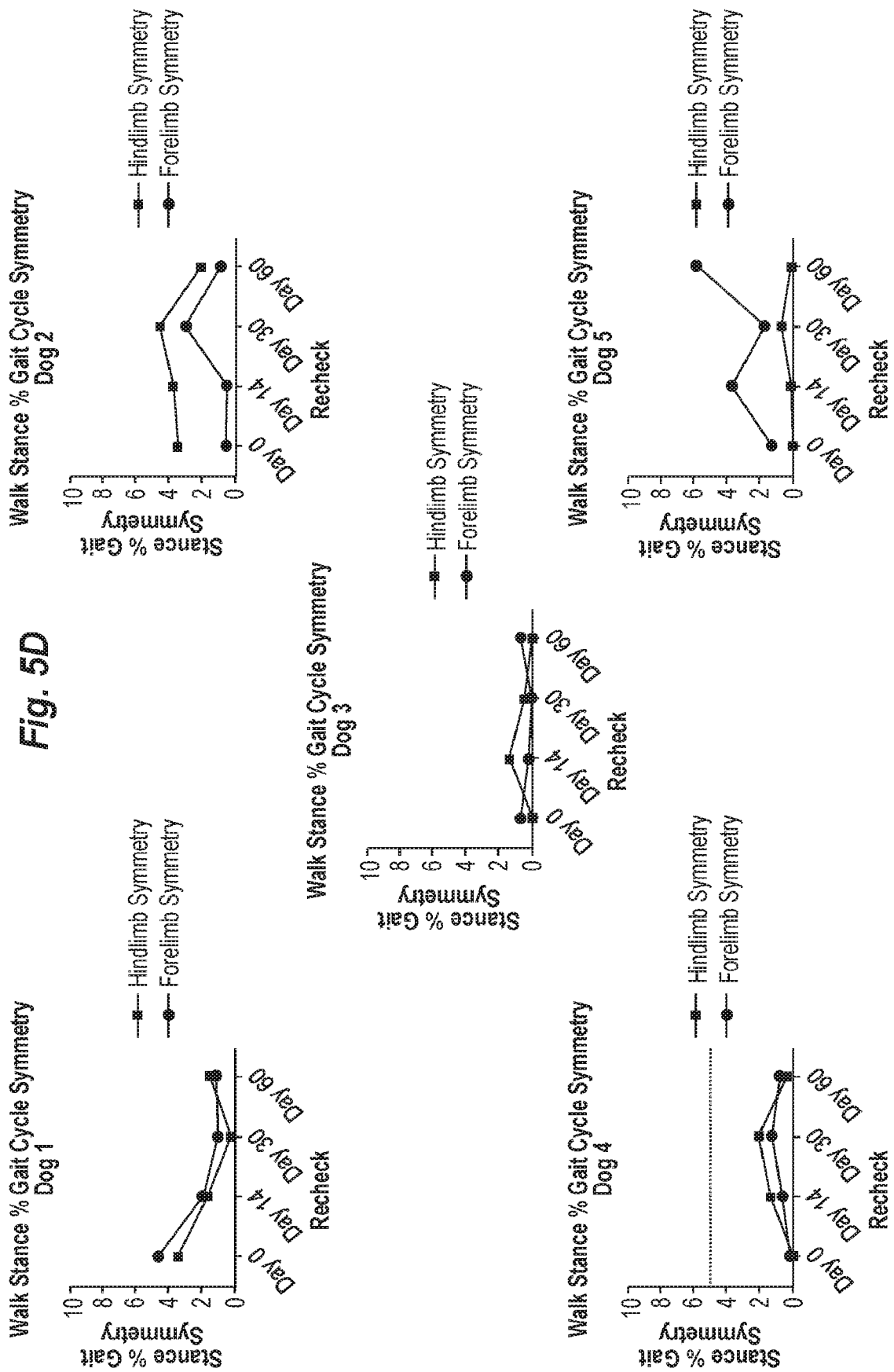
Figure 5E:
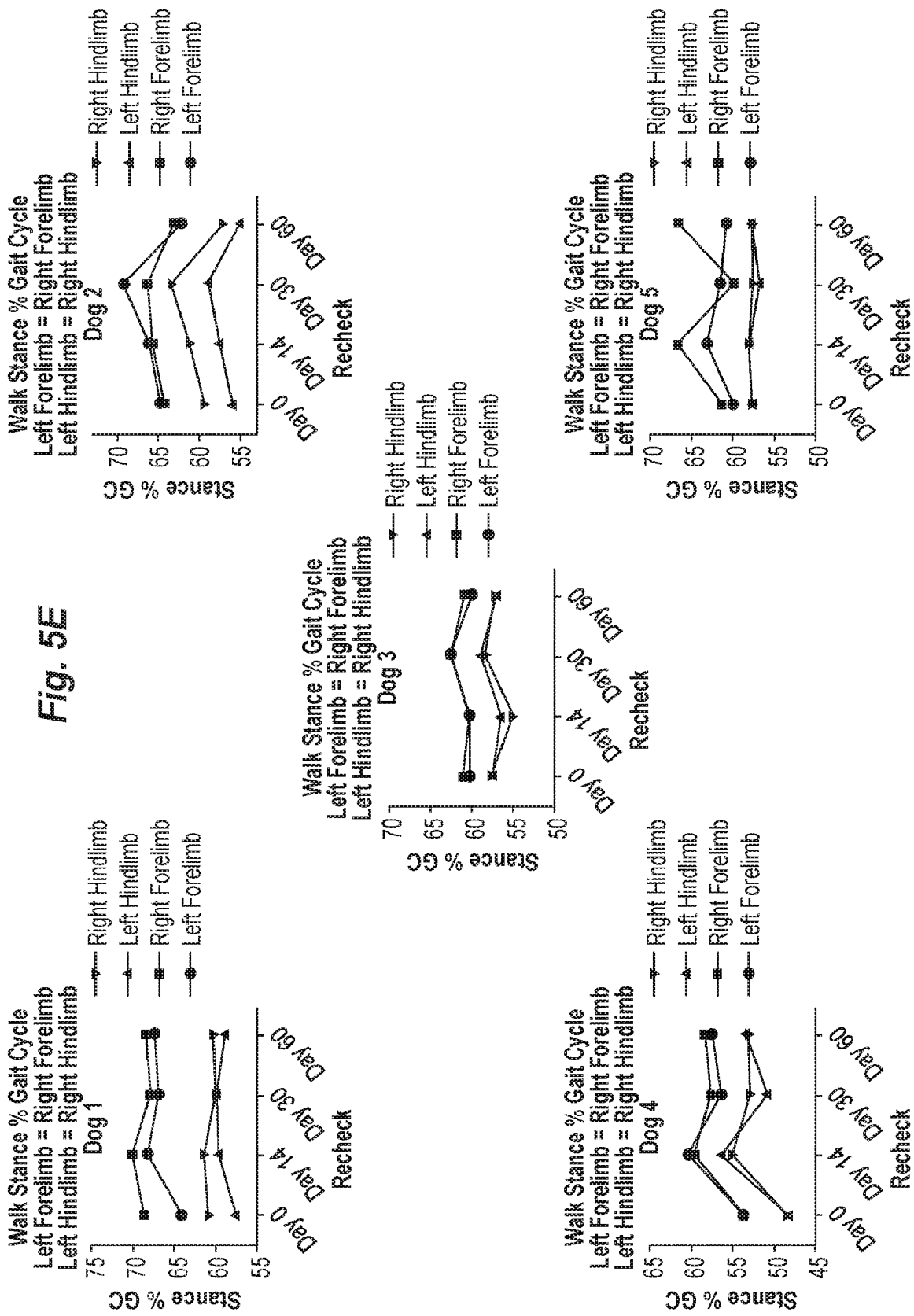

CBPI and Hudson scores (FIG. 3A and FIG. 3B) showed a significant decrease in pain and increase in activity ($p<0.01$) at week 2 and 4 during CBD treatment when compared to baseline week 0, while placebo treatment showed no difference in CBPI and Hudson scoring from scores prior to initiation of treatments (Table 3). Lameness as assessed by veterinarians (FIG. 4) showed an increase in lameness with age ($p<0.01$), whereas NSAID use ($p=0.03$) results in significantly less lameness. Veterinary pain scores showed significantly less pain in dogs on NSAIDs ($p<0.01$). CBD oil resulted in significantly less pain when compared to baseline on evaluation at both week 2 and week 4 ($p<0.03$), while 24 placebo treatment showed no significant differences. No changes were observed in weight-bearing capacity when evaluated utilizing the veterinary lameness and pain scoring system (Table 3).

TABLE 3

Average and standard deviation for CBPI and Hudson; median and range for lameness, weight-bearing and pain scores at each time for treatment and placebo oils

| | Treatment A/CBD oil | | | Treatment B placebo oil | | |
|---|---|---|---|---|---|---|
| | Week 0 | Week 2 | Week 4 | Week 0 | Week 2 | Week 4 |
| CBPI Pain (0-40) | 21 ± 8 | 14 ± 6* | 14 ± 8* | 17 ± 7 | 19 ± 9 | 19 ± 9 |
| CBPI Interference (0-60) | 35 ± 15 | 25 ± 15* | 26 ± 14* | 27 ± 15 | 29 ± 15 | 31 ± 16 |
| Hudson (0-110) | 54 ± 13 | 67 ± 15* | 67 ± 10* | 65 ± 14 | 64 ± 16 | 60 ± 19 |
| Veterinary lameness§ | 3 (1-4) | 3 (1-2) | 3 (1-4) | 3 (2-4) | 3(2-4) | 3 (1-4) |

TABLE 3-continued

Average and standard deviation for CBPI and Hudson; median and range for lameness, weight-bearing and pain scores at each time for treatment and placebo oils

|  | Treatment A/CBD oil | | | Treatment B placebo oil | | |
|---|---|---|---|---|---|---|
|  | Week 0 | Week 2 | Week 4 | Week 0 | Week 2 | Week 4 |
| Veterinary pain ƒ | 3 (3-4) | 3 (2-4)* | 3 (1-4)* | 3 (2-4) | 3 (2-4) | 3 (2-4) |
| Veterinary weight-bearing⸓ | 2 (1-3) | 2 (1-3) | 2 (1-3) | 2 (1-3) | 2 (1-3) | 2 (1-3) |

Legend:
Asterisk (*) represents significant difference (p < 0.05) from baseline week 0 of CBD treatment.
§Lameness was scored as follows: 1 = no lameness observed/walks normally, 2 = slightly lame when walking, 3 = moderately lame when walking, 4 = severely lame when walking, 5 = reluctant to rise and will not walk more than 5 paces.
ƒ Pain on palpation was scored as follows: 1 = none, 2 = mild signs, dog turns head in recognition, 3 = moderate signs, dog pulls limb away, 4 = severe signs, dog vocalizes or becomes aggressive, 5 = dog will not allow palpation.
⸓ Weight-bearing was scored as follows: 1 = equal on all limbs standing and walking, 2 = normal standing, favors affected limb when walking, 3 = partial weight-bearing standing and walking, 4 = partial weight-bearing standing, non-weight-bearing walking, 5 = non-weight-bearing standing and walking.

Chemistry analysis and CBC were performed at each visit. No significant change in the measured CBC values was noted in either the CBD oil or placebo treated dogs (data not shown). Serum chemistry values were not different between placebo compared to CBD oil (Table 4), except for alkaline phosphatase (ALP) which significantly increased over time from baseline by week 4 of CBD oil treatment (p=0.005); with nine of the sixteen dogs showing increases over time (FIG. 1). Glucose was increased in dogs receiving the placebo oil at each time point (p=0.04) and creatinine levels increased over time in both dogs receiving CBD oil and those receiving placebo oil (p<0.01); though all values remained within reference ranges. Other notable significances in serum chemistry values were associated with primarily age or NSAID use. An increase in age was associated with significantly higher blood urea nitrogen (BUN; p<0.001), calcium (p=0.014), phosphorus (p=0.001), alanine aminotransferase (ALT; p=0.028), ALP (p=0.012), gamma glutamyltransferase (GGT; p=0.018), globulin (p=0.021) and cholesterol (p=0.002) values. NSAID use was associated with significantly higher BUN (p=0.003), and creatinine (p=0.017), and significant decreases in total protein (p<0.001) and serum globulin (p<0.001).

TABLE 4

Mean ± SD values for serum chemistry data obtained at each time point for dogs receiving CBD and placebo oils

|  | Reference | Treatment A/CBD oil | | | Treatment B/placebo oil | | |
|---|---|---|---|---|---|---|---|
|  |  | Week 0 | Week 2 | Week 4 | Week 0 | Week 2 | Week 4 |
| Na | 145-153 mEq/L | 149 ± 3 | 149 ± 2 | 149 ± 1 | 149 ± 1 | 149 ± 2 | 149 ± 2 |
| K | 4.1-5.6 mEq/L | 4.9 ± 0.3 | 4.9 ± 0.5 | 4.9 ± 0.3 | 4.8 ± 0.4 | 4.9 ± 0.4 | 4.9 ± 0.3 |
| Cl | 105-116 mEq/L | 110 ± 3 | 109 ± 3 | 109 ± 2 | 110 ± 2 | 110 ± 2 | 110 ± 2 |
| BUN | 10-32 mg/dL | 20 ± 9 | 20 ± 7 | 20 ± 6 | 19 ± 6 | 21 ± 7 | 19 ± 6 |
| Creat | 0.64.4 mg/dL | 1.0 ± 0.3 | 1.1 ± 0.3* | 1.0 ± 0.3* | 0.9 ± 0.3 | 1.0 ± 0.3* | 1.0 ± 0.3* |
| Ca | 9.3-11.4 mg/dL | 10.4 ± 0.5 | 10.4 ± 0.4 | 10.3 ± 0.4 | 10.4 ± 0.6 | 10.4 ± 0.4 | 10.4 ± 0.4 |
| P | 2.9-5.2 mg/dL | 3.8 ± 0.8 | 3.9 ± 0.8 | 3.9 ± 0.6 | 4.0 ± 0.7 | 3.9 ± 0.6 | 4.0 ± 0.5 |
| Mg | 1.4-2.2 mg/dL | 1.8 ± 0.2 | 1.8 ± 0.2 | 1.8 ± 0.2 | 1.8 ± 0.1 | 1.8 ± 0.1 | 1.8 ± 0.1 |
| GLU | 63-118 mg/dL | 92 ± 9 | 89 ± 9 | 92 ± 9 | 97 ± 10* | 93 ± 8 | 97 ± 10* |
| ALT | 20-98 U/L | 93 ± 86 | 93 ± 88 | 114 ± 119 | 90 ± 98 | 222 ± 606 | 166 ± 284 |
| AST | 14-51 U/L | 31 ± 8 | 33 ± 13 | 34 ± 16 | 30 ± 8 | 56 ± 99 | 45 ± 34 |
| ALP | 17411 U/L | 160 ± 212 | 238 ± 268 | 323 ± 407* | 204 ± 287 | 186 ± 287 | 175 ± 248 |
| GGT | 0-6 U/L | 4 ± 3 | 3 ± 2 | 3 ± 2 | 3 ± 2 | 4 ± 6 | 5 ± 4 |
| TB | 0.0-0.2 mg/dL | 0.1 ± 0.1 | 0.0 ± 0.1 | 0.1 ± 0.1 | 0.0 ± 0.1 | 0.0 ± 0.1 | 0.0 ± 0.1 |
| TP | 5.3-7.0 g/dL | 6.3 ± 0.4 | 6.4 ± 0.5 | 6.3 ± 0.4 | 6.3 ± 0.4 | 6.3 ± 0.4 | 6.3 ± 0.4 |
| ALB | 3.14.2 g/dL | 3.7 ± 0.2 | 3.7 ± 0.2 | 3.7 ± 0.2 | 3.7 ± 0.2 | 3.7 ± 0.2 | 3.7 ± 0.2 |
| GLOB | 1.9-3.6 g/dL | 2.6 ± 0.3 | 2.6 ± 0.4 | 2.6 ± 0.4 | 2.6 ± 0.4 | 2.6 ± 0.4 | 2.6 ± 0.4 |
| CHOL | 138-332 mg/dL | 291 ± 64 | 301 ± 62 | 302 ± 62 | 295 ± 71 | 300 ± 71 | 308 ± 83 |
| CK | 48-260 U/L | 148 ± 81 | 147 ± 59 | 134 ± 61 | 139 ± 57 | 158 ± 80 | 168 ± 105 |

Legend:
Asterisk (*) indicates significantly different (p < 0.05) serum concentration from baseline week 0 CBD treatment.

Example 12

Canine Safety Study

A 12-week safety study was performed in canines to evaluate the safety of a soft chew containing CBD.

Animals and Study Design

Eight purebred beagle dogs, 11 months-5 years old, weighing 7.39-11.95 kg at study start were selected for the study, as shown in Table 5.

TABLE 5

Animal information

| Dog ID | Sex | Date of Birth |
|---|---|---|
| 13536 | F | Dec. 24, 2013 |
| 2753822 | F | Jan. 4, 2015 |
| 2808987 | F | Mar. 8, 2015 |
| 13644 | M | Feb. 7, 2017 |
| 2784123 | M | Feb. 8, 2015 |
| 2963028 | M | Sep. 12, 2015 |
| 13513 | F | Jul. 31, 2013 |
| 13490 | M | Nov. 1, 2012 |

Dogs were single housed in cages of a size in accordance with the Animal Welfare Act, with a 12-hour-light/12-hour-dark cycle and targeted conditions of 50° to 85° F. Cages and food bowls were cleaned daily and sanitized in accordance with the Animal Welfare Act. Fresh tap water, fit for human consumption, was available ad libitum by means of an automatic watering system. There were no known contaminants that were reasonably expected to be present in the dietary material that were known to be capable of interfering with the purpose or conduct of the study.

During the study, the control diet, Purina Dog Chow, was the sole source of food supplied to each animal once daily for approximately 1 hour. Dogs were fed according to ideal body condition and fasted for a minimum of 12 hours prior to blood collections. CBD was administered by a soft chew offered twice daily at the approximate dosage of 2 mg/kg. Dosing is shown in Table 6.

CBC and Serum Chemistry

Prior to study initiation, 5 milliliters of blood was collected for each dog and was used to determine eligibility for the study. During the study, 5 milliliters of blood was collected weekly (±2 days). Blood was collected via jugular venipuncture in sterile syringes. Samples were split into two tubes: a red-top serum separator tube and a lavender-top EDTA tube. Red-top tubes were spun in a refrigerated centrifuge for 15 minutes at 3000 RPM after being allowed to clot. Lavender-top tubes were placed on a rocker to allow the blood to adequately mix with the anticoagulant. Blood samples were packaged and sent by priority-overnight to Antech Diagnostics for analysis.

Pharmacokinetic (PK) Blood Collection

On the first day of dosing, blood was collected for a PK analysis from 6 of the 8 dogs. The most cooperative dogs were selected for the PK analysis. Approximately 6 milliliters of blood was collected via jugular venipuncture in sterile syringes at 0 min, 30 min, 60 min, 2 hrs, 4 hrs, 8 hrs, 12 hrs, and 24 hrs after treatment. Samples were placed into red top clotting tubes with no serum separator. Serum was harvested by centrifuging the tubes at 3000 RPM for 15 minutes. The harvested serum was placed in cyrovials and stored at −70° C. Each tube was labeled with the dog id, date of collection, and collection time point. Samples were shipped overnight on dry ice to the Proteomics & Metabolomics Facility at the Colorado State University.

Clinical Observations

A veterinarian performed a complete physical examination of all dogs prior to the initiation of the study and at study completion. Each dog was evaluated as to general health, body and hair coat condition. Qualified personnel performed clinical observations twice daily in accordance with Summit Ridge Farms' Program of Veterinary Care and SOP VC-003 (Rounds Observations). All animals were evaluated twice daily with reference to SOP VC-016 (Recognizing Pain, Stress and/or Distress). Clinical laboratory diagnostic procedures were performed as needed. Veterinary care was given as appropriate to each individual animal in accordance with the Program of Veterinary Care.

TABLE 6

Quantity of chews offered per week

| | | Week | | | | | |
|---|---|---|---|---|---|---|---|
| Dog ID | Sex | 1 | 2 | 3 | 4 | 5 | 6 |
| 13536 | F | 2 small | 1 large, 1 small | 1 large, 1 small | 1 large, 1 small | 1 large, 1 small | 1 large, 1 small |
| 2753822 | F | 1 large | 1 large | 1 large | 1 large | 1 large | 1 large |
| 2808987 | F | 2 small | 2 small | 2 small | 2 small | 1 large, ½ small | 1 large, ½ small |
| 13644 | M | 1 large, ½ small | 1 large, ½ small | 1 large, ½ small | 1 large, ½ small | 1 large, ½ small | 1 large, ½ small |
| 2784123 | M | 1 large, ½ small | 1 large, ½ small | 1 large, ½ small | 1 large, ½ small | 1 large, ½ small | 1 large, ½ small |
| 2963028 | M | 1 large, ½ small | 1 large, ½ small | 1 large, ½ small | 1 large, ½ small | 1 large, ½ small | 1 large, ½ small |
| 13513 | F | 1 large, ½ small | 1 large, ½ small | 1 large, ½ small | 1 large, ½ small | 1 large, ½ small | 1 large, ½ small |
| 13490 | M | 2 small | 2 small | 2 small | 1 large, ½ small | 1 large, ½ small | 1 large, ½ small |

| | | Week | | | | | |
|---|---|---|---|---|---|---|---|
| Dog ID | Sex | 7 | 8 | 9 | 10 | 11 | 12 |
| 13536 | F | 1 large, 1 small | 1 large, 1 small | 1 large, 1 small | 1 large, 1 small | 1 large, 1 small | 1 large, 1 small |
| 2753822 | F | 1 large | 1 large | 1 large | 1 large | 1 large | 1 large |
| 2808987 | F | 1 large, ½ small | 1 large, ½ small | 1 large, ½ small | 1 large, ½ small | 1 large, ½ small | 1 large, ½ small |
| 13644 | M | 1 large, ½ small | 1 large, ½ small | 1 large, ½ small | 1 large, ½ small | 1 large, ½ small | 1 large, ½ small |
| 2784123 | M | 1 large, ½ small | 1 large, ½ small | 1 large, ½ small | 1 large, ½ small | 1 large, ½ small | 1 large, ½ small |
| 2963028 | M | 1 large, ½ small | 1 large, ½ small | 1 large, ½ small | 1 large, ½ small | 1 large, ½ small | 1 large, ½ small |
| 13513 | F | 1 large, ½ small | 1 large, ½ small | 1 large, ½ small | 1 large, ½ small | 1 large, ½ small | 1 large, ½ small |
| 13490 | M | 1 large, ½ small | 1 large, ½ small | 1 large, ½ small | 1 large, ½ small | 1 large, ½ small | 2 small |

Blood Analysis

Blood was analyzed for white blood cell count, red blood cell count, hemoglobin, hematocrit, MCV, MCHC, MCH, and platelet count along with a complete differential. In addition, a 22-test chemistry screen was performed consisting of Glucose, Urea Nitrogen, Creatinine, Total Protein, Albumin, Total Bilirubin, Alkaline Phosphatase, ALT, AST, CPK, Cholesterol, Calcium, Phosphorus, Sodium, Potassium, Chloride, A/G Ratio, BUN/Creatinine Ratio, Globulin, Triglycerides, GGTP and Magnesium. Measurements were taken prior to the start of the study and then weekly during the course of the study.

PK Analysis

Analysis of the blood level values and pharmacokinetics of the test article were performed.

Results

Body Weight

The mean average weight change for dogs during the 12 weeks of the study was −0.04 kg (−0.43%). Weight data is presented in Tables 7 and 8.

TABLE 7

Weekly body weights (weeks 1-6)

| Dog ID | Sex | Base | Week 1 | 2 | 3 | 4 | 6 |
|---|---|---|---|---|---|---|---|
| 13536 | F | 11.95 | 12.34 | 11.95 | 12.10 | 12.05 | 12.08 | 12.04 |
| 2753822 | F | 7.39 | 7.24 | 7.18 | 7.16 | 7.03 | 6.99 | 7.03 |
| 2808987 | F | 10.40 | 10.40 | 10.36 | 10.23 | 10.16 | 10.21 | 10.20 |
| 13644 | M | 8.92 | 9.25 | 9.56 | 9.65 | 9.63 | 9.50 | 9.64 |
| 2784123 | M | 9.21 | 8.93 | 9.07 | 9.27 | 9.18 | 9.13 | 9.33 |
| 2963028 | M | 9.28 | 9.15 | 9.13 | 8.98 | 9.07 | 9.32 | 9.28 |
| 13513 | F | 9.67 | 9.58 | 9.52 | 9.16 | 9.10 | 9.14 | 8.78 |
| 13490 | M | 10.58 | 10.64 | 10.45 | 10.39 | 10.27 | 10.39 | 10.28 |
| | Mean: | 9.68 | 9.69 | 9.65 | 9.62 | 9.56 | 9.60 | 9.57 |
| | SD: | 1.346 | 1.488 | 1.371 | 1.410 | 1.418 | 1.438 | 1.425 |

*Note: Table 7 has columns Base, 1, 2, 3, 4, 6 under "Week"*

TABLE 8

Weekly body weights (weeks 7-12)

| Dog ID | Sex | 7 | 8 | 9 | 10 | 11 | 12 | Chg. | % Chg. |
|---|---|---|---|---|---|---|---|---|---|
| 13536 | F | 12.09 | 11.99 | 12.04 | 12.09 | 12.10 | 11.97 | 0.02 | 0.17 |
| 2753822 | F | 7.17 | 7.04 | 7.23 | 7.41 | 7.28 | 7.34 | −0.05 | −0.68 |
| 2808987 | F | 10.32 | 9.98 | 9.90 | 9.98 | 9.95 | 10.15 | −0.25 | −2.40 |
| 13644 | M | 9.53 | 9.49 | 9.28 | 9.42 | 9.28 | 9.12 | 0.20 | 2.24 |
| 2784123 | M | 9.46 | 9.58 | 9.47 | 9.67 | 9.39 | 9.18 | −0.03 | −0.33 |
| 2963028 | M | 9.32 | 9.26 | 9.23 | 9.51 | 9.66 | 9.55 | 0.27 | 2.91 |
| 13513 | F | 9.09 | 9.58 | 9.15 | 8.88 | 8.81 | 8.89 | −0.78 | −8.07 |
| 13490 | M | 10.42 | 11.06 | 10.98 | 10.90 | 11.06 | 10.87 | 0.29 | 2.74 |
| | Mean: | 9.68 | 9.75 | 9.66 | 9.73 | 9.69 | 9.63 | −0.04 | −0.43 |
| | SD: | 1.395 | 1.439 | 1.414 | 1.376 | 1.444 | 1.391 | 0.350 | 3.605 |

Food Consumption

The mean daily food consumption per week for dogs during the study was 204 g. Food consumption data is presented in Tables 9 and 10.

TABLE 9

Average daily food consumption per week (weeks 1-6)

| Dog ID | Sex | 1 | 2 | 3 | 4 | 5 | 6 |
|---|---|---|---|---|---|---|---|
| 13536 | F | 250 | 207 | 200 | 200 | 200 | 177 |
| 2753822 | F | 144 | 162 | 176 | 157 | 154 | 186 |
| 2808987 | F | 203 | 223 | 212 | 184 | 209 | 235 |
| 13644 | M | 285 | 300 | 275 | 350 | 229 | 225 |
| 2784123 | M | 300 | 300 | 300 | 300 | 300 | 300 |
| 2963028 | M | 137 | 150 | 150 | 192 | 173 | 160 |
| 13513 | F | 149 | 128 | 146 | 157 | 145 | 127 |

TABLE 9-continued

Average daily food consumption per week (weeks 1-6)

| Dog ID | Sex | Week 1 | 2 | 3 | 4 | 5 | 6 |
|---|---|---|---|---|---|---|---|
| 13490 | M | 190 | 246 | 253 | 143 | 144 | 166 |
| Mean: | | 207 | 215 | 214 | 198 | 194 | 197 |
| SD: | | 64.5 | 65.6 | 57.4 | 53.1 | 52.9 | 54.1 |

TABLE 10

Average daily food consumption per week (weeks 7-12)

| Dog ID | Sex | 7 | 8 | 9 | 10 | 11 | 12 | Avg |
|---|---|---|---|---|---|---|---|---|
| 13536 | F | 200 | 200 | 200 | 200 | 200 | 182 | 201 |
| 2753822 | F | 208 | 145 | 160 | 207 | 202 | 242 | 179 |
| 2808987 | F | 231 | 197 | 203 | 222 | 194 | 217 | 211 |
| 13644 | M | 200 | 200 | 200 | 200 | 190 | 190 | 229 |
| 2784123 | M | 300 | 300 | 275 | 275 | 165 | 165 | 273 |
| 2963028 | M | 200 | 190 | 179 | 199 | 226 | 185 | 179 |
| 13513 | F | 205 | 280 | 143 | 104 | 168 | 191 | 162 |
| 13490 | M | 191 | 266 | 193 | 214 | 215 | 210 | 203 |
| Mean: | | 217 | 222 | 194 | 203 | 195 | 198 | 204 |
| SD: | | 35.5 | 53.3 | 39.1 | 47.1 | 20.9 | 24.0 | 34.9 |

Test Article Consumption

Five of the eight dogs had 100% acceptance of the chews. Three dogs had to be dosed on occasion during the study: Dog ID #13644 (dosed 6.5% of the time), Dog ID #13513 (dosed 2.4% of the time) and Dog ID #2784123 (dosed 17.3% of the time).

Hematology and Serum Chemistry

Beginning in Week 1, there was a slight increase mean alkaline phosphatase (ALP) value for the group. This value remained stable until Week 7 when the group mean ALP value became increasingly elevated. The highest group mean value was observed during the final week of the study, but did not exceed the normal reference range, shown in Table 11. The cause of the group mean value elevations appeared to be due to three dogs (13536, 2753822 and 2808987). By the end of the study 13536 and 2753822 were above 100 U/L, but did not exceed the normal high of 131 U/L. Thus, their levels remained within the normal reference range. The observed elevations in only a few animals in the group may indicate individual sensitivity to the product. All other blood parameters remained within normal limits and no apparent trends were noted. Hematology and serum chemistry results are presented in Tables 12-19.

TABLE 11

Hematology and serum chemistry normal reference ranges

| Parameter | Normal Reference Ranges |
|---|---|
| Total Protein (g/dL): | 5.0-7.4 g/dL |
| Albumin (g/dL): | 2.7-4.4 g/dL |
| Globulin (g/dL): | 1.6-3.6 g/dL |
| A/G Ratio: | 0.8-2.0 Ratio |
| AST (U/L): | 15-66 U/L |
| ALT (U/L): | 12-118 U/L |
| Alkaline Phosphatase (U/L): | 5-131 U/L |
| GGTP (U/L): | 1-12 U/L |
| Total Bilirubin (mg/dL): | 0.1-0.3 mg/dL |
| Urea Nitrogen (mg/dL): | 6-31 mg/dL |
| Creatinine (mg/dL): | 0.5-1.6 mg/dL |
| BUN/Creatinine Ratio: | 4-27 Ratio |
| Phosphorus (mg/dL): | 2.5-6.0 mg/dL |
| Glucose (mg/dL): | 70-138 mg/dL |
| Calcium (mg/dL): | 8.9-11.4 mg/dL |
| Magnesium (mEq/L): | 1.5-2.5 mEq/L |
| Sodium (mEq/L): | 139-154 mEq/L |
| Potassium (mEq/L): | 3.6-5.5 mEq/L |
| Chloride (mEq/L): | 102-120 mEq/L |
| Cholesterol (mg/dL): | 92-324 mg/dL |
| Triglycerides (mg/dL): | 29-291 mg/dL |
| CPK (U/L): | 59-895 U/L |
| WBC (10^3/mm 3): | 4.0-15.5 10^3/mm 3 |
| RBC (10^6/mm 3): | 4.8-9.3 10^6/mm 3 |
| Hemoglobin (g/dL): | 12.1-20.3 g/dL |
| Hematocrit (%): | 36-60% |
| MCV (um^3): | 58-79 um^3 |
| MCH (uug): | 19-28 uug |
| MCHC (g/dL): | 30-38 g/dL |
| Platelets (10^3/mm 3): | 170-400 10^3/mm 3 |
| Absolute Polys: | 2060-10600 |
| Absolute Bands: | 0-300 |
| Absolute Lymphs: | 690-4500 |
| Absolute Monos: | 0-840 |
| Absolute Eos: | 0-1200 |
| Absolute Basos: | 0-150 |

TABLE 12

Summary of hematology and serum chemistry results (weeks 0-5) - Part 1

| | Protein (g/dL) | Albumin (g/dL) | Globulin | A/G Ratio | AST (U/L) | ALT (U/L) | Alkaline (U/L) | GGIP (U/L) | Total Bilirubin (mg/dL) | Urea Nitrogen (mg/dL) | Creatinine (mg/dL) |
|---|---|---|---|---|---|---|---|---|---|---|---|
| | | | | Initial Results | | | | | | | |
| Mean: | 6.1 | 3.5 | 2.6 | 1.4 | 27 | 34 | 39 | 4 | 0.1 | 11 | 0.5 |
| SD: | 0.30 | 0.22 | 0.33 | 0.21 | 6.9 | 7.6 | 16.1 | 0.5 | 0.04 | 2.1 | 0.07 |
| N: | 8 | 8 | 8 | 8 | 8 | 8 | 8 | 8 | 8 | 8 | 8 |
| | | | | Week 1 | | | | | | | |
| Mean: | 6.2 | 3.5 | 2.7 | 1.3 | 26 | 29 | 46 | 4 | 0.1 | 11 | 0.5 |
| SD: | 0.34 | 0.25 | 0.43 | 0.24 | 5.7 | 5.8 | 26.7 | 1.3 | 0.00 | 2.4 | 0.09 |
| N: | 8 | 8 | 8 | 8 | 8 | 8 | 8 | 8 | 8 | 8 | 8 |
| | | | | Week 2 | | | | | | | |
| Mean: | 6.0 | 3.5 | 2.5 | 1.4 | 26 | 30 | 49 | 3 | 0.1 | 10 | 0.5 |
| SD: | 0.49 | 0.24 | 0.48 | 0.29 | 5.9 | 5.7 | 23.8 | 0.5 | 0.00 | 1.6 | 0.06 |
| N: | 8 | 8 | 8 | 8 | 8 | 8 | 8 | 8 | 8 | 8 | 8 |

TABLE 12-continued

Summary of hematology and serum chemistry results (weeks 0-5) - Part 1

|  | Protein (g/dL) | Albumin (g/dL) | Globulin | A/G Ratio | AST (U/L) | ALT (U/L) | Alkaline (U/L) | GGTP (U/L) | Total Bilirubin (mg/dL) | Urea Nitrogen (mg/dL) | Creatinine (mg/dL) |
|---|---|---|---|---|---|---|---|---|---|---|---|
| | | | | | | Week 3 | | | | | |
| Mean: | 6.2 | 3.4 | 2.7 | 1.3 | 25 | 28 | 48 | 3 | 0.1 | 10 | 0.5 |
| SD: | 0.43 | 0.23 | 0.40 | 0.18 | 6.0 | 5.4 | 19.6 | 0.5 | 0.00 | 1.8 | 0.06 |
| N: | 8 | 8 | 8 | 8 | 8 | 8 | 8 | 8 | 8 | 8 | 8 |
| | | | | | | Week 4 | | | | | |
| Mean: | 5.9 | 3.5 | 2.5 | 1.5 | 25 | 27 | 46 | 3 | 0.3 | 10 | 0.5 |
| SD: | 0.45 | 0.23 | 0.40 | 0.24 | 7.0 | 5.9 | 21.0 | 0.9 | 0.00 | 1.6 | 0.05 |
| N: | 8 | 8 | 8 | 8 | 8 | 8 | 8 | 8 | 8 | 8 | 8 |
| | | | | | | Week 5 | | | | | |
| Mean: | 6.2 | 3.5 | 2.8 | 1.3 | 25 | 29 | 48 | 4 | 0.1 | 10 | 0.6 |
| SD: | 0.42 | 0.24 | 0.42 | 0.21 | 5.7 | 6.3 | 22.0 | 0.6 | 0.04 | 1.9 | 0.09 |
| N: | 8 | 8 | 8 | 8 | 8 | 8 | 8 | 8 | 8 | 8 | 8 |

TABLE 13

Summary of hematology and serum chemistry results (weeks 6-10) - Part 1

|  | Total Protein (g/dL) | Albumin (g/dL) | Globulin (g/dL) | A/G Ratio | AST (U/L) | ALT (U/L) | Alkaline Phosphatase (U/L) | GGTP (U/L) | Total Bilirubin (mg/dL) | Urea Nitrogen (mg/dL) | Creatinine (mg/dL) |
|---|---|---|---|---|---|---|---|---|---|---|---|
| | | | | | | Week 6 | | | | | |
| Mean: | 6.0 | 3.4 | 2.6 | 1.4 | 24 | 29 | 47 | 4 | 0.1 | 10 | 0.5 |
| SD: | 0.41 | 0.24 | 0.42 | 0.25 | 5.8 | 6.4 | 23.0 | 0.4 | 0.00 | 1.5 | 0.07 |
| N: | 8 | 8 | 8 | 8 | 8 | 8 | 8 | 8 | 8 | 8 | 8 |
| | | | | | | Week 7 | | | | | |
| Mean: | 6.4 | 3.6 | 2.8 | 1.3 | 25 | 32 | 54 | 4 | 0.1 | 10 | 0.6 |
| SD: | 0.41 | 0.32 | 0.35 | 0.21 | 6.2 | 8.3 | 25.6 | 0.7 | 0.00 | 1.5 | 0.11 |
| N: | 8 | 8 | 8 | 8 | 8 | 8 | 8 | 8 | 8 | 8 | 8 |
| | | | | | | Week 8 | | | | | |
| Mean: | 6.3 | 3.5 | 2.9 | 1.2 | 23 | 35 | 56 | 4 | 0.1 | 11 | 0.5 |
| SD: | 0.45 | 0.28 | 0.41 | 0.18 | 4.5 | 28.2 | 23.3 | 0.5 | 0.00 | 2.8 | 0.08 |
| N: | 8 | 8 | 8 | 8 | 8 | 8 | 8 | 8 | 8 | 8 | 8 |
| | | | | | | Week 9 | | | | | |
| Mean: | 6.2 | 3.6 | 2.6 | 1.4 | 25 | 31 | 55 | 5 | 0.2 | 11 | 0.6 |
| SD: | 0.39 | 0.20 | 0.41 | 0.22 | 4.2 | 8.8 | 29.2 | 0.8 | 0.05 | 1.8 | 0.10 |
| N: | 8 | 8 | 8 | 8 | 8 | 8 | 8 | 8 | 8 | 8 | 8 |
| | | | | | | Week 10 | | | | | |
| Mean: | 6.1 | 3.5 | 2.6 | 1.4 | 24 | 29 | 56 | 4 | 0.1 | 11 | 0.5 |
| SD: | 0.42 | 0.22 | 0.43 | 0.26 | 5.0 | 7.0 | 32.7 | 0.6 | 0.00 | 1.7 | 0.08 |
| N: | 8 | 8 | 8 | 8 | 8 | 8 | 8 | 8 | 8 | 8 | 8 |
| | | | | | | Final Results | | | | | |
| Mean: | 6.0 | 3.4 | 2.6 | 1.4 | 25 | 28 | 61 | 4 | 0.1 | 11 | 0.5 |
| SD: | 0.47 | 0.23 | 0.46 | 0.26 | 4.2 | 7.3 | 35.7 | 1.1 | 0.05 | 1.1 | 0.11 |
| N: | 8 | 8 | 8 | 8 | 8 | 8 | 8 | 8 | 8 | 8 | 8 |

TABLE 14

Summary of hematology and serum chemistry results (weeks 0-5) - Part 2

|  | BUN/ Creatinine Ratio | Phosphorus (mg/dL) | Glucose (mg/dL) | Calcium (mg/dL) | Magnesium (mEq/L) | Sodium (mEq/L) | Potassium (mEq/L) | Chloride (mEq/L) | Cholesterol (mg/dL) | Triglycerides (mg/dL) |
|---|---|---|---|---|---|---|---|---|---|---|
| | | | | | | Initial Results | | | | |
| Mean: | 21 | 4.3 | 97 | 10.4 | 1.6 | 148 | 4.3 | 113 | 182 | 48 |
| SD: | 2.7 | 0.62 | 0.4 | 0.33 | 0.13 | 1.2 | 0.35 | 0.9 | 36.5 | 11.1 |
| N: | 8 | 8 | 8 | 8 | 8 | 8 | 8 | 8 | 8 | 8 |

TABLE 14-continued

Summary of hematology and serum chemistry results (weeks 0-5) - Part 2

| | BUN/ Creatinine Ratio | Phosphorus (mg/dL) | Glucose (mg/dL) | Calcium (mg/dL) | Magnesium (mEq/L) | Sodium (mEq/L) | Potassium (mEq/L) | Chloride (mEq/L) | Cholesterol (mg/dL) | Triglycerides (mg/dL) |
|---|---|---|---|---|---|---|---|---|---|---|
| | | | | | Week 1 | | | | | |
| Mean: | 21 | 4.2 | 95 | 10.5 | 1.6 | 147 | 4.4 | 112 | 188 | 45 |
| SD: | 3.0 | 0.89 | 6.6 | 0.31 | 0.08 | 0.6 | 0.25 | 1.6 | 45.8 | 10.8 |
| N: | 8 | 8 | 8 | 8 | 8 | 8 | 8 | 8 | 8 | 8 |
| | | | | | Week 2 | | | | | |
| Mean: | 20 | 4.0 | 93 | 10.4 | 1.5 | 147 | 4.5 | 111 | 191 | 47 |
| SD: | 2.7 | 0.78 | 6.4 | 0.28 | 0.13 | 1.6 | 0.33 | 1.6 | 43.8 | 12.8 |
| N: | 8 | 8 | 8 | 8 | 8 | 8 | 8 | 8 | 8 | 8 |
| | | | | | Week 3 | | | | | |
| Mean: | 20 | 4.2 | 102 | 10.5 | 1.6 | 150 | 4.0 | 113 | 200 | 43 |
| SD: | 4.1 | 0.79 | 6.0 | 0.39 | 0.09 | 1.8 | 0.26 | 2.2 | 11.4 | 9.1 |
| N: | 8 | 8 | 8 | 8 | 8 | 8 | 8 | 8 | 8 | 8 |
| | | | | | Week 4 | | | | | |
| Mean: | 20 | 4.1 | 92 | 10.0 | 1.6 | 148 | 4.4 | 113 | 203 | 44 |
| SD: | 2.0 | 0.64 | 6.5 | 0.32 | 0.08 | 1.1 | 0.37 | 1.5 | 33.4 | 10.7 |
| N: | 8 | 8 | 8 | 8 | 8 | 8 | 8 | 8 | 8 | 8 |
| | | | | | Week 5 | | | | | |
| Mean: | 18 | 3.9 | 96 | 10.3 | 1.5 | 148 | 4.4 | 112 | 206 | 43 |
| SD: | 2.1 | 0.54 | 7.7 | 0.25 | 0.07 | 1.4 | 0.27 | 1.6 | 30.8 | 12.2 |
| N: | 8 | 8 | 8 | 8 | 8 | 8 | 8 | 8 | 8 | 8 |

TABLE 15

Summary of hematology and serum chemistry results (weeks 6-10) - Part 2

| | BUN/ Creatinine Ratio | Phosphorus (mg/dL) | Glucose (mg/dL) | Calcium (mg/dL) | Magnesium (mEq/L) | Sodium (mEq/L) | Potassium (mEq/L) | Chloride (mEq/L) | Cholesterol (mg/dL) | Triglycerides (mg/dL) |
|---|---|---|---|---|---|---|---|---|---|---|
| | | | | | Week 6 | | | | | |
| Mean: | 20 | 3.9 | 91 | 10.0 | 1.5 | 147 | 4.4 | 112 | 191 | 44 |
| SD: | 1.8 | 0.48 | 6.3 | 0.27 | 0.09 | 0.7 | 0.10 | 2.6 | 31.5 | 13.1 |
| N: | 8 | 8 | 8 | 8 | 8 | 8 | 8 | 8 | 8 | 8 |
| | | | | | Week 7 | | | | | |
| Mean: | 18 | 4.1 | 96 | 10.0 | 1.6 | 149 | 4.4 | 112 | 197 | 48 |
| SD: | 2.9 | 0.50 | 8.0 | 0.38 | 0.12 | 2.0 | 0.27 | 1.2 | 31.3 | 12.3 |
| N: | 8 | 8 | 8 | 8 | 8 | 8 | 8 | 8 | 8 | 8 |
| | | | | | Week 8 | | | | | |
| Mean: | 22 | 4.2 | 102 | 10.2 | 1.6 | 146 | 4.3 | 111 | 211 | 43 |
| SD: | 6.9 | 0.92 | 7.9 | 0.35 | 0.10 | 2.2 | 0.21 | 1.6 | 33.7 | 12.9 |
| N: | 8 | 8 | 8 | 8 | 8 | 8 | 8 | 8 | 8 | 8 |
| | | | | | Week 9 | | | | | |
| Mean: | 20 | 3.8 | 100 | 10.3 | 1.5 | 149 | 4.5 | 114 | 204 | 44 |
| SD: | 3.5 | 0.71 | 8.5 | 0.33 | 0.12 | 1.2 | 0.29 | 1.5 | 34.1 | 11.5 |
| N: | 8 | 8 | 8 | 8 | 8 | 8 | 8 | 8 | 8 | 8 |
| | | | | | Week 10 | | | | | |
| Mean: | 22 | 4.3 | 94 | 10.3 | 1.6 | 149 | 4.4 | 113 | 206 | 46 |
| SD: | 2.8 | 0.81 | 9.2 | 0.25 | 0.11 | 0.5 | 0.26 | 1.9 | 41.3 | 12.4 |
| N: | 8 | 8 | 8 | 8 | 8 | 8 | 8 | 8 | 8 | 8 |
| | | | | | Final Results | | | | | |
| Mean: | 2.2 | 4.0 | 99 | 10.1 | 1.6 | 148 | 4.2 | 113 | 212 | 46 |
| SD: | 3.9 | 0.68 | 6.4 | 0.34 | 0.12 | 1.2 | 0.14 | 3.0 | 49.2 | 15.8 |
| N: | 8 | 8 | 8 | 8 | 8 | 8 | 8 | 8 | 8 | 8 |

TABLE 16

Summary of hematology and serum chemistry results (weeks 0-5) - Part 3

| | CPK (U/L) | WBC (10^3/mm3) | RBC (10^6/mm3) | Hemoglobin (g/dL) | Hematocrit (%) | MCV (um^3) | MCH (uug) | MCHC (g/dl) | Platelets (10^3/mm3) |
|---|---|---|---|---|---|---|---|---|---|
| Initial Results | | | | | | | | | |
| Mean: | 130 | 8.4 | 7.5 | 17.5 | 54 | 72 | 23.5 | 33 | 318 |
| SD: | 45.2 | 2.06 | 0.72 | 1.67 | 4.1 | 2.4 | 0.80 | 1.0 | 50.7 |
| N: | 8 | 8 | 8 | 8 | 8 | 8 | 8 | 8 | 8 |
| Week 1 | | | | | | | | | |
| Mean: | 95 | 9.8 | 7.1 | 16.6 | 52 | 73 | 23.3 | 32 | 312 |
| SD: | 12.6 | 2.39 | 0.37 | 0.86 | 2.5 | 2.1 | 0.58 | 0.4 | 54.6 |
| N: | 8 | 8 | 8 | 8 | 8 | 8 | 8 | 8 | 8 |
| Week 2 | | | | | | | | | |
| Mean: | 96 | 8.5 | 7.5 | 17.0 | 54 | 72 | 22.8 | 31 | 318 |
| SD: | 23.5 | 1.63 | 0.37 | 0.60 | 2.1 | 1.9 | 0.59 | 0.7 | 59.8 |
| N: | 8 | 8 | 8 | 8 | 8 | 8 | 8 | 8 | 8 |
| Week 3 | | | | | | | | | |
| Mean: | 81 | 8.7 | 7.4 | 16.8 | 53 | 72 | 22.7 | 32 | 306 |
| SD: | 20.5 | 1.57 | 0.43 | 0.82 | 2.9 | 2.4 | 0.72 | 1.4 | 43.3 |
| N: | 8 | 8 | 8 | 8 | 8 | 8 | 8 | 8 | 8 |
| Week 4 | | | | | | | | | |
| Mean: | 142 | 7.7 | 7.3 | 17.1 | 53 | 72 | 23.4 | 33 | 311 |
| SD: | 122.3 | 1.26 | 0.57 | 1.29 | 3.0 | 3.5 | 0.43 | 1.2 | 43.0 |
| N: | 8 | 8 | 8 | 8 | 8 | 8 | 8 | 8 | 8 |
| Week 5 | | | | | | | | | |
| Mean: | 109 | 8.6 | 7.3 | 17.2 | 54 | 73 | 23.5 | 32 | 314 |
| SD: | 29.5 | 1.38 | 0.51 | 1.08 | 3.2 | 2.1 | 0.63 | 0.4 | 27.0 |
| N: | 8 | 8 | 8 | 8 | 8 | 8 | 8 | 8 | 8 |

TABLE 17

Summary of hematology and serum chemistry results (weeks 6-10) - Part 3

| | CPK (U/L) | WBC (10^3/mm3) | RBC (10^6/mm3) | Hemoglobin (g/dL) | Hematocrit (%) | MCV (um^3) | MCH (uug) | MCHC (g/dl) | Platelets (10^3/mm3) |
|---|---|---|---|---|---|---|---|---|---|
| Week 6 | | | | | | | | | |
| Mean: | 89 | 8.9 | 7.4 | 17.2 | 50 | 68 | 23.4 | 34 | 348 |
| SD: | 30.6 | 2.23 | 0.44 | 1.04 | 2.6 | 1.9 | 0.63 | 0.5 | 40.3 |
| N: | 8 | 8 | 8 | 8 | 8 | 8 | 8 | 8 | 8 |
| Week 7 | | | | | | | | | |
| Mean: | 110 | 7.4 | 7.9 | 17.9 | 58 | 74 | 22.8 | 31 | 313 |
| SD: | 44.8 | 1.27 | 0.50 | 1.21 | 3.4 | 1.8 | 0.70 | 0.6 | 47.3 |
| N: | 8 | 8 | 8 | 8 | 8 | 8 | 8 | 8 | 8 |
| Week 8 | | | | | | | | | |
| Mean: | 83 | 7.3 | 7.9 | 17.9 | 57 | 73 | 22.7 | 32 | 304 |
| SD: | 14.4 | 2.56 | 0.36 | 0.56 | 2.2 | 1.7 | 0.76 | 0.5 | 30.6 |
| N: | 8 | 8 | 8 | 8 | 8 | 8 | 8 | 8 | 8 |
| Week 9 | | | | | | | | | |
| Mean: | 83 | 8.4 | 7.8 | 18.1 | 54 | 70 | 23.2 | 33 | 321 |
| SD: | 16.6 | 2.52 | 0.36 | 0.84 | 3.0 | 2.8 | 1.00 | 2.1 | 20.9 |
| N: | 8 | 8 | 8 | 8 | 8 | 8 | 8 | 8 | 8 |
| Week 10 | | | | | | | | | |
| Mean: | 102 | 7.8 | 7.6 | 17.9 | 56 | 74 | 23.6 | 32 | 325 |
| SD: | 22.2 | 1.94 | 0.31 | 0.79 | 2.4 | 1.9 | 0.64 | 0.0 | 41.9 |
| N: | 8 | 8 | 8 | 8 | 8 | 8 | 8 | 8 | 8 |
| Final Results | | | | | | | | | |
| Mean: | 97 | 7.7 | 7.5 | 17.8 | 51 | 69 | 23.7 | 35 | 347 |
| SD: | 14.5 | 1.91 | 0.39 | 0.82 | 2.1 | 1.9 | 0.71 | 0.5 | 54.3 |
| N: | 8 | 8 | 8 | 8 | 8 | 8 | 8 | 8 | 8 |

TABLE 18

Summary of hematology and serum chemistry results (weeks 0-5) - Part 4

| | Abs Polys | % Polys | Abs Bands | % Bands | Abs Lymphs | % Lymphs | Abs Monos | % Monos | Abs Eos | % Eos | Abs Basos | % Basos |
|---|---|---|---|---|---|---|---|---|---|---|---|---|
| | | | | | Initial Results | | | | | | | |
| Mean: | 5508 | 65 | 0 | 0 | 2346 | 28 | 361 | 5 | 197 | 2 | 0 | 0 |
| SD: | 1065.1 | 5.3 | 0.0 | 0.0 | 476.4 | 4.0 | 159.1 | 2.4 | 87.1 | 0.9 | 0.0 | 0.0 |
| N: | 8 | 8 | 8 | 8 | 8 | 8 | 8 | 8 | 8 | 8 | 8 | 8 |
| | | | | | Week 1 | | | | | | | |
| Mean: | 6602 | 67 | 0 | 0 | 2219 | 24 | 615 | 6 | 326 | 3 | 0 | 0 |
| SD: | 2065.4 | 6.2 | 0.0 | 0.0 | 323.3 | 6.0 | 411.8 | 3.2 | 230.6 | 2.4 | 0.0 | 0.0 |
| N: | 8 | 8 | 8 | 8 | 8 | 8 | 8 | 8 | 8 | 8 | 8 | 8 |
| | | | | | Week 2 | | | | | | | |
| Mean: | 5562 | 65 | 0 | 0 | 2223 | 27 | 370 | 4 | 308 | 4 | 0 | 0 |
| SD: | 1270.4 | 4.2 | 0.0 | 0.0 | 354.4 | 4.0 | 113.0 | 1.1 | 108.5 | 0.9 | 0.0 | 0.0 |
| N: | 8 | 8 | 8 | 8 | 8 | 8 | 8 | 8 | 8 | 8 | 8 | 8 |
| | | | | | Week 3 | | | | | | | |
| Mean: | 5877 | 67 | 0 | 0 | 2166 | 25 | 440 | 5 | 255 | 3 | 0 | 0 |
| SD: | 1235.5 | 3.7 | 0.0 | 0.0 | 450.1 | 3.3 | 92.9 | 1.1 | 82.2 | 1.2 | 0.0 | 0.0 |
| N: | 8 | 8 | 8 | 8 | 8 | 8 | 8 | 8 | 8 | 8 | 8 | 8 |
| | | | | | Week 4 | | | | | | | |
| Mean: | 523.6 | 68 | 6 | 0 | 1912 | 25 | 297 | 4 | 238 | 3 | 0 | 0 |
| SD: | 1098.9 | 3.7 | 0.0 | 0.0 | 185.4 | 3.7 | 102.8 | 1.2 | 103.1 | 1.2 | 0.0 | 0.0 |
| N: | 8 | 8 | 8 | 8 | 8 | 8 | 8 | 8 | 8 | 8 | 8 | 8 |
| | | | | | Week 5 | | | | | | | |
| Mean: | 5864 | 68 | 0 | 0 | 2061 | 24 | 402 | 5 | 261 | 3 | 0 | 0 |
| SD: | 1124.4 | 4.0 | 0.0 | 0.0 | 410.2 | 5.0 | 178.4 | 1.8 | 112.2 | 1.1 | 0.0 | 0.0 |
| N: | 8 | 8 | 8 | 8 | 8 | 8 | 8 | 8 | 8 | 8 | 8 | 8 |

TABLE 19

Summary of hematology and serum chemistry results (weeks 6-10) - Part 4

| | Abs Polys | % Polys | Abs Bands | % Bands | Abs Lymphs | % Lymphs | Abs Monos | % Monos | Abs Eos | % Eos | Abs Basos | % Basos |
|---|---|---|---|---|---|---|---|---|---|---|---|---|
| | | | | | Week 6 | | | | | | | |
| Mean: | 5961 | 66 | 0 | 0 | 2281 | 27 | 400 | 5 | 296 | 3 | 0 | 0 |
| SD: | 1852.8 | 4.9 | 0.0 | 0.0 | 289.4 | 4.8 | 121.8 | 1.9 | 204.1 | 1.5 | 0.0 | 0.0 |
| N: | 8 | 8 | 8 | 8 | 8 | 8 | 8 | 8 | 8 | 8 | 8 | 8 |
| | | | | | Week 7 | | | | | | | |
| Mean: | 4944 | 67 | 0 | 0 | 1918 | 26 | 329 | 5 | 209 | 3 | 0 | 0 |
| SD: | 1030.3 | 1.9 | 0.0 | 0.0 | 374.2 | 4.1 | 115.0 | 1.4 | 40.6 | 0.6 | 0.0 | 0.0 |
| N: | 8 | 8 | 8 | 8 | 8 | 8 | 8 | 8 | 8 | 8 | 8 | 8 |
| | | | | | Week 8 | | | | | | | |
| Mean: | 4889 | 65 | 0 | 0 | 1960 | 28 | 335 | 5 | 154 | 2 | 0 | 0 |
| SD: | 2096.3 | 5.6 | 0.0 | 0.0 | 371.7 | 4.5 | 186.2 | 1.3 | 65.9 | 1.5 | 0.0 | 0.0 |
| N: | 8 | 8 | 8 | 8 | 8 | 8 | 8 | 8 | 8 | 8 | 8 | 8 |
| | | | | | Week 9 | | | | | | | |
| Mean: | 5705 | 67 | 0 | 0 | 2056 | 26 | 366 | 4 | 249 | 3 | 0 | 0 |
| SD: | 1967.2 | 4.1 | 0.0 | 0.0 | 364.1 | 4.1 | 155.1 | 1.1 | 222.5 | 1.6 | 0.0 | 0.0 |
| N: | 8 | 8 | 8 | 8 | 8 | 8 | 8 | 8 | 8 | 8 | 8 | 8 |
| | | | | | Week 10 | | | | | | | |
| Mean: | 5188 | 66 | 0 | 0 | 1997 | 26 | 375 | 5 | 190 | 3 | 0 | 0 |
| SD: | 1507.5 | 3.7 | 0.0 | 0.0 | 386.8 | 3.5 | 95.1 | 0.8 | 68.9 | 0.8 | 0.0 | 0.0 |
| N: | 8 | 8 | 8 | 8 | 8 | 8 | 8 | 8 | 8 | 8 | 8 | 8 |
| | | | | | Final Results | | | | | | | |
| Mean: | 5221 | 67 | 0 | 0 | 1940 | 26 | 359 | 5 | 181 | 2 | 0 | 0 |
| SD: | 1658.6 | 5.0 | 5.9 | 0.0 | 0.0 | 453.8 | 7.0 | 197.9 | 2.4 | 0.5 | 0.0 | 0.0 |
| N: | 8 | 8 | 8 | 8 | 8 | 8 | 8 | 8 | 8 | 8 | 8 | 8 |

Clinical Observations

During the study, occasional instances of loose stool and emesis were recorded. Dog ID #13536 was observed having five instances of food or bile emesis and six instances of loose stool. Dog ID #13513 was observed having two instances of loose stool. Dog ID #27583822 was observed having two instances of food emesis and eight instances of loose stool. Dog ID #13644 was observed having 12 instances of loose stool. Dog ID #13490 was observed having two instances of loose stool. Dog ID #2808987 was observed having four instances of loose stool. Dog ID #2963028 was observed having six instances of loose stool. Dog ID #2784123 was observed having six instances of loose stool. Occasional episodes of loose stool and bile emesis are not unusual in the dog colony and were not considered to be related to the test article. Clinical observations are listed in Table 20.

TABLE 20

Clinical observations

| Dog ID | Date | Observation |
|---|---|---|
| 13490 | Jan. 18, 2018 | Loose stool |
| 13490 | Feb. 4, 2018 | Loose stool |
| 13313 | Jan. 16, 2018 | Small amount loose stool |
| 13513 | Jan. 18, 2018 | Loose stool |
| 13513 | Jan. 19, 2018 | Afraid and shaking head |
| 13513 | Jan. 25, 2018 | Shaking head |
| 13536 | Jan. 14, 2018 | Food and chew vomit |
| 13536 | Jan. 18, 2018 | Loose stool |
| 13536 | Jan. 22, 2018 | Food vomit prior to dosing |
| 13536 | Jan. 26, 2018 | Food vomit prior to dosing |
| 13536 | Jan. 29, 2018 | Bile vomit |
| 13536 | Feb. 4, 2018 | Bile vomit with blood |
| 13536 | Feb. 12, 2018 | Loose stool with mucus |
| 13536 | Feb. 15, 2018 | Loose stool |
| 13536 | Feb. 16, 2018 | Loose stool |
| 13536 | Mar. 21, 2018 | Loose stool |
| 13536 | Mar. 24, 2018 | Loose stool |
| 13644 | Jan. 18, 2018 | Loose stool |
| 13644 | Feb. 2, 2018 | Loose stool with mucus |
| 13644 | Feb. 4, 2018 | Loose stool |
| 13644 | Feb. 3, 2018 | Loose stool with mucus |
| 13644 | Feb. 6, 2018 | Loose stool |
| 13644 | Feb. 7, 2018 | Loose stool |
| 13644 | Feb. 10, 2018 | Loose stool |
| 13644 | Feb. 11, 2018 | Loose stool |
| 13644 | Feb. 15, 2018 | Loose stool |
| 13644 | Mar. 15, 2018 | Loose stool |
| 13644 | Mar. 17, 2018 | Loose stool |
| 13644 | Mar. 20, 2018 | Loose stool with mucus |
| 2753822 | Jan. 18, 2018 | Loose stool |
| 2753822 | Jan. 21, 2018 | Food vomit |
| 2753822 | Feb. 10, 2018 | Loose stool |
| 2753822 | Mar. 15, 2018 | Loose stool with blood |
| 2753822 | Mar. 18, 2018 | Loose stool |
| 2753822 | Mar. 20, 2018 | Loose stool |
| 2753822 | Mar. 24, 2018 | Two instances of loose stool |

TABLE 20-continued

Clinical observations

| Dog ID | Date | Observation |
|---|---|---|
| 2753822 | Mar. 29, 2018 | Loose stool |
| 2753822 | Mar. 31, 2018 | Food vomit |
| 2784123 | Jan. 18, 2018 | Loose stool |
| 2784123 | Mar. 18, 2018 | Loose stool |
| 2784123 | Mar. 21, 2018 | Loose stool |
| 2784123 | Mar. 24, 2018 | Two instances of loose stool |
| 2784123 | Mar. 29, 2018 | Loose stool |
| 2808987 | Jan. 18, 2018 | Loose stool |
| 2808987 | Feb. 5, 2018 | Loose stool |
| 2808987 | Feb. 10, 2018 | Loose stool |
| 2803987 | Mar. 20, 2018 | Loose stool |
| 2963028 | Jan. 18, 2018 | Loose stool |
| 2963028 | Feb. 10, 2018 | Loose stool |
| 2963028 | Mar. 20, 2018 | Loose stool |
| 2963028 | Mar. 22, 2018 | Loose stool |
| 2963028 | Mar. 24, 2018 | Loose stool |
| 2963028 | Mar. 25, 2018 | Loose stool |

Conclusions

There were no adverse effects on body weights or food consumption. Group mean alkaline phosphatase values exhibited mild elevations during the study without exceeding the normal reference range. The remaining hematology and serum chemistry results remained within normal limits throughout the study and apparent trends were not observed over time. No clinical observations that were considered to be related to the administration of the test article were observed for any of the dogs during the course of the study. Overall acceptance of the treat was 96.7% with 5 out of 8 consuming the treat 100% of the time for the duration of the study.

Example 13

Canine Pilot Study

A pilot study was conducted to assess the effectiveness of ElleVet Mobility Oil on the treatment of osteoarthritis in canines.

Methods

Five dogs suffering from end stage osteoarthritis, joint pain, and geriatric pain were selected for the study, as shown in Tables 21 and 22.

Per manufacturer's instructions, dogs were given a loading dose of 2 mg/kg every 12 hours for the first 2 weeks then reduced to 1 mg/kg every 12 hours for 2 weeks. Dogs were then returned to doses of 2 mg/kg every 12 hours for the final four weeks of the study.

On days 0, 14, 30, and 60, dogs were evaluated by flexion and extension measurements, muscle musculature measurements, a canine brief pain inventory survey, and a gait analysis using a pressure sensing walkway.

TABLE 21

Animal Information

| Patient Number | Name | Age | Sex | Breed | Weight (#) | OA Score (0-3) | Body Condition (1-9) | Medications |
|---|---|---|---|---|---|---|---|---|
| 3496 | Gipper Hatch | 12 yrs 6 mo | FS | Golden Retriever | 64.9 | R: 3 L: 2 | 6 | Rimadyl, apoquel, dasuquin advanced |
| 21652 | Rocoo Payne | 15 yrs 4 mo | MN | Mixed Breed | 67.7 | B: 2 | 5 | Keppra, Galliprant |
| 13750 | Bubba Schlimm | 14 yrs 8 mo | MN | Labrador Retriever | 65.6 | R: 2 L: 1 | 4 | Galliprant, Gabapentin, Theophyline |

TABLE 21-continued

Animal Information

| Patient Number | Name | Age | Sex | Breed | Weight (#) | OA Score (0-3) | Body Condition (1-9) | Medications |
|---|---|---|---|---|---|---|---|---|
| 24478 | Aiden Langhans-Lindstadt | 7 yrs 2 mo | MN | German Shepherd | 86 | B: 2-3 | 5-5 | Gabapentin, rimadyl as needed |
| 19821 | Moose Baker | 11 yrs 7 mo | MN | Mixed Breed | 65 | L: 3/3 | 5 | Tramadol as needed |

TABLE 22

Animal history

| Patient Number | Name | Enrollment Date | History Notes |
|---|---|---|---|
| 3496 | Gipper Hatch | Wed, Jun. 11, 2014 | Bilateral medial shoulder syndrome (Subscapular tendinopathy); Bilateral chronic supraspinatus insertionopathy - Bilateral shoulder arthroscopy and radio-frequency treatment; Hobbles application, Bilateral elbow arthroscopy (2011); ADPC/PRP injections - bilateral supraspinatus, Intra-articular injections ADPC/ACS - bilateral shoulders (2011, 2012); ADPC/PRP injection -Bilateral biceps, Left teres (2014); ADPC/PRP injection - right shoulder, elbow, biceps (2016); PRP injection - right elbow (2016); OsteoBioScaff injection - right elbow (2017). |
| 21652 | Rocco Payne | Fri, Jun. 13, 2014 | Elbow arthritis, history of seizure activity, history of elevated liver enzymes |
| 13750 | Bubba Schlimm | Tue, Jun. 17, 2014 | Bilateral elbow OA, hind limb weakness |
| 24478 | Aiden Langhans-Lindstadt | Tue, Jul. 1, 2014 | Bilateral Hip Dysplasia |
| 19821 | Moose Baker | Fri, Jul. 18, 2014 | Left medial shoulder syndrome, bilateral surpaspinatus tendinopathies (R > L), L FCP –> L elbow scope & L RF tx performed (May 2016); L elbow OA |

Results

Three out of five owners (60%) reported a significant improvement in pain severity score and pain interference score. Gait analysis revealed that total pressure index (TPI %), step/stride ratio, and stance percentage did not significantly improve or decline throughout the length of the study, as shown in Tables 23-34 and FIGS. 5A-5F. Flexion improved in 3 out of 5 dogs and declined by >5 degrees in 2 out of 5 dogs. Extension improved in 2 out of 5 dogs and declined in 1 out of 5 dogs. Following completion of the study, 3 out of 4 owners that respond to a questionnaire indicated that they would like to continue using the supplements. Improvements observed by owners included improved function and comfort laying down, rising, resting, walking, energy, playing, and overall health.

TABLE 23

Total pressure index (TPI)

| Patient Number | Name | Date | Average TPI (%) Walk | | | | Average TPI (%) Trot | | | |
|---|---|---|---|---|---|---|---|---|---|---|
| | | | LF | RF | LH | RH | LF | RF | LH | RH |
| 1 | Gipper Hatch | Day 0 | 26.3 | 26.9 | 21.0 | 25.8 | 25.8 | 26.2 | 22.5 | 25.5 |
| | | Day 14 | 26.5 | 26.4 | 21.9 | 25.2 | 24.8 | 26.3 | 24.0 | 25.0 |
| | | Day 30 | 25.7 | 25.7 | 24.1 | 24.3 | 26.8 | 26.2 | 24.5 | 22.4 |
| | | Day 60 | 26 | 26.4 | 21.5 | 26 | | | | |
| 2 | Rocco Payne | Day 0 | 26.4 | 28.8 | 21.8 | 23 | 26.1 | 29.3 | 21.4 | 23.4 |
| | | Day 14 | 27 | 30.3 | 21.3 | 21.5 | 27.4 | 27.8 | 21.1 | 24 |
| | | Day 30 | 28 | 30.3 | 19.3 | 22.6 | 28 | 29.1 | 21.5 | 21.6 |
| | | Day 60 | 27.4 | 28.9 | 21.6 | 21.9 | 25.9 | 28.7 | 21.4 | 24.2 |
| 3 | Bubba Schlimm | Day 0* | 31.6 | 31 | 18.7 | 18.6 | 28.8 | 30.9 | 18.7 | 21.5 |
| | | Day 0 | 30.8 | 31.7 | 19.2 | 18.2 | 28.8 | 32.5 | 19.9 | 18.9 |
| | | Day 14 | 31.8 | 31.2 | 18.9 | 18 | 29.4 | 31.9 | 19.7 | 19 |
| | | Day 30 | 31.4 | 30.7 | 19.3 | 18.5 | 29.7 | 32 | 19.8 | 18.7 |
| | | Day 60 | 31.4 | 31.3 | 18.5 | 18.8 | 31.2 | 33.4 | 17.1 | 18.1 |
| 4 | Aiden Langhans-Lindstadt | Day 0 | 31 | 32 | 18.4 | 18.5 | 31.8 | 29.1 | 19.4 | 19.6 |
| | | Day 14 | 32.6 | 30.3 | 18.4 | 18.8 | 31.2 | 31.7 | 18.3 | 18.9 |
| | | Day 30 | 31.9 | 32.2 | 18 | 18 | 31.4 | 29.1 | 19.3 | 20.2 |
| | | Day 60 | 32.1 | 30.7 | 18.2 | 18.9 | 31.2 | 29.8 | 19.4 | 19.5 |

TABLE 23-continued

| | | | Total pressure index (TPI) | | | | | | | |
|---|---|---|---|---|---|---|---|---|---|---|
| Patient | | | Average TPI (%) Walk | | | | Average TPI (%) Trot | | | |
| Number | Name | Date | LF | RF | LH | RH | LF | RF | LH | RH |
| 5 | Moose Baker | Day 0 | 25.1 | 34.4 | 20.9 | 19.5 | 23.3 | 35.6 | 20.8 | 20.1 |
| | | Day 14 | 25.1 | 35 | 21.1 | 18.8 | 23.1 | 36.2 | 20.1 | 20.4 |
| | | Day 30 | 24.5 | 35.6 | 19.5 | 20.4 | 22.1 | 37.2 | 20.3 | 20.3 |
| | | Day 60 | 25.1 | 34.5 | 19.5 | 20.8 | 23.7 | 36.2 | 19.9 | 20.1 |

*= removed from study

TABLE 24

Exam notes

| Patient Number | Name | Date | Exam Notes |
|---|---|---|---|
| 1 | Gipper Hatch | Day 0 | Mild mid lumbar pain - reaction to palpation; right elbow thick/crepitus; left elbow swollen - moderate medial |
| | | Day 14 | Moderate left elbow effusion (medial) |
| | | Day 30 | |
| | | Day 60 | P was scuffing at a trot, cannot currently be processed. O does not think that he saw any effect during the study and actually think that P's mood dropped while receiving the higher dose. O also was upset that the gel capsules he received were not large enough to hold even a half dose. |
| 2 | Rocco Payne | Day 0 | Mild –> Moderate discomfort from L5 to LS; Discomfort for hip extension & ilio palpation bilaterally |
| | | Day 14 | bilat ilio discomfort & discomfort for hip extension L > R, significant discomfort for elbow flexion bilat, mod effusion bilat elbow medially, no back discomfort noted |
| | | Day 30 | |
| | | Day 60 | |
| 3 | Bubba Schlimm | Day 0* | **P had to be removed during the first week of the study due to impacted/infected anal glad. P had to go onto IV antibiotic restarted study once P was back to normal. |
| | | Day 0 | Bilat elbow discomfort for flexion (L > R) |
| | | Day 14 | |
| | | Day 30 | O notes that P has been much more feisty and playful |
| | | Day 60 | |
| 4 | Aiden Langhans-Lindstadt | Day 0 | |
| | | Day 14 | |
| | | Day 30 | |
| | | Day 60 | |
| 5 | Moose Baker | Day 0 | Discomfort for R shoulder extension - mineralization in area of R supraspinatus tendon |
| | | Day 14 | |
| | | Day 30 | O stated that they did not see an improvement during the study. Hip radiographs were taken after the final recheck. It was discovered that P also has |

*= removed from study

TABLE 25

| Patient | | | | Subjective Lameness | Humeral Musculature Circumference (cm) | |
|---|---|---|---|---|---|---|
| Number | Name | OA | Date | Score (0-6) | Left | Right |
| 1 | Gipper Hatch | Bilateral Elbows | Day 0 | 3 | 33 | 33 |
| | | | Day 14 | 3 | 34 | 34 |
| | | | Day 30 | 3 | 32 | 32 |
| | | | Day 60 | 3 | 33 | 33 |

TABLE 25-continued

| Patient | | | | Subjective Lameness | Humeral Musculature Circumference (cm) | |
|---|---|---|---|---|---|---|
| Number | Name | OA | Date | Score (0-6) | Left | Right |
| 2 | Rocco Payne | Bilateral Elbows | Day 0 | 4 | 35 | 35 |
| | | | Day 14 | 4 | 36.5 | 36 |
| | | | Day 30 | 4 | 36 | 36 |
| | | | Day 60 | 3 | 36 | 35 |
| 3 | Bubba Schlimm | Bilateral Elbows | Day 0* | 3 | 37 | 37 |
| | | | Day 0 | 3 | 36 | 37 |
| | | | Day 14 | 3 | 36 | 36 |
| | | | Day 30 | 2 | 36 | 37 |
| | | | Day 60 | 2 | 36 | 36 |
| 4 | Aiden Langhans-Lindstadt | Bilateral Hips | Day 0 | 2 | 47 | 47 |
| | | | Day 14 | 2 | 46 | 47.5 |
| | | | Day 30 | 1 | 47 | 47 |
| | | | Day 60 | 1 | 37 | 37 |
| 5 | Moose Baker | Left Elbow | Day 0 | 3 | 34 | 34.5 |
| | | | Day 14 | 2 | 33.5 | 34 |
| | | | Day 30 | 3 | 34 | 35.5 |
| | | | Day 60 | 3 | 34 | 35 |

*= removed from study

TABLE 26

Measurements - Part 2

| Patient | | | | Goniometry Measurements (°) | | | | Discomfort on Palpation (N—None, Y—Yes, M—Mild) | | | |
|---|---|---|---|---|---|---|---|---|---|---|---|
| | | | | Left | | Right | | Left | | Right | |
| Number | Name | OA | Date | Extension | Flexion | Extension | Flexion | Extension | Flexion | Extension | Flexion |
| 1 | Gipper Hatch | Bilateral Elbows | Day 0 | 160 | 30 | 160 | 39 | N | Y | N | Y |
| | | | Day 14 | 160 | 35 | 165 | 40 | N | Y | Y | Y |
| | | | Day 30 | 164 | 38 | 158 | 42 | Y | Y | Y | Y |
| | | | Day 60 | 165 | 41 | 162 | 44 | N | Y | Y | N |
| 2 | Rocco Payne | Bilateral Elbows | Day 0 | 152 | 52 | 164 | 60 | Y | Y | Y | Y |
| | | | Day 14 | 162 | 69 | 164 | 55 | N | Y | N | Y |
| | | | Day 30 | 158 | 69 | 163 | 63 | N | Y | N | Y |
| | | | Day 60 | 164 | 70 | 162 | 68 | N | Y | N | Y |
| 3 | Bubba Schlimm | Bilateral Elbows | Day 0* | 158 | 42 | 163 | 50 | N | Y | N | Y |
| | | | Day 0 | 165 | 45 | 162 | 52 | N | Y | N | Y |
| | | | Day 14 | 170 | 44 | 174 | 42 | N | Y | N | Y |
| | | | Day 30 | 170 | 38 | 165 | 46 | N | Y | N | Y |
| | | | Day 60 | 161 | 42 | 168 | 46 | N | Y | N | Y |
| 4 | Aiden Langhans-Lindstadt | Bilateral Hips | Day 0 | 150 | 48 | 156 | 52 | Y | N | Y | N |
| | | | Day 14 | 140 | 50 | 148 | 47 | Y | N | Y | N |
| | | | Day 30 | 149 | 60 | 145 | 49 | Y | N | Y | N |
| | | | Day 60 | 145 | 50 | 142 | 52 | Y | N | Y | N |
| 5 | Moose Baker | Left Elbow | Day 0 | 157 | 69 | 162 | 28 | Y | Y | Y | N |
| | | | Day 14 | 160 | 64 | 170 | 31 | Y | Y | N | N |
| | | | Day 30 | 152 | 60 | 172 | 28 | Y | Y | N | N |
| | | | Day 60 | 162 | 64 | 172 | 28 | N | Y | Y | N |

*= removed from study

TABLE 27

Schedule

| Patient Number | Name | Day | Date | |
|---|---|---|---|---|
| 1 | Gipper Hatch | Day 0 | Tue, Jun. 12, 2018 | |
| 2 | Rocco Payne | Day 0 | Thu, Jun. 14, 2018 | |
| 3 | Bubba Schlimm | Day 0* | Mon, Jun. 18, 2018 | **P had to be removed during the first week of the study due to impacted/infected anal glad. P had to go onto IV antibiotic restarted study once P was back to normal. |
| | | Day 0 | Mon, Jul. 9, 2018 | |

TABLE 27-continued

Schedule

| Patient Number | Name | Day | Date |
|---|---|---|---|
| 4 | Aiden Langhans-Lindstadt | Day 0 | Mon, Jul. 2, 2018 |
| 5 | Moose Baker | Day 0 | Thu, Jul. 19, 2018 |

*= removed from study

TABLE 28

Canine brief pain index - description of pain

| | | | Description of Pain: No Pain (0) → Extreme Pain (10) | | | | | |
|---|---|---|---|---|---|---|---|---|
| Patient Number | Name | Date | Pain at worst in last 7 days | Pain at least in last 7 days | Pain at average in last 7 days | Pain right now | Pain Severity Mean | Comments |
| 1 | Gipper Hatch | Day 0 | 8 | 5 | 6 | 5 | 6 | |
| | | Day 14 | 8 | 5 | 7 | 6 | 7 | |
| | | Day 30 | 8 | 6 | 6 | 6 | 7 | |
| | | Day 60 | 8 | 6 | 7 | 6 | 7 | |
| 2 | Rocco Payne | Day 0 | 6 | 6 | 5 | 6 | 6 | |
| | | Day 14 | 9 | 9 | 9 | 9 | 9 | |
| | | Day 30 | 7 | 5 | 6 | 6 | 6 | |
| | | Day 60 | 5 | 3 | 4 | 3 | 4 | |
| 3 | Bubba Schlimm | Day 0* | 6 | 4 | 5 | 5 | 5 | **P had to be removed during the first week of the study due to impacted/infected anal glad. P had to go onto IV antibiotic restarted study once P was back to normal. |
| | | Day 0 | 5 | 4 | 4 | 4 | 4 | |
| | | Day 14 | 4 | 3 | 3 | 3 | 3 | |
| | | Day 30 | 5 | 3 | 4 | 5 | 4 | |
| | | Day 60 | 3 | 2 | 2 | 2 | 2 | |
| 4 | Aiden Langhans-Lindstadt | Day 0 | 9 | 5 | 7 | 9 | 8 | |
| | | Day 14 | 7 | 4 | 5 | 3 | 5 | |
| | | Day 30 | 7 | 4 | 5 | 4 | 5 | |
| | | Day 60 | 8 | 3 | 4 | 3 | 5 | |
| 5 | Moose Baker | Day 0 | 7 | 3 | 6 | 6 | 6 | |
| | | Day 14 | 7 | 4 | 5 | 5 | 5 | |
| | | Day 30 | 7 | 3 | 5 | 4 | 5 | |
| | | Day 60 | 5 | 4 | 5 | 5 | 5 | |

TABLE 29

Canine brief pain index - description of function

| | | | Description of Function: Does Not Interfere (0) → Completely Interferes (10) | | | | | | | Quality of Life in the last 7 days (Poor → Fair → Good → Very Good → Excellent) |
|---|---|---|---|---|---|---|---|---|---|---|
| Patient Number | Name | Date | Pain has interfered with general activity in last 7 days | Pain has interfered with enjoyment of life in last 7 days | Pain has interfered with ability to rise to standing from lying down in last 7 days | Pain has interfered with ability to walk in last 7 days | Pain has interfered with ability to run in last 7 days | Pain has interfered with ability to climb up (stairs, curbs, etc) in last 7 days | Pain Interference Mean | |
| 1 | Gipper Hatch | Day 0 | 7 | 7 | 8 | 6 | 9 | 7 | 7 | Good |
| | | Day 14 | 6 | 5 | 8 | 6 | 9 | 7 | 7 | Good |
| | | Day 30 | 7 | 6 | 8 | 6 | 8 | 8 | 7 | Good |
| | | Day 60 | 7 | 6 | 8 | 6 | 9 | 6 | 7 | Good |
| 2 | Rocco Payne | Day 0 | 6 | 6 | 8 | 8 | 10 | 10 | 8 | Very Good |
| | | Day 14 | 8 | 8 | 7 | 7 | 10 | 10 | 8 | Fair |
| | | Day 30 | 6 | 5 | 6 | 4 | 5 | 10 | 6 | Very Good |
| | | Day 60 | 3 | 2 | 3 | 2 | 7 | 10 | 5 | Very Good |

TABLE 29-continued

Canine brief pain index - description of function

| Patient Number | Name | Date | Description of Function: Does Not Interfere (0) → Completely Interferes (10) | | | | | | | Quality of Life in the last 7 days (Poor → Fair → Good → Very Good → Excellent) |
|---|---|---|---|---|---|---|---|---|---|---|
| | | | Pain has interfered with general activity in last 7 days | Pain has interfered with enjoyment of life in last 7 days | Pain has interfered with ability to rise to standing from lying down in last 7 days | Pain has interfered with ability to walk in last 7 days | Pain has interfered with ability to run in last 7 days | Pain has interfered with ability to climb up (stairs, curbs, etc) in last 7 days | Pain Interference Mean | |
| 3 | Bubba Schlimm | Day 0* | 6 | 3 | 0 | 5 | 9 | 6 | 5 | Good |
| | | Day 0 | 3 | 3 | 3 | 5 | 7 | 5 | 4 | Good |
| | | Day 14 | 3 | 3 | 3 | 3 | 7 | 6 | 4 | Very Good |
| | | Day 30 | 5 | 4 | 4 | 4 | 7 | 4 | 5 | Good |
| | | Day 60 | 2 | 1 | 1 | 2 | 3 | 1 | 2 | Very Good |
| 4 | Aiden Langhans-Lindstadt | Day 0 | 7 | 8 | 7 | 8 | 9 | 8 | 8 | Fair |
| | | Day 14 | 4 | 5 | 5 | 4 | 4 | 5 | 5 | Good |
| | | Day 30 | 4 | 5 | 4 | 5 | 6 | 5 | 5 | Good |
| | | Day 60 | 2 | 4 | 4 | 3 | 3 | 5 | 4 | Good |
| 5 | Moose Baker | Day 0 | 2 | 2 | 2 | 2 | 3 | 4 | 3 | Very Good |
| | | Day 14 | 5 | 3 | 4 | 4 | 6 | 5 | 5 | Good |
| | | Day 30 | 4 | 2 | 5 | 4 | 5 | 5 | 4 | Very Good |
| | | Day 60 | 4 | 3 | 6 | 3 | 5 | 4 | 4 | Good |

*= removed from study

TABLE 30

Full gait data - walks Part 1

| Patient Number | Name | Date | Average TPI (%) Walk | | | | Step Length | | | | Stride Length | | | |
|---|---|---|---|---|---|---|---|---|---|---|---|---|---|---|
| | | | LF | RF | LH | RH | LF | RF | LH | RH | LF | RF | LH | RH |
| 1 | Gipper Hatch | Day 0 | 26.3 | 26.9 | 21.0 | 25.8 | 32.585 | 30.600 | 31.650 | 31.235 | 63.350 | 63.050 | 62.950 | 62.950 |
| | | Day 14 | 26.5 | 26.4 | 21.9 | 25.2 | 29.596 | 30.057 | 27.966 | 31.446 | 59.852 | 59.750 | 59.552 | 59.470 |
| | | Day 30 | 25.7 | 25.7 | 24.1 | 24.3 | 30.842 | 30.824 | 30.386 | 31.619 | 61.683 | 61.683 | 62.036 | 61.930 |
| | | Day 60 | 26.0 | 26.4 | 21.5 | 26.0 | 31.083 | 31.844 | 31.821 | 31.232 | 62.904 | 63.020 | 63.043 | 63.107 |
| 2 | Rocco Payne | Day 0 | 26.4 | 28.8 | 21.8 | 23.0 | 37.714 | 40.795 | 37.246 | 40.751 | 78.778 | 78.553 | 78.040 | 78.148 |
| | | Day 14 | 27.0 | 30.3 | 21.3 | 21.5 | 34.911 | 39.238 | 34.514 | 39.132 | 74.154 | 74.204 | 73.615 | 73.637 |
| | | Day 30 | 28.0 | 30.3 | 19.3 | 22.6 | 32.567 | 37.123 | 34.396 | 34.979 | 69.572 | 69.809 | 69.420 | 69.578 |
| | | Day 60 | 27.4 | 28.9 | 21.6 | 21.9 | 37.370 | 40.368 | 38.088 | 39.272 | 78.098 | 77.798 | 77.221 | 77.432 |
| 3 | Bubba Schlimm | Day 0 | 30.8 | 31.7 | 19.2 | 18.2 | 44.450 | 43.688 | 42.005 | 46.344 | 88.530 | 88.159 | 88.635 | 88.424 |
| | | Day 14 | 31.8 | 31.2 | 18.9 | 18.0 | 41.677 | 42.757 | 40.654 | 43.858 | 84.416 | 84.561 | 84.801 | 84.501 |
| | | Day 30 | 31.4 | 30.7 | 19.3 | 18.5 | 40.255 | 41.444 | 38.424 | 43.342 | 82.028 | 81.598 | 81.936 | 81.936 |
| | | Day 60 | 31.4 | 31.3 | 18.5 | 18.8 | 43.487 | 45.702 | 42.958 | 46.337 | 88.918 | 89.517 | 89.235 | 89.535 |
| 4 | Aiden Langhans-Lindstadt | Day 0 | 31.0 | 32.0 | 18.4 | 18.5 | 57.309 | 56.180 | 58.120 | 56.198 | 113.453 | 113.665 | 114.794 | 114.865 |
| | | Day 14 | 32.6 | 30.3 | 18.4 | 18.8 | 49.939 | 48.789 | 49.346 | 49.054 | 99.272 | 98.407 | 98.460 | 98.037 |
| | | Day 30 | 31.9 | 32.2 | 18.0 | 18.0 | 51.946 | 50.571 | 52.106 | 50.747 | 102.376 | 103.434 | 102.729 | 103.152 |
| | | Day 60 | 32.1 | 30.7 | 18.2 | 18.9 | 50.800 | 50.504 | 51.806 | 50.490 | 101.441 | 101.424 | 102.235 | 102.252 |
| 5 | Moose Baker | Day 0 | 25.1 | 34.4 | 20.9 | 19.5 | 35.285 | 36.647 | 39.741 | 33.669 | 71.522 | 72.390 | 73.152 | 73.766 |
| | | Day 14 | 25.1 | 35.0 | 21.1 | 18.8 | 35.656 | 35.097 | 39.580 | 32.569 | 70.594 | 71.271 | 71.773 | 72.632 |
| | | Day 30 | 24.5 | 35.6 | 19.5 | 20.4 | 35.963 | 36.233 | 39.960 | 32.299 | 72.284 | 72.408 | 72.231 | 72.496 |
| | | Day 60 | 25.1 | 34.4 | 19.5 | 20.8 | 34.491 | 35.909 | 39.317 | 32.427 | 70.242 | 70.792 | 71.671 | 71.893 |

= removed from study

TABLE 31

Full gait data - walks Part 2

| Patient Number | Name | Date | Stance % | | | | Stance Time | | | | Stride/Step | | | |
|---|---|---|---|---|---|---|---|---|---|---|---|---|---|---|
| | | | LF | RF | LH | RH | LF | RF | LH | RH | LF | RF | LH | RH |
| 1 | Gipper Hatch | Day 0 | 64.0 | 68.6 | 57.4 | 60.7 | 0.430 | 0.460 | 0.385 | 0.405 | 51.4 | 48.5 | 50.3 | 49.6 |
| | | Day 14 | 68.2 | 70.1 | 59.6 | 61.2 | 0.449 | 0.460 | 0.392 | 0.400 | 49.4 | 50.3 | 47.0 | 52.9 |
| | | Day 30 | 66.9 | 67.9 | 59.7 | 59.9 | 0.458 | 0.463 | 0.408 | 0.410 | 50.0 | 50.0 | 49.0 | 51.1 |
| | | Day 60 | 67.3 | 68.4 | 58.7 | 60.1 | 0.443 | 0.450 | 0.387 | 0.395 | 49.4 | 50.5 | 50.5 | 49.5 |
| 2 | Rocco Payne | Day 0 | 64.8 | 64.3 | 56.1 | 59.5 | 0.534 | 0.525 | 0.458 | 0.491 | 47.9 | 51.9 | 47.7 | 52.1 |
| | | Day 14 | 66.2 | 65.8 | 57.6 | 61.2 | 0.573 | 0.568 | 0.488 | 0.518 | 47.1 | 52.9 | 46.9 | 53.1 |
| | | Day 30 | 69.3 | 66.4 | 59.0 | 63.5 | 0.682 | 0.653 | 0.579 | 0.628 | 46.8 | 53.2 | 49.5 | 50.3 |
| | | Day 60 | 62.3 | 63.1 | 55.2 | 57.2 | 0.447 | 0.453 | 0.389 | 0.404 | 47.9 | 51.9 | 49.3 | 50.7 |
| 3 | Bubba Schlimm | Day 0 | 60.3 | 61.0 | 57.5 | 57.5 | 0.494 | 0.494 | 0.475 | 0.474 | 50.2 | 49.6 | 47.4 | 52.4 |
| | | Day 14 | 60.4 | 60.2 | 56.4 | 55.0 | 0.453 | 0.451 | 0.421 | 0.411 | 49.4 | 50.6 | 47.9 | 51.9 |

TABLE 31-continued

Full gait data - walks Part 2

| Patient | | | Stance % | | | | Stance Time | | | | Stride/Step | | | |
|---|---|---|---|---|---|---|---|---|---|---|---|---|---|---|
| Number | Name | Date | LF | RF | LH | RH | LF | RF | LH | RH | LF | RF | LH | RH |
| | | Day 30 | 62.6 | 62.6 | 58.9 | 58.4 | 0.534 | 0.535 | 0.501 | 0.500 | 49.1 | 50.8 | 46.9 | 52.9 |
| | | Day 60 | 60.1 | 60.8 | 57.0 | 57.1 | 0.474 | 0.480 | 0.453 | 0.451 | 48.6 | 51.4 | 48.1 | 51.8 |
| 4 | Aiden | Day 0 | 53.9 | 53.7 | 48.4 | 48.5 | 0.330 | 0.331 | 0.297 | 0.296 | 50.5 | 49.4 | 50.6 | 48.9 |
| | Langhans- | Day 14 | 60.6 | 59.9 | 56.6 | 55.2 | 0.446 | 0.445 | 0.417 | 0.410 | 50.3 | 49.6 | 50.1 | 50.0 |
| | Lindstadt | Day 30 | 56.6 | 57.9 | 50.9 | 53.0 | 0.379 | 0.391 | 0.342 | 0.352 | 50.7 | 48.9 | 50.7 | 49.2 |
| | | Day 60 | 57.7 | 58.5 | 53.6 | 53.2 | 0.413 | 0.421 | 0.387 | 0.385 | 49.8 | 50.1 | 49.8 | 50.7 | 49.4 |
| 5 | Moose | Day 0 | 60.1 | 61.4 | 57.7 | 57.7 | 0.405 | 0.413 | 0.388 | 0.384 | 49.3 | 50.6 | 54.3 | 45.6 |
| | Baker | Day 14 | 63.2 | 66.9 | 58.0 | 58.1 | 0.429 | 0.455 | 0.393 | 0.394 | 50.5 | 49.2 | 55.1 | 44.8 |
| | | Day 30 | 61.6 | 59.9 | 56.8 | 57.6 | 0.394 | 0.381 | 0.361 | 0.364 | 49.8 | 50.0 | 55.3 | 44.6 |
| | | Day 60 | 61.0 | 66.8 | 57.7 | 57.7 | 0.407 | 0.446 | 0.388 | 0.385 | 49.1 | 50.7 | 54.9 | 45.1 |

— = removed from study

TABLE 32

Full gait data - trots Part 1

| Patient | | | Average TPI (%) Trot | | | | Step Length | | | | Stride Length | | | |
|---|---|---|---|---|---|---|---|---|---|---|---|---|---|---|
| Number | Name | Date | LF | RF | LH | RH | LF | RF | LH | RH | LF | RF | LH | RH |
| 1 | Gipper | Day 0 | 25.8 | 26.2 | 22.5 | 25.5 | 36.830 | 35.510 | 37.285 | 35.720 | 72.850 | 72.200 | 73.650 | 72.650 |
| | Hatch | Day 14 | 24.8 | 26.3 | 24.0 | 25.0 | 28.776 | 40.279 | 40.868 | 31.082 | 69.208 | 69.918 | 72.262 | 70.561 |
| | | Day 30 | 27.4 | 26.9 | 23.0 | 23.6 | 37.412 | 37.465 | 36.293 | 39.123 | 74.789 | 75.141 | 75.071 | 75.635 |
| | | Day 60 | — | — | — | — | — | — | — | — | — | — | — | — |
| 2 | Rocco | Day 0 | 26.1 | 29.3 | 21.4 | 23.4 | 41.118 | 45.579 | 40.697 | 45.649 | 86.766 | 87.014 | 86.638 | 86.353 |
| | Payne | Day 14 | 27.4 | 27.8 | 21.1 | 24.0 | 43.480 | 45.385 | 41.875 | 47.308 | 89.041 | 88.759 | 89.676 | 88.970 |
| | | Day 30 | 28.0 | 29.1 | 21.5 | 21.6 | 40.030 | 45.014 | 40.993 | 44.715 | 84.861 | 84.861 | 86.078 | 85.707 |
| | | Day 60 | 25.9 | 28.7 | 21.4 | 24.2 | 43.621 | 45.861 | 43.603 | 46.214 | 89.450 | 90.226 | 89.803 | 90.283 |
| 3 | Bubba | Day 0 | 28.8 | 32.5 | 19.9 | 18.9 | 47.096 | 47.766 | 47.413 | 47.272 | 94.474 | 95.391 | 94.827 | 94.827 |
| | Schlimm | Day 14 | 29.4 | 31.9 | 19.7 | 19.0 | 45.741 | 47.149 | 45.314 | 47.879 | 92.498 | 93.271 | 93.049 | 92.932 |
| | | Day 30 | 29.7 | 32.0 | 19.8 | 18.7 | 42.189 | 40.756 | 41.871 | 42.302 | 82.867 | 83.167 | 84.720 | 83.820 |
| | | Day 60 | 31.2 | 33.4 | 17.1 | 18.1 | 46.270 | 44.549 | 45.286 | 46.210 | 91.034 | 91.264 | 91.352 | 91.951 |
| 4 | Aiden | Day 0 | 31.8 | 29.1 | 19.4 | 19.6 | 65.740 | 65.511 | 65.846 | 64.805 | 130.739 | 131.798 | 130.245 | 131.727 |
| | Langhans- | Day 14 | 31.2 | 31.7 | 18.3 | 18.9 | 64.682 | 61.817 | 63.465 | 61.860 | 126.824 | 127.035 | 126.048 | 125.042 |
| | Lindstadt | Day 30 | 31.4 | 29.1 | 19.3 | 20.2 | 63.698 | 62.389 | 63.302 | 61.701 | 126.418 | 126.453 | 125.448 | 125.360 |
| | | Day 60 | 31.2 | 29.8 | 19.4 | 19.5 | 63.236 | 64.929 | 64.950 | 63.712 | 128.605 | 127.970 | 128.958 | 128.993 |
| 5 | Moose | Day 0 | 23.3 | 35.6 | 20.8 | 20.1 | 45.942 | 46.842 | 45.612 | 46.574 | 92.696 | 92.915 | 91.962 | 92.304 |
| | Baker | Day 14 | 23.1 | 36.2 | 20.1 | 20.4 | 46.119 | 48.122 | 44.898 | 48.609 | 94.636 | 94.414 | 94.181 | 93.229 |
| | | Day 30 | 22.1 | 37.2 | 20.3 | 20.3 | 43.110 | 45.164 | 42.968 | 45.254 | 88.688 | 88.357 | 88.399 | 88.554 |
| | | Day 60 | 23.7 | 36.2 | 19.9 | 20.1 | 43.808 | 47.159 | 43.102 | 47.773 | 91.250 | 91.017 | 91.006 | 91.027 |

— = removed from study

TABLE 33

Full gait data - trots Part 2

| Patient | | | Stance % | | | | Stance Time | | | | Step/Stride Ratio | | | |
|---|---|---|---|---|---|---|---|---|---|---|---|---|---|---|
| Number | Name | Date | LF | RF | LH | RH | LF | RF | LH | RH | LF | RF | LH | RH |
| 1 | Gipper | Day 0 | 60.4 | 62.6 | 51.0 | 53.2 | 0.330 | 0.345 | 0.280 | 0.295 | 50.6 | 49.2 | 50.6 | 49.2 |
| | Hatch | Day 14 | 55.3 | 61.6 | 55.1 | 51.7 | 0.265 | 0.286 | 0.245 | 0.241 | 41.6 | 57.6 | 56.6 | 44.1 |
| | | Day 30 | 60.0 | 61.4 | 49.4 | 50.4 | 0.334 | 0.341 | 0.276 | 0.282 | 50.0 | 49.9 | 48.3 | 51.7 |
| | | Day 60 | — | — | — | — | — | — | — | — | — | — | — | — |
| 2 | Rocco | Day 0 | 58.3 | 57.5 | 47.8 | 50.1 | 0.371 | 0.370 | 0.306 | 0.319 | 47.4 | 52.4 | 47.0 | 52.9 |
| | Payne | Day 14 | 55.8 | 55.8 | 43.3 | 45.3 | 0.350 | 0.352 | 0.279 | 0.284 | 48.8 | 51.1 | 46.7 | 53.2 |
| | | Day 30 | 59.4 | 57.4 | 47.9 | 50.0 | 0.382 | 0.376 | 0.314 | 0.332 | 47.2 | 52.8 | 47.6 | 52.2 |
| | | Day 60 | 53.3 | 52.3 | 41.7 | 44.2 | 0.301 | 0.296 | 0.243 | 0.255 | 48.8 | 50.8 | 48.6 | 51.2 |
| 3 | Bubba | Day 0 | 50.5 | 49.4 | 44.0 | 43.3 | 0.295 | 0.286 | 0.269 | 0.261 | 49.9 | 50.1 | 50.0 | 49.9 |
| | Schlimm | Day 14 | 50.9 | 50.4 | 42.3 | 42.1 | 0.290 | 0.285 | 0.245 | 0.243 | 49.5 | 50.6 | 48.7 | 51.5 |
| | | Day 30 | 53.6 | 55.1 | 48.5 | 50.1 | 0.337 | 0.350 | 0.315 | 0.327 | 50.9 | 49.0 | 49.4 | 50.5 |
| | | Day 60 | 53.7 | 54.9 | 49.9 | 48.3 | 0.333 | 0.341 | 0.314 | 0.302 | 50.0 | 48.8 | 49.6 | 50.3 |
| 4 | Aiden | Day 0 | 45.0 | 44.0 | 40.1 | 39.0 | 0.241 | 0.235 | 0.215 | 0.208 | 50.3 | 49.7 | 50.6 | 49.2 |
| | Langhans- | Day 14 | 44.5 | 43.8 | 38.5 | 38.5 | 0.228 | 0.226 | 0.199 | 0.199 | 51.0 | 48.7 | 50.3 | 49.5 |
| | Lindstadt | Day 30 | 46.4 | 46.0 | 39.0 | 38.8 | 0.259 | 0.255 | 0.213 | 0.210 | 50.4 | 49.3 | 50.5 | 49.2 |
| | | Day 60 | 44.4 | 45.1 | 37.7 | 38.1 | 0.241 | 0.249 | 0.203 | 0.207 | 49.2 | 50.7 | 50.4 | 49.4 |

TABLE 33-continued

Full gait data - trots Part 2

| Patient | | | Stance % | | | | Stance Time | | | | Step/Stride Ratio | | | |
|---|---|---|---|---|---|---|---|---|---|---|---|---|---|---|
| Number | Name | Date | LF | RF | LH | RH | LF | RF | LH | RH | LF | RF | LH | RH |
| 5 | Moose Baker | Day 0 | 44.7 | 48.2 | 42.9 | 42.5 | 0.214 | 0.232 | 0.205 | 0.203 | 49.6 | 50.4 | 49.6 | 50.5 |
| | | Day 14 | 43.5 | 47.8 | 43.3 | 42.9 | 0.203 | 0.221 | 0.203 | 0.197 | 48.7 | 51.0 | 47.7 | 52.1 |
| | | Day 30 | 47.5 | 50.5 | 44.7 | 45.5 | 0.228 | 0.245 | 0.215 | 0.220 | 48.6 | 51.1 | 48.6 | 51.1 |
| | | Day 60 | 46.3 | 49.8 | 42.7 | 45.2 | 0.223 | 0.243 | 0.204 | 0.217 | 48.0 | 51.8 | 47.4 | 52.5 |

= removed from study

TABLE 34

Gait analysis summary

| Dog 1 | Dog 2 | Dog 3 | Dog 4 | Dog 5 |
|---|---|---|---|---|
| Walk | Walk | Walk | Walk | Walk |
| Step/Stride - declined Day 14, improved day 60 | Step/Stride - improves day 30 & 60 | Step/Stride - Declined day 60 | Step/Stride - Unchanged | Step/Stride - Unchanged |
| Stance % - improved day 14, 30, and 60 | Stance % - declined day 30, improved day 60 | Stance % - unchanged | Stance % - slightly declined day 14, 30 | Stance % - decline day 14, 60 |
| Trot | Trot | Trot | Trot | Trot |
| Step/Stride - declined day 14 (no day 60 data) | Step/Stride - slowly improved at each recheck | Step/Stride - Unchanged, (slightly declined) | Step/Stride - Unchanged | Step/Stride - slightly declined at each recheck |
| Stance % - Declined day 14, slightly improved day 30 (no day 60 data) | Stance % - declined day 30 | Stance % - slightly declined day 30, 60 | Stance % - slightly improved day 14, 30, 60 | Stance % - forelimbs slight improve day 30 but hindlimb declined, declined day 60 |

Example 14

Feline Safety Study

A 12-week safety study was performed in felines to evaluate the safety of an oil containing CBD.

Animals and Study Design

Eight cats, 2-6 years old, weighing 3.33-5.17 kg at study start were selected for the study, as shown in Table 35.

TABLE 35

Animal information

| Cat ID | Sex | Date of Birth |
|---|---|---|
| 15EGA5 | FS | Apr. 8, 2015 |
| 13IRD3 | FS | Oct. 5, 2013 |
| 15KGA2 | FS | Apr. 7, 2015 |
| 13CNL3 | MC | May 20, 2013 |
| 13CCL1 | MC | Feb. 11, 2013 |
| GJY3 | MC | Jul. 17, 2011 |
| 15KGC3 | MC | Apr. 8, 2015 |
| 13CPJ7 | FS | Oct. 25, 2013 |

Cats were single housed in cages of a size in accordance with the Animal Welfare Act, with a 12-hour-light/12-hour-dark cycle and targeted conditions of 50° to 85° F. Cages, food bowls, water bowls and litter boxes were cleaned daily and sanitized in accordance with the Animal Welfare Act. Fresh tap water, fit for human consumption, was available ad libitum by means of stainless steel bowls. There were no known contaminants that were reasonably expected to be present in the dietary material that were known to be capable of interfering with the purpose or conduct of the study During the study, the control diet, Purina Cat Chow, was the sole source of food supplied to each animal once daily for approximately 4 hours. Cats were fed according to ideal body condition and were fasted for a minimum of 12 hours prior to blood collections. CBD oil was orally administered twice a day using a 1 ml syringe at a dosage of 2 mg/kg. The total dose per 24 hour period was 4 mg/kg. Dosing is shown in Tables 36 and 37.

TABLE 36

Dosage per week (mL) (weeks 1-6)

| | | Week | | | | | |
|---|---|---|---|---|---|---|---|
| Cat ID | Sex | 1 | 2 | 3 | 4 | 5 | 6 |
| 15EGA5 | FS | 0.14 | 0.14 | 0.14 | 0.15 | 0.14 | 0.14 |
| 13IRD3 | FS | 0.13 | 0.14 | 0.14 | 0.14 | 0.14 | 0.14 |
| 15KGA2 | FS | 0.13 | 0.14 | 0.14 | 0.14 | 0.14 | 0.14 |
| 13CNL3 | MC | 0.19 | 0.19 | 0.19 | 0.19 | 0.19 | 0.19 |
| 13CCL1 | MC | 0.20 | 0.20 | 0.20 | 0.20 | 0.21 | 0.20 |
| GJY3 | MC | 0.21 | 0.22 | 0.22 | 0.22 | 0.23 | 0.23 |
| 15KGC3 | MC | 0.19 | 0.20 | 0.21 | 0.21 | 0.21 | 0.21 |
| 13CPJ7 | FS | 0.15 | 0.15 | 0.15 | 0.15 | 0.16 | 0.16 |

TABLE 37

Dosage per week (mL) (weeks 7-12)

| Cat ID | Sex | Week | | | | | |
|---|---|---|---|---|---|---|---|
| | | 7 | 8 | 9 | 10 | 11 | 12 |
| 15EGA5 | FS | 0.14 | 0.14 | 0.14 | 0.14 | 0.14 | 0.13 |
| 13IRD3 | FS | 0.14 | 0.14 | 0.14 | 0.14 | 0.13 | 0.13 |
| 15KGA2 | FS | 0.14 | 0.14 | 0.14 | 0.14 | 0.14 | 0.13 |
| 13CNL3 | MC | 0.19 | 0.19 | 0.19 | 0.19 | 0.19 | 0.19 |
| 13CCL1 | MC | 0.21 | 0.20 | 0.20 | 0.20 | 0.19 | 0.19 |
| GJY3 | MC | 0.23 | 0.23 | 0.23 | 0.23 | 0.23 | 0.22 |
| 15KGC3 | MC | 0.21 | 0.21 | 0.21 | 0.21 | 0.21 | 0.21 |
| 13CPJ7 | FS | 0.16 | 0.15 | 0.15 | 0.15 | 0.15 | 0.15 |

CBC and Serum Chemistry

Prior to study initiation, 5 milliliters of blood was collected for each cat and was used to determine eligibility for the study. During the study, 5 milliliters of blood was collected weekly (±2 days). Blood was collected via jugular venipuncture in sterile syringes. Samples were split into two tubes: a red-top serum separator tube and a lavender-top EDTA tube. Redtop tubes were spun in a refrigerated centrifuge for 15 minutes at 3000 RPM after being allowed to clot. Lavender-top tubes were placed on a rocker to allow the blood to adequately mix with the anticoagulant. Blood samples were packaged and sent by priority-overnight to Antech Diagnostics for analysis.

Pharmacokinetic (PK) Blood Collection

On the first day of dosing, blood was collected for a PK analysis from 6 of the 8 cats. The most cooperative cats were selected for the PK analysis. Approximately 4 milliliters of blood was collected via jugular venipuncture in sterile syringes at one day prior to treatment (timepoint 0) and then 1, 4, 8 and 24 hours after treatment. Samples were placed into a red top clotting tube with no serum separator. Serum was harvested by centrifuging the tubes at 3000 RPM for 15 minutes. The harvested serum was placed in cyrovials stored at −70° C. Each tube was labeled with the cat id, date of collection and collection time point. Samples were shipped overnight on dry ice to the Proteomics & Metabolomics Facility at Colorado State University.

Clinical Observations

A veterinarian performed a complete physical examination to all cats prior to the initiation of the study and at study completion. Each cat was evaluated as to general health, body and hair coat condition. Qualified personnel performed clinical observations twice daily in accordance with Summit Ridge Farms' Program of Veterinary Care and SOP VC-003 (Rounds Observations). All animals were evaluated twice daily with reference to SOP VC-016 (Recognizing Pain, Stress and/or Distress). Clinical laboratory diagnostic procedures were performed as needed. Veterinary care was given as appropriate to each individual animal in accordance with the Program of Veterinary Care.

Blood Analysis

Blood was analyzed for white blood cell count, red blood cell count, hemoglobin, hematocrit, MCV, MCHC, MCH, and platelet count along with a complete differential. In addition, a 22-test chemistry screen was performed consisting of Glucose, Urea Nitrogen, Creatinine, Total Protein, Albumin, Total Bilirubin, Alkaline Phosphatase, ALT, AST, CPK, Cholesterol, Calcium, Phosphorus, Sodium, Potassium, Chloride, NG Ratio, BUN/Creatinine Ratio, Globulin, Triglycerides, GGTP and Magnesium. Measurements were taken prior to the start of the study and then weekly during the course of the study.

PK Analysis

Extraction of Cannabidiol from Feline serum for LC-MS

Aliquots of feline serum were delivered to the facility on dry ice and stored at −80° C. upon receipt. For cannabidiol (CBD) extraction, serum was thawed on ice and 50 μL of each sample was placed into a 2.0 ml glass extraction vial (VWR ROBO Unassembled Autosampler Vial) kept on chilled on ice. 200 μL of cold (−20 C) 100% Acetonitrile (spiked with 60 ng/mL of d3-CBD) was added to each sample and vortexed at room temperature for 5 minutes. 200 μL of water was added and vortexed for an additional 5 minutes. 1 ml of 100% hexane was then added to each sample and vortexed for a final 5 minutes. Phase separation was enhanced under centrifugation at 3000 rpm for 15 minutes at 4 C. The upper hexane layer was transferred to new-labeled glass vials (~900 uL per sample), carefully avoiding the middle and lower layers. Samples were concentrated to dryness under N2 and resuspended in 60 μL of 100% acetonitrile.

Standard Curve

An 8 point standard curve of CBD was generated in matrix background using a blank serum. Concentrations ranged from 0 ng/mL 1000 ng/mL (3.2× dilution series). 50 uL of each spiked serum sample was extracted as above.

LC-MS/MS Analysis

LC-MS/MS was performed on a Waters Acquity M-Class UPLC coupled to a Waters Xevo TQ-S triple quadrupole mass spectrometer. Chromatographic separations were carried out on a Waters BEH C18 iKey Separation Device (150 μm×50 mm, 1.7 μM). Mobile phases were 99.9% acetonitrile, 0.1% formic acid (B) and water with 0.1% formic acid (A). The analytical gradient was as follows: time=0 min, 70% B; time=1.0 min, 70% B; time=6 min, 100% B; time 7.0 min, 100% B; time 7.5 min, 70% B. Total run time was 10 minutes. Flow rate was 3.0 μL/min and injection volume was 2.0 μL. Samples were held at 6° C. in the autosampler, and the column was operated at 70° C. The MS was operated in selected reaction monitoring (SRM) mode, where a parent ion is selected by the first quadrupole, fragmented in the collision cell, then a fragment ion selected for by the third quadrupole. Product ions, collision energies, and cone voltages were optimized for each analyte by direct injection of individual synthetic standards. Inter-channel delay was set to 3 ms. The MS was operated in positive ionization mode with the capillary voltage set to 3.6 kV. Source temperature was 120° C. and desolvation temperature 992° C. Desolvation gas flow was 1 L/hr, cone gas flow was 150 L/hr, and collision gas flow was 0.2 mL/min. Nebulizer pressure (nitrogen) was set to 7 Bar. Argon was used as the collision gas.

Data Analysis and Statistics

All Raw data files were imported into the Skyline open source software package. Each target analyte was visually inspected for retention time and peak area integration. Peak areas were extracted for target compounds detected in biological samples and normalized to the peak area of the appropriate internal standard in each sample using in-house R Script (TQS-tools). CBD concentrations were calculated in nanograms per milliliter of extract (0.06 mL) and then back calculated to nanograms per mL of serum (0.05 mL of serum).

Calculation of Variance using QC Pool 50 uL of all serum samples (feline and canine) were pooled into a single Quality Control sample and 50 uL was extracted as described above. The QC pool was injected every 10 samples and CBD concentrations were used to measure the technical variance over the course of data acquisition.

Limits of Detection (LOD) and Limits of Quantification (LOQ)

The LOD and LOQ represent the lower limits of detection and quantification for each compound in the matrix of this study. LOD are calculated based on the standard deviation of the response (Sy) of the 0 point calibration standard (i.e. 0 ng/mL CBD as an estimate on noise) and the slope of the calibration curve (S) at levels approximating the LOD according to the formula: LOD=3*(Sy/S). LOQ=10*(Sy/S). The Sy of y is the standard deviation used for LOD and LOQ calculation.

Results

Body Weight

The mean average weight change for cats during the 12 weeks of the study was 0.06 kg (1.04%). Weight data is presented in Tables 38 and 39.

TABLE 38

Weekly body weights (weeks 1-6)

| Cat ID | Sex | Base | 1 | 2 | 3 | 4 | 5 | 6 |
|---|---|---|---|---|---|---|---|---|
| 15EGA5 | FS | 3.43 | 3.60 | 3.62 | 3.76 | 3.62 | 3.60 | 3.62 |
| 13IRD3 | FS | 3.34 | 3.48 | 3.61 | 3.61 | 3.48 | 3.51 | 3.52 |
| 15KGA2 | FS | 3.33 | 3.42 | 3.48 | 3.51 | 3.53 | 3.53 | 3.49 |
| 13CNL3 | MC | 4.66 | 4.63 | 4.70 | 4.81 | 4.82 | 4.81 | 4.78 |
| 13CCL1 | MC | 5.03 | 5.01 | 5.00 | 5.11 | 5.14 | 5.07 | 5.19 |
| GJY3 | MC | 5.17 | 5.53 | 5.55 | 5.57 | 5.63 | 5.64 | 5.67 |
| 15KGC3 | MC | 4.82 | 5.11 | 5.21 | 5.18 | 5.27 | 5.26 | 5.31 |
| 13CPJ7 | FS | 3.72 | 3.73 | 3.86 | 3.87 | 3.93 | 3.92 | 3.92 |
| Mean: | | 4.19 | 4.31 | 4.38 | 4.43 | 4.43 | 4.42 | 4.44 |
| SD: | | 0.806 | 0.849 | 0.828 | 0.824 | 0.880 | 0.871 | 0.898 |

TABLE 39

Weekly body weights (weeks 7-12)

| Cat ID | Sex | 7 | 8 | 9 | 10 | 11 | 12 | Chg. | % Chg. |
|---|---|---|---|---|---|---|---|---|---|
| 15EGA5 | FS | 3.50 | 3.51 | 3.49 | 3.38 | 3.37 | 3.33 | −0.10 | −2.92 |
| 13IRD3 | FS | 3.46 | 3.42 | 3.38 | 3.36 | 3.27 | 3.25 | −0.09 | −2.69 |
| 15KGA2 | FS | 3.43 | 3.43 | 3.40 | 3.39 | 3.34 | 3.37 | 0.04 | 1.20 |
| 13CNL3 | MC | 4.78 | 4.82 | 4.82 | 4.84 | 4.80 | 4.83 | 0.17 | 3.65 |
| 13CCL1 | MC | 4.99 | 4.96 | 4.96 | 4.87 | 4.85 | 4.74 | −0.29 | −5.77 |
| GJY3 | MC | 5.67 | 5.67 | 5.69 | 5.71 | 5.55 | 5.50 | 0.33 | 6.38 |
| 15KGC3 | MC | 5.35 | 5.33 | 5.29 | 5.21 | 5.15 | 5.11 | 0.29 | 6.02 |
| 13CPJ7 | FS | 3.87 | 3.86 | 3.82 | 3.81 | 3.80 | 3.81 | 0.09 | 2.42 |
| Mean: | | 4.38 | 4.38 | 4.36 | 4.32 | 4.27 | 4.24 | 0.06 | 1.04 |
| SD: | | 0.920 | 0.922 | 0.936 | 0.943 | 0.920 | 0.902 | 0.210 | 4.439 |

Food Consumption

The Mean Daily Food Consumption Per Week for Cats During the Study was 62 g. Food Consumption Data Is Presented in Tables 40 and 41.

TABLE 40

Average daily food consumption per week (weeks 1-6)

| Cat ID | Sex | 1 | 2 | 3 | 4 | 5 | 6 |
|---|---|---|---|---|---|---|---|
| 15EGA5 | FS | 70 | 70 | 65 | 56 | 55 | 55 |
| 13IRD3 | FS | 70 | 70 | 60 | 51 | 50 | 50 |
| 15KGA2 | FS | 70 | 70 | 65 | 61 | 55 | 50 |
| 13CNL3 | MC | 62 | 59 | 65 | 65 | 64 | 64 |
| 13CCL1 | MC | 75 | 70 | 87 | 54 | 64 | 69 |
| GJY3 | MC | 100 | 100 | 95 | 86 | 80 | 75 |
| 15KGC3 | MC | 100 | 98 | 92 | 93 | 89 | 82 |
| 13CPJ7 | FS | 70 | 70 | 68 | 66 | 60 | 55 |
| Mean: | | 77 | 76 | 75 | 67 | 64 | 63 |
| SD: | | 14.6 | 14.8 | 14.2 | 15.3 | 13.3 | 12.0 |

TABLE 41

Average daily food consumption per week (weeks 6-12)

| Cat ID | Sex | 7 | 8 | 9 | 10 | 11 | 12 | Average |
|---|---|---|---|---|---|---|---|---|
| 15EGA5 | FS | 51 | 50 | 50 | 50 | 50 | 50 | 56 |
| 13IRD3 | FS | 46 | 45 | 45 | 45 | 45 | 45 | 52 |
| 15KGA2 | FS | 50 | 50 | 50 | 50 | 50 | 50 | 56 |
| 13CNL3 | MC | 64 | 65 | 62 | 64 | 61 | 61 | 63 |
| 13CCL1 | MC | 63 | 54 | 75 | 61 | 42 | 54 | 64 |
| GJY3 | MC | 71 | 66 | 65 | 55 | 45 | 45 | 74 |
| 15KGC3 | MC | 76 | 66 | 64 | 60 | 60 | 60 | 78 |
| 13CPJ7 | FS | 51 | 50 | 50 | 50 | 49 | 50 | 57 |
| Mean: | | 59 | 56 | 58 | 54 | 50 | 52 | 62 |
| SD: | | 11.2 | 8.5 | 10.3 | 6.7 | 6.8 | 6.2 | 9.3 |

Test Article Acceptance

Overall all cats exhibited behaviors of licking, salivating, pacing, head shaking, chomping, dose resentment (uncooperative behavior), etc. at various intervals throughout the study that were indicative of dislike of the test article. Results are shown in Tables 42-69.

TABLE 42

Observations following test article administration (days 1-3)

| | Day 1 | | Day 2 | | Day 3 | |
|---|---|---|---|---|---|---|
| Cat Id | AM | PM | AM | PM | AM | PM |
| 15EGA5 | chomping, white foamy mouth | licking | licking | licking | licking, chomping | licking |
| 13IRD3 | chomping, salivating | licking, head shake, drooling | head shake, licking | chomping | licking, chomping | head shake |
| 15KGA2 | chomping, salivating | licking | licking | licking | licking, chomping | licking |
| 13CNL3 | licking | licking, head shake, foaming | heads shake, licking | — | head shake, licking | head shake |
| 13CCL1 | chomping, head shake, salivating | licking, chomping | licking | chomping, salivating | chomping, salivating | — |
| GJY3 | chomping | licking, chomping | head shake, licking | licking | licking | head shake |
| 15KGC3 | chomping | licking | licking | licking | head shake, grimace | licking |
| 13CP17 | chomping, pacing | pacing, chomping, licking | licking, pacing | licking, pacing | pacing | pacing |

— denotes no reaction recorded

TABLE 43

Observations following test article administration (days 4-6)

| | Day 4 | | Day 5 | | Day 6 | |
|---|---|---|---|---|---|---|
| Cat Id | AM | PM | AM | AM | AM | PM |
| 15EGA5 | drooling | licking | licking | head shake | head shake | — |
| 13IRD3 | — | chomping | — | — | licking | chewing |
| 15KGA2 | very relaxed | chomping | — | licking | licking | — |
| 13CNL3 | pacing | — | — | — | — | little head shake |
| 13CCL1 | pacing | chomping | — | chomping | chomping | — |
| GJY3 | licking | licking | licking | — | licking | licking |
| 15KGC3 | — | licking | chomping | licking | — | — |
| 13CP17 | pacing | pacing | pacing | pacing | pacing | pacing |

— denotes no reaction recorded

TABLE 44

Observations following test article administration (days 7-9)

| | Day 7 | | Day 8 | | Day 9 | |
|---|---|---|---|---|---|---|
| Cat Id | AM | PM | AM | PM | AM | PM |
| 15EGA5 | head shake | head shake | head shake | head shake | licking | licking |
| 13IRD3 | — | — | — | licking | head shake | — |
| 15KGA2 | — | chewing | — | licking | chomping | — |
| 13CNL3 | — | — | — | head shake | — | — |
| 13CCL1 | head shake | head shake | licking | — | — | chomping |
| GJY3 | licking | licking | — | — | — | licking |
| 15KGC3 | licking | licking/head shake | licking | — | head shake | — |
| 13CPJ7 | pacing | pacing | pacing | pacing | pacing | pacing |

— denotes no reaction recorded

TABLE 45

Observations following test article administration (days 10-12)

| | Day 10 | | Day 11 | | Day 12 | |
|---|---|---|---|---|---|---|
| Cat Id | AM | PM | AM | PM | AM | PM |
| 15EGA5 | — | licking | — | head shake | chomping | licking |
| 13IRD3 | — | — | — | — | — | — |
| 15KGA2 | — | — | — | head shake | licking | — |

TABLE 45-continued

Observations following test article administration (days 10-12)

| | Day 10 | | Day 11 | | Day 12 | |
|---|---|---|---|---|---|---|
| Cat Id | AM | PM | AM | PM | AM | PM |
| 13CNL3 | licking | licking | — | licking | — | — |
| 13CCL1 | — | — | head shake | — | head shake | head shake |
| GJY3 | — | — | — | licking | — | — |
| 15KGC3 | head shake | licking | — | — | licking | licking |
| 13CP17 | pacing | pacing | pacing | pacing | pacing | pacing |

— denotes no reaction recorded

TABLE 46

Observations following test article administration (days 13-15)

| | Day 13 | | Day 14 | | Day 15 | |
|---|---|---|---|---|---|---|
| Cat Id | AM | PM | AM | PM | AM | PM |
| 15EGA5 | — | — | head shake | licking | chomping | licking |
| 13IRD3 | licking | — | — | — | — | — |
| 15KGA2 | licking | licking | chomping | — | chomping | licking |
| 13CNL3 | — | — | — | chomping | — | — |
| 13CCL1 | — | — | food vomit before dosing | — | — | — |
| GJY3 | licking | — | hairball vomit before dosing | licking | — | — |
| 15KGC3 | licking | head shake | — | — | — | — |
| 13CPJ7 | pacing | pacing | pacing | — | pacing | pacing |

— denotes no reaction recorded

TABLE 47

Observations following test article administration (days 16-18)

| | Day 16 | | Day 17 | | Day 18 | |
|---|---|---|---|---|---|---|
| Cat Id | AM | PM | AM | PM | AM | PM |
| 15EGA5 | chomping, licking | — | head shake | licking | licking | licking |
| 13IRD3 | — | — | licking | — | salivating before dosing | — |
| 15KGA2 | licking | licking | head shake, licking | — | — | — |
| 13CNL3 | — | — | — | licking | hairball vomit before dosing | — |
| 13CCL1 | — | — | — | — | — | — |
| GJY3 | licking | licking | — | — | — | licking |
| 15KGC3 | — | — | head shake | head shake | head shake | — |
| 13CPJ7 | pacing | pacing | chomping | licking | — | pacing |

— denotes no reaction recorded

TABLE 48

Observations following test article administration (days 19-21)

| | Day 19 | | Day 20 | | Day 21 | |
|---|---|---|---|---|---|---|
| Cat Id | AM | PM | AM | PM | AM | PM |
| 15EGA5 | — | — | head shake | licking | head shake | head shake |
| 13IRD3 | — | — | — | — | — | — |
| 15KGA2 | — | chomping | chomping | chomping | licking | licking |
| 13CNL3 | — | — | — | — | licking | — |
| 13CCL1 | — | — | — | — | — | — |
| GJY3 | — | licking | licking | — | licking | licking |
| 15KGC3 | head shake | head shake | licking | head shake | head shake | head shake |
| 13CP17 | — | pacing | head shake | pacing | pacing | pacing |

— denotes no reaction recorded

TABLE 49

Observations following test article administration (days 22-24)

| | Day 22 | | Day 23 | | Day 24 | |
|---|---|---|---|---|---|---|
| Cat Id | AM | PM | AM | PM | AM | PM |
| 15EGA5 | licking | — | licking | — | licking | head shake |
| 13IRD3 | — | — | — | — | — | — |
| 15KGA2 | — | licking | head shake | — | head shake | licking |
| 13CNL3 | — | — | head shake | head shake | head shake | — |
| 13CCL1 | licking, head shake | — | — | chomping | — | uncooperative, l;icking |
| GJY3 | — | head shake | licking | licking | — | — |
| 15KGC3 | head shake | head shake | licking | — | licking | — |
| 13CPJ7 | pacing | pacing | head shake | — | pacing | pacing |

— denotes no reaction recorded

TABLE 50

Observations following test article administration (days 25-27)

| | Day 25 | | Day 26 | | Day 27 | |
|---|---|---|---|---|---|---|
| Cat Id | AM | PM | AM | PM | AM | PM |
| 15EGA5 | licking | — | licking | — | head shake | licking |
| 13IRD3 | — | — | head shake | licking | — | licking |
| 15KGA2 | licking | licking | — | licking | — | licking |
| 13CNL3 | licking | licking | licking | — | licking | — |
| 13CCL1 | head shake | head shake | — | chomping | head shake | — |
| GJY3 | — | — | licking | licking | licking, head shake | licking |
| 15KGC3 | — | — | head shake, licking | head shake | licking | head shake, licking |
| 13CPJ7 | pacing | pacing | pacing | pacing | pacing | pacing |

— denotes no reaction recorded

TABLE 51

Observations following test article administration (days 28-30)

| | Day 28 | | Day 29 | | Day 30 | |
|---|---|---|---|---|---|---|
| Cat Id | AM | PM | AM | PM | AM | PM |
| 15EGA5 | licking | — | — | — | licking, head shake | licking |
| 13IRD3 | — | — | — | licking | — | licking |
| 15KGA2 | — | head shake | — | licking | — | licking |
| 13CNL3 | — | — | head shake | head shake | licking | — |
| 13CCL1 | licking | head shake, licking | licking | — | — | — |
| GJY3 | licking | — | licking | licking, head shake | — | licking |
| 15KGC3 | — | licking, head shake | head shake, licking | licking | licking | head shake |
| 13CPJ7 | pacing | pacing | pacing | pacing | head shake, pacing | pacing |

— denotes no reaction recorded

TABLE 52

Observations following test article administration (days 31-33)

| | Day 31 | | Day 32 | | Day 33 | |
|---|---|---|---|---|---|---|
| Cat Id | AM | PM | AM | PM | AM | PM |
| 15EGA5 | head shake | licking | head shake | head shake | head shake, licking | licking |
| 13IRD3 | head shake | — | — | licking | — | head shake |
| 15KGA2 | — | — | chomping, licking | — | chomping | licking |
| 13CNL3 | licking | head shake | licking | licking | — | — |
| 13CCL1 | — | licking | — | — | — | head shake |
| GJY3 | licking | licking | — | licking | licking | — |
| 15KGC3 | licking, chomping | head shake | head shake | head shake, licking | — | head shake |
| 13CPJ7 | head shake | pacing | head shake | pacing | pacing | pacing |

— denotes no reaction recorded

TABLE 53

Observations following test article administration (days 79-81)

| Cat Id | Day 34 AM | Day 34 PM | Day 35 AM | Day 35 PM | Day 36 AM | Day 36 PM |
|---|---|---|---|---|---|---|
| 15EGA5 | licking | licking | licking | — | — | chomping |
| 13IRD3 | — | — | head shake | — | — | — |
| 15KGA2 | chomping, licking | licking | — | chomping | chomping, licking | — |
| 13CNL3 | — | — | — | — | head shake | — |
| 13CCL1 | — | — | licking | licking | — | — |
| GJY3 | — | licking | — | licking | — | — |
| 15KGC3 | licking | licking | — | licking | — | licking |
| 13CPJ7 | pacing | pacing | pacing | licking | pacing | pacing |

— denotes no reaction recorded

TABLE 54

Observations following test article administration (days 37-39)

| Cat Id | Day 37 AM | Day 37 PM | Day 38 AM | Day 38 PM | Day 39 AM | Day 39 PM |
|---|---|---|---|---|---|---|
| 15EGA5 | chomping | head shake | licking | licking | licking | head shake, licking |
| 13IRD3 | — | — | head shake | — | — | — |
| 15KGA2 | licking | licking | — | licking, head shake | — | licking |
| 13CNL3 | uncooperative | head shake | jumping, licking | — | jumping, licking | licking |
| 13CCL1 | uncooperative | — | — | drooling, head shake | — | head shake, licking |
| GJY3 | — | licking | — | — | — | jumping |
| 15KGC3 | uncooperative | licking | head shake, licking | head shake | head shake, licking | head shake, licking |
| 13CPJ7 | pacing | pacing | pacing | pacing | pacing | pacing |

— denotes no reaction recorded

TABLE 55

Observations following test article administration (days 40-42)

| Cat Id | Day 40 AM | Day 40 PM | Day 41 AM | Day 41 PM | Day 42 AM | Day 42 PM |
|---|---|---|---|---|---|---|
| 15EGA5 | head shake, licking | chomping, licking | — | licking | — | — |
| 13IRD3 | — | — | licking | drooling | licking | — |
| 15KGA2 | chomping | licking | — | — | — | head shake |
| 13CNL3 | — | — | jumping, head shake | head shake | licking | jumping, licking |
| 13CCL1 | — | — | head shake | — | head shaking, jumping | gagging |
| GJY3 | — | — | head shake | licking | licking | licking |
| 15KGC3 | head shake, licking | head shake, licking | head shake, licking | licking | — | head shake, licking |
| 13CPJ7 | pacing | pacing | pacing | pacing | pacing | pacing, head shake |

— denotes no reaction recorded

TABLE 56

Observations following test article administration (days 43-45)

| Cat Id | Day 43 AM | Day 43 PM | Day 44 AM | Day 44 PM | Day 45 AM | Day 45 PM |
|---|---|---|---|---|---|---|
| 15EGA5 | chomping, licking | chomping, licking | head shake, licking | licking | chewing | chewing |
| 13IRD3 | — | — | — | — | — | — |
| 15KGA2 | head shake, licking | head shake | licking | head shake, chomping | head shake, chewing | — |
| 13CNL3 | — | — | — | — | head shake | head shake |
| 13CCL1 | — | gagging | food vomit before dosing | — | head shake | head shake |
| GJY3 | licking | licking | — | — | licking | a little chewing |
| 15KGC3 | head shake, licking, chomping | licking | head shake, licking | head shake | licking | head shake |
| 13CPJ7 | pacing | pacing | pacing | pacing | pacing | pacing |

— denotes no reaction recorded

TABLE 57

Observations following test article administration (days 46-48)

| Cat Id | Day 46 AM | Day 46 PM | Day 47 AM | Day 47 PM | Day 48 AM | Day 48 PM |
|---|---|---|---|---|---|---|
| 15EGA5 | licking, chomping | — | licking, head shake | licking | licking | head shake, licking |
| 13IRD3 | — | — | — | — | — | drooling |
| 15KGA2 | licking | licking | head shake, chewing | chomping | chewing, head shake | licking |
| 13CNL3 | — | — | licking | — | licking | — |
| 13CCL1 | head shake | licking, chewing | — | — | head shake | — |
| GJY3 | licking | head shake | — | licking | — | licking |
| 15KGC3 | head shake, licking | — | head shake | — | licking | licking |
| 13CPJ7 | pacing, head shake | pacing | pacing | pacing | head shake, pacing | pacing |

— denotes no reaction recorded

TABLE 58

Observations following test article administration (days 49-51)

| Cat Id | Day 49 AM | Day 49 PM | Day 50 AM | Day 50 PM | Day 51 AM | Day 51 PM |
|---|---|---|---|---|---|---|
| 15EGA5 | licking | licking | licking, head shake | licking, head shake | head shake, chomping | licking |
| 13IRD3 | — | — | — | — | head shake | — |
| 15KGA2 | licking | licking | licking | — | head shake | licking |
| 13CNL3 | licking | head shake | — | head shake | — | licking |
| 13CCL1 | licking | head shake | salivating | — | — | gagging |
| GJY3 | head shake | licking | head shake | — | licking | head shake, licking |
| 15KGC3 | licking, head shake | head shake, licking | licking, head shake | licking, head shake | head shake, chomping | licking |
| 13CPJ7 | head shake, pacing | licking, head shake | head shake | pacing | pacing | pacing |

— denotes no reaction recorded

TABLE 59

Observations following test article administration (days 52-54)

| Cat Id | Day 52 AM | Day 52 PM | Day 53 AM | Day 53 PM | Day 54 AM | Day 54 PM |
|---|---|---|---|---|---|---|
| 15EGA5 | licking | — | chomping | licking | head shake, licking | — |
| 13IRD3 | — | head shake | — | head shake | — | — |
| 15KGA2 | — | licking | head shake, chomping | licking | head shake, licking | head shake, licking |
| 13CNL3 | head shake | — | — | — | — | — |
| 13CCL1 | licking | — | gagging, chomping | — | head shake | gagging, head shake |
| GJY3 | licking | licking | — | — | — | — |
| 15KGC3 | head shake, licking | head shake | chomping | head shake, licking | chomping, head shake | head shake, licking |
| 13CPJ7 | head shaking, pacing | pacing | pacing | pacing | pacing | — |

— denotes no reaction recorded

TABLE 60

Observations following test article administration (days 55-57)

| Cat Id | Day 55 AM | Day 55 PM | Day 56 AM | Day 56 PM | Day 57 AM | Day 57 PM |
|---|---|---|---|---|---|---|
| 15EGA5 | chomping, drooling | licking | chomping, licking | licking | head shake, chomping, drooling | chomping, licking |
| 13IRD3 | head shake | — | — | head shake | — | — |
| 15KGA2 | chomping | — | chomping | head shake, licking | — | licking |
| 13CNL3 | — | — | — | — | — | — |
| 13CCL1 | gagging | gagging | — | head shake | — | gagging |
| GJY3 | — | licking | — | licking | licking | licking |
| 15KGC3 | head shake, chomping | head shake | head shake, chomping | head shake, chomping | licking | chomping, licking |
| 13CP17 | pacing | pacing | pacing | pacing | pacing | pacing |

— denotes no reaction recorded

TABLE 61

Observations following test article administration (days 58-60)

| | Day 58 | | Day 59 | | Day 60 | |
|---|---|---|---|---|---|---|
| Cat Id | AM | PM | AM | PM | AM | PM |
| 15EGA5 | licking | — | head shake | — | — | licking |
| 13IRD3 | — | — | — | licking | — | — |
| 15KGA2 | licking | — | licking | — | licking | licking |
| 13CNL3 | — | head shake | head shake | licking | head shake | head shake |
| 13CCL1 | gagging | licking | — | head shake, licking | licking | licking |
| GJY3 | licking | licking | licking | head shake | licking, head shake | licking |
| 15KGC3 | head shake, chomping | head shake, licking | head shake | violent head shake | licking | head shake |
| 13CPJ7 | pacing | pacing | pacing | pacing, licking | pacing, head shake | pacing |

— denotes no reaction recorded

TABLE 62

Observations following test article administration (days 61-63)

| | Day 61 | | Day 62 | | Day 63 | |
|---|---|---|---|---|---|---|
| Cat Id | AM | PM | AM | PM | AM | PM |
| 15EGA5 | — | — | licking | chomping, licking | head shake | licking |
| 13IRD3 | head shake | licking | head shake | licking | head shake | — |
| 15KGA2 | — | head shake | head shake, licking | licking, head shake | head shake, licking | head shake, licking |
| 13CNL3 | licking | — | — | — | — | head shake |
| 13CCL1 | gagging | head shake | — | gagging | gagging | gagging |
| GJY3 | — | — | licking | head shake | — | — |
| 15KGC3 | head shake, licking | head shake | chomping, licking | — | head shake, licking | head shake, licking |
| 13CPJ7 | pacing | uncooperative, pacing | pacing | pacing | pacing | pacing |

— denotes no reaction recorded

TABLE 63

Observations following test article administration (days 64-66)

| | Day 64 | | Day 65 | | Day 66 | |
|---|---|---|---|---|---|---|
| Cat Id | AM | PM | AM | PM | AM | PM |
| 15EGA5 | head shake, licking | licking | licking | licking, head shake | chomping | head shake, licking |
| 13IRD3 | head shake | — | licking | — | — | — |
| 15KGA2 | pacing, licking | pacing | head shake | head shake, licking | head shake | head shake, licking |
| 13CNL3 | — | — | licking | — | — | head shake, licking |
| 13CCL1 | head shake, licking | licking | — | gagging | licking | — |
| GJY3 | licking | licking, head shake | — | licking | licking | licking |
| 15KGC3 | head shake, licking | licking | head shake, licking | — | head shake, licking | head shake |
| 13CP17 | pacing | pacing | pacing | pacing | pacing, head shake | pacing |

— denotes no reaction recorded

TABLE 64

Observations following test article administration (days 67-69)

| | Day 67 | | Day 68 | | Day 69 | |
|---|---|---|---|---|---|---|
| Cat Id | AM | PM | AM | PM | AM | PM |
| 15EGA5 | — | licking | head shake, licking | licking | licking | head shake, licking |
| 13IRD3 | head shake | — | head shake | head shake | head shake | — |
| 15KGA2 | licking | — | head shake | licking | — | licking |
| 13CNL3 | head shake | — | — | — | licking | — |
| 13CCL1 | — | — | gagging | gagging | head shake, licking | head shake |
| GJY3 | licking | licking | — | licking, head shake | licking | licking |
| 15KGC3 | head shake | head shake, licking | head shake, chomping | head shake, licking | head shake | head shake |
| 13CPJ7 | pacing | pacing, licking | pacing | pacing | pacing | pacing |

— denotes no reaction recorded

TABLE 65

Observations following test article administration (days 70-72)

| | Day 79 | | Day 71 | | Day 72 | |
|---|---|---|---|---|---|---|
| Cat Id | AM | PM | AM | PM | AM | PM |
| 15EGA5 | licking | head shake | licking | head shake, licking | head shake, licking | licking |
| 13IRD3 | — | — | head shake | head shake | — | — |
| 15KGA2 | licking | — | chomping, licking | licking | head shake, licking | — |
| 13CNL3 | licking, head shake | head shake, licking | licking | licking | — | — |
| 13CCL1 | head shake | likcing | gagging | gagging | head shake | gagging, drooling |
| GJY3 | licking | licking | licking | licking, head shake | licking | head shake, licking |
| 15KGC3 | licking | head shake | head shake, licking | head shake, licking | head shake, licking | — |
| 13CPJ7 | pacing | pacing | pacing | pacing | pacing | pacing |

— denotes no reaction recorded

TABLE 66

Observations following test article administration (days 73-75)

| | Day 73 | | Day 74 | | Day 75 | |
|---|---|---|---|---|---|---|
| Cat Id | AM | PM | AM | PM | AM | PM |
| 15EGA5 | — | head shake | chomping, licking, head shake | licking | licking, head shake | head shake |
| 13IRD3 | — | — | head shake | head shake | head shake | — |
| 15KGA2 | — | licking | licking | — | head shake, pacing | head shake, licking |
| 13CNL3 | licking | head shake | — | — | head shake, licking | — |
| 13CCL1 | gagging | gagging, licking | head shake, licking | gagging, drooling | — | — |
| GJY3 | licking | licking | licking | — | licking | licking |
| 15KGC3 | licking, chewing | licking, head shake | head shake, licking | head shake, licking | chomping | head shake, licking |
| 13CPJ7 | pacing, head shake | pacing, head shake | pacing | pacing | pacing | pacing |

— denotes no reaction recorded

TABLE 67

Observations following test article administration (days 76-78)

| | Day 76 | | Day 77 | | Day 78 | |
|---|---|---|---|---|---|---|
| Cat Id | AM | PM | AM | PM | AM | PM |
| 15EGA5 | licking, chomping | head shake, licking | chomping, licking | — | head shake | licking |
| 13IRD3 | — | head shake | — | — | — | — |
| 15KGA2 | licking | head shake, licking | licking | head shake | — | licking |
| 13CNL3 | head shake | — | licking | head shake | head shake | licking, head shake |
| 13CCL1 | gagging, licking | gagging | head shake | gagging, head shake | gagging | licking |
| GJY3 | licking | licking | licking | licking | licking | — |
| 15KGC3 | head shake, licking | head shake, chomping | licking, head shake | licking | head shake, licking | licking |
| 13CPJ7 | head shake, pacing | pacing | head shake | pacing | pacing | head shake, pacing |

— denotes no reaction recorded

TABLE 68

Observations following test article administration (days 79-81)

| | Day 79 | | Day 80 | | Day 81 | |
|---|---|---|---|---|---|---|
| Cat Id | AM | PM | AM | PM | AM | PM |
| 15EGA5 | licking, head shake | licking | head shake, licking | — | head shake, licking | licking |
| 13IRD3 | head shake | head shake | — | head shake | licking | head shake, licking |
| 15KGA2 | licking | — | — | head shake, licking | licking | licking, head shake |
| 13CNL3 | head shake | licking | licking | licking | licking | — |
| 13CCL1 | licking | gagging, grimace | — | gagging | licking | drooling |
| GJY3 | licking | licking | head shake, licking | licking | licking | licking |
| 15KGC3 | head shake | head shake, licking | head shake, licking | head shake | head shake | head shake, licking |
| 13CPJ7 | pacing | head shake, pacing | pacing, licking | pacing, head shake | pacing, head shake | pacing |

— denotes no reaction recorded

TABLE 69

Observations following test article administration (days 82-84)

| Cat Id | Day 82 AM | Day 82 PM | Day 83 AM | Day 83 PM | Day 84 AM | Day 84 PM |
|---|---|---|---|---|---|---|
| 15EGA5 | licking, head shake | licking | licking | licking | licking | licking |
| 13IRD3 | — | head shake | head shake | — | — | — |
| 15KGA2 | head shake | licking | — | — | — | licking |
| 13CNL3 | licking | head shake | licking | head shake | head shake | head shake |
| 13CCL1 | gagging | head shake, licking | licking | licking, head shake | grimace, head shake | licking, grimace |
| GJY3 | licking | licking | licking, grimace | licking, head shake | licking | licking |
| 15KGC3 | licking, head shake | licking | head shake | licking | head shake, licking | head shake, licking |
| 13CPJ7 | pacing | licking | head shake | licking, pacing | head shake, pacing | head shake, licking |

— denotes no reaction recorded

Hematology and Serum Chemistry

Beginning in Week 2, there was an increase in the mean alanine aminotransferase (ALT) value for the group. This value remained increased from baseline until the end of the study. Mild increases in individual ALT levels were observed in the majority of the cats throughout the study. The cat with the greatest increase in ALT (above the normal reference range of 100 U/L), with a concurrent increase in aspartate aminotransferase (AST), was 13CNL3. Beginning in Week 4, this cat's ALT and AST levels began to decrease, but remained elevated from baseline. ALT levels remained above the normal reference range, shown in Table 70, for the duration of the study. Also, during Week 2, the ALT levels of cats 13IRD3 and 13CPJ7 increased by 23 to 31 U/L, respectively, from baseline values. The ALT levels of cat 13CPJ7 returned to baseline by Week 10. At Week 4, the ALT of cat 13CCL1 was elevated from baseline by 32 U/L. Levels returned to baseline by Week 10. The test article appeared to cause mild ALT changes in the majority of cats with one cat maintaining elevated ALT levels above normal limits throughout the study. The group mean values of all other blood parameters remained within normal limits and no apparent trends were noted. Hematology and serum chemistry results are presented in Tables 71-74.

TABLE 70

Hematology and serum chemistry normal reference ranges

| Parameter | Normal Reference Ranges |
|---|---|
| Total Protein (g/dL): | 5.2-8.8 g/dL |
| Albumin (g/dL): | 2.5-3.9 g/dL |
| Globulin (g/dL): | 2.3-5.3 g/dL |
| A/G Ratio: | 0.4-1.5 Ratio |
| AST (IU/L): | 10-100 IU/L |
| ALT (IU/L): | 10-100 IU/L |
| Alkaline Phosphatase (IU/L): | 6-102 IU/L |
| GGTP (IU/L): | 1-10 IU/L |
| Total Bilirubin (mg/dL): | 0.1-0.4 mg/dL |
| Urea Nitrogen (mg/dL): | 14-36 mg/dL |
| Creatinine (mg/dL): | 0.6-2.4 mg/dL |
| BUN/Creatinine Ratio: | 4-33 Ratio |
| Phosphorus (mg/dL): | 2.4-8.2 mg/dL |
| Glucose (mg/dL): | 64-170 mg/dL |
| Calcium (mg/dL): | 8.2-10.8 mg/dL |
| Magnesium (mEq/L): | 1.5-2.5 mEq/L |
| Sodium (mEq/L): | 145-158 mEq/L |
| Potassium (mEq/L): | 3.4-5.6 mEq/L |
| Chloride (mEq/L): | 104-128 mEq/L |
| Cholesterol (mg/dL): | 75-220 mg/dL |
| Triglycerides (mg/dL): | 25-160 mg/dL |
| CPK (U/L): | 56-529 U/L |
| WBC ($10^3/\mu L$): | 3.5-16.0 $10^3/\mu L$ |
| RBC ($10^6/\mu L$): | 4.8-9.3 $10^6/\mu L$ |
| Hemoglobin (g/dL): | 9.3-15.9 g/dL |
| Hematocrit (%): | 29-48% |
| MCV (fL): | 37-61 fL |
| MCH (pg): | 11-21 pg |
| MCHC (g/dL): | 30-38 g/dL |
| Platelets ($10^3/\mu L$): | 200-500 $10^3/\mu L$ |
| Absolute Polys (µL): | 2500-8500 µL |
| Absolute Bands (µL): | 0 µL |
| Absolute Lymphs (µL): | 1200-8000 µL |
| Absolute Monos (µL): | 0-600 µL |
| Absolute Eos (µL): | 0-1000 µL |
| Absolute Basos (µL): | 0-150 µL |

TABLE 71

Summary of hematology and serum chemistry results - Part 1

| | Total Protein (g/dL) | Albumin (g/dL) | Globulin (g/dL) | A/G Ratio | AST (U/L) | ALT (U/L) | Alkaline Phospahte (U/L) | GGTP (U/L) | Total Bilirubin (mg/dL) | Urea Nitrogen (mg/dL) | Creatinine (mg/dL) |
|---|---|---|---|---|---|---|---|---|---|---|---|
| | Initial Results | | | | | | | | | | |
| Mean: | 7.2 | 3.2 | 4.0 | 0.8 | 21 | 51 | 30 | 2 | 0.1 | 25 | 1.3 |
| SD: | 0.46 | 0.27 | 0.60 | 0.18 | 4.8 | 15.2 | 15.4 | 0.8 | 0.00 | 2.6 | 0.19 |
| N: | 8 | 8 | 8 | 8 | 8 | 8 | 8 | 8 | 8 | 8 | 8 |
| | Week 2 | | | | | | | | | | |
| Mean: | 7.1 | 3.2 | 3.9 | 0.9 | 27 | 104 | 33 | 2 | 0.1 | 23 | 1.1 |
| SD: | 0.51 | 0.30 | 0.70 | 0.20 | 19.5 | 117.7 | 16.7 | 1.0 | 0.04 | 3.1 | 0.18 |
| N: | 8 | 8 | 8 | 8 | 8 | 8 | 8 | 8 | 8 | 8 | 8 |

TABLE 71-continued

Summary of hematology and serum chemistry results - Part 1

| | Total Protein (g/dL) | Albumin (g/dL) | Globulin (g/dL) | A/G Ratio | AST (U/L) | ALT (U/L) | Alkaline Phospahte (U/L) | GGTP (U/L) | Total Bilirubin (mg/dL) | Urea Nitrogen (mg/dL) | Creatinine (mg/dL) |
|---|---|---|---|---|---|---|---|---|---|---|---|
| | | | | | | Week 4 | | | | | |
| Mean: | 6.7 | 3.2 | 3.5 | 0.9 | 24 | 90 | 30 | 1 | 0.1 | 22 | 1.2 |
| SD: | 0.48 | 0.30 | 0.67 | 0.21 | 11.6 | 85.2 | 16.1 | 0.0 | 0.00 | 2.9 | 0.13 |
| N: | 8 | 8 | 8 | 8 | 8 | 8 | 8 | 8 | 8 | 8 | 8 |
| | | | | | | Week 6 | | | | | |
| Mean: | 6.5 | 3.3 | 3.2 | 1.1 | 25 | 80 | 32 | 1 | 0.1 | 20 | 1.1 |
| SD: | 0.41 | 0.31 | 0.63 | 0.26 | 13.1 | 48.1 | 17.0 | 0.4 | 0.04 | 3.5 | 0.11 |
| N: | 8 | 8 | 8 | 8 | 8 | 8 | 8 | 8 | 8 | 8 | 8 |
| | | | | | | Week 8 | | | | | |
| Mean: | 7.1 | 3.4 | 3.8 | 0.9 | 25 | 76 | 29 | 2 | 0.2 | 20 | 1.3 |
| SD: | 0.49 | 0.36 | 0.63 | 0.19 | 10.8 | 46.8 | 15.3 | 0.9 | 0.00 | 2.4 | 0.16 |
| N: | 8 | 8 | 8 | 8 | 8 | 8 | 8 | 8 | 8 | 8 | 8 |
| | | | | | | Week 10 | | | | | |
| Mean: | 7.0 | 3.3 | 3.8 | 0.9 | 24 | 67 | 30 | 1 | 0.1 | 23 | 1.3 |
| SD: | 0.48 | 0.31 | 0.61 | 0.20 | 7.7 | 30.2 | 17.6 | 0.4 | 0.00 | 2.7 | 0.11 |
| N: | 8 | 8 | 8 | 8 | 8 | 8 | 8 | 8 | 8 | 8 | 8 |
| | | | | | | Final Results | | | | | |
| Mean: | 7.0 | 3.2 | 3.9 | 0.9 | 24 | 75 | 28 | 1 | 0.1 | 19 | 1.3 |
| SD: | 0.55 | 0.31 | 0.73 | 0.20 | 9.4 | 42.2 | 15.9 | 0.4 | 0.00 | 1.6 | 0.20 |
| N: | 8 | 8 | 8 | 8 | 8 | 8 | 8 | 8 | 8 | 8 | 8 |

TABLE 72

Summary of hematology and serum chemistry results - Part 2

| | BUN/Creatinine Ratio | Phosphorus (mg/dL) | Glucose (mg/dL) | Calcium (mg/dL) | Magnesium (mEq/L) | Sodium (mEq/L) | Potassium (mEq/L) | Chloride (mEq/L) | Cholesterol (mg/dL) | Triglycerides (mg/dL) |
|---|---|---|---|---|---|---|---|---|---|---|
| | | | | | Initial Results | | | | | |
| Mean: | 18 | 4.5 | 90 | 9.6 | 1.9 | 151 | 4.7 | 119 | 139 | 32 |
| SD: | 3.3 | 1.08 | 7.2 | 0.41 | 0.16 | 2.3 | 0.60 | 2.8 | 24.7 | 4.4 |
| N: | 8 | 8 | 8 | 8 | 8 | 8 | 8 | 8 | 8 | 8 |
| | | | | | Week 2 | | | | | |
| Mean: | 22 | 4.9 | 84 | 9.4 | 2.0 | 153 | 5.2 | 122 | 126 | 37 |
| SD: | 2.5 | 1.10 | 11.0 | 0.31 | 0.12 | 1.6 | 0.48 | 1.9 | 13.5 | 12.5 |
| N: | 8 | 8 | 8 | 8 | 8 | 8 | 8 | 8 | 8 | 8 |
| | | | | | Week 4 | | | | | |
| Mean: | 19 | 4.6 | 8.5 | 9.0 | 1.8 | 153 | 4.7 | 121 | 123 | 28 |
| SD: | 2.7 | 0.97 | 6.9 | 0.37 | 0.10 | 1.6 | 0.41 | 1.8 | 17.6 | 5.0 |
| N: | 8 | 8 | 8 | 8 | 8 | 8 | 8 | 8 | 8 | 8 |
| | | | | | Week 6 | | | | | |
| Mean: | 18 | 4.8 | 79 | 9.3 | 1.9 | 153 | 5.2 | 121 | 125 | 29 |
| SD: | 2.4 | 0.96 | 5.4 | 0.35 | 0.12 | 1.5 | 0.28 | 1.3 | 17.1 | 7.3 |
| N: | 8 | 8 | 8 | 8 | 8 | 8 | 8 | 8 | 8 | 8 |
| | | | | | Week 8 | | | | | |
| Mean: | 16 | 4.3 | 87 | 9.5 | 1.8 | 154 | 4.7 | 122 | 128 | 26 |
| SD: | 1.4 | 0.92 | 8.3 | 0.42 | 0.11 | 3.4 | 0.77 | 2.4 | 15.6 | 4.2 |
| N: | 8 | 8 | 8 | 8 | 8 | 8 | 8 | 8 | 8 | 8 |
| | | | | | Week 10 | | | | | |
| Mean: | 17 | 4.1 | 85 | 9.2 | 1.8 | 152 | 4.5 | 120 | 123 | 22 |
| SD: | 1.5 | 0.90 | 0.4 | 0.39 | 0.10 | 1.7 | 0.43 | 1.6 | 19.5 | 3.9 |
| N: | 8 | 8 | 8 | 8 | 8 | 8 | 8 | 8 | 8 | 8 |
| | | | | | Final Results | | | | | |
| Mean: | 15 | 4.1 | 86 | 9.3 | 1.8 | 152 | 4.5 | 120 | 123 | 25 |
| SD: | 2.0 | 0.68 | 10.2 | 0.31 | 0.13 | 1.5 | 0.30 | 1.5 | 19.4 | 4.5 |
| N: | 8 | 8 | 8 | 8 | 8 | 8 | 8 | 8 | 8 | 8 |

TABLE 73

Summary of hematology and serum chemistry results - Part 3

| | CPK (U/L) | WBC (10^3/mm 3) | RBC (10^6/mm 3) | Hemoglobin (g/dL) | Hematocrit (%) | MCV (um^3) | MCH (uug) | MCHC (g/dl) | Platelets (10^3/mm 3) |
|---|---|---|---|---|---|---|---|---|---|
| | | | | Initial Results | | | | | |
| Mean: | 197 | 14.0 | 8.8 | 11.4 | 39 | 44 | 13.0 | 30 | 308 |
| SD: | 89.3 | 4.45 | 0.73 | 1.09 | 4.1 | 2.5 | 0.35 | 2.1 | 138.2 |
| N: | 8 | 8 | 8 | 8 | 8 | 8 | 8 | 8 | 8 |
| | | | | Week 2 | | | | | |
| Mean: | 153 | 12.1 | 8.3 | 11.1 | 36 | 44 | 13.4 | 31 | 375 |
| SD: | 88.2 | 3.91 | 0.77 | 0.95 | 3.0 | 3.1 | 0.42 | 1.6 | 106.2 |
| N: | 8 | 8 | 8 | 8 | 8 | 8 | 8 | 8 | 8 |
| | | | | Week 4 | | | | | |
| Mean: | 114 | 13.6 | 8.0 | 10.7 | 34 | 42 | 13.4 | 32 | 374 |
| SD: | 40.7 | 4.10 | 0.96 | 1.31 | 3.9 | 1.0 | 0.32 | 0.5 | 84.8 |
| N: | 8 | 8 | 8 | 8 | 8 | 8 | 8 | 8 | 8 |
| | | | | Week 6 | | | | | |
| Mean: | 135 | 12.3 | 8.8 | 11.7 | 39 | 44 | 13.3 | 30 | 362 |
| SD: | 66.2 | 4.14 | 0.79 | 0.97 | 3.4 | 1.8 | 0.80 | 1.4 | 99.6 |
| N: | 8 | 8 | 8 | 8 | 8 | 8 | 8 | 8 | 8 |
| | | | | Week 8 | | | | | |
| Mean: | 106 | 12.9 | 9.0 | 12.4 | 40 | 44 | 13.7 | 31 | 361 |
| SD: | 32.4 | 375 | 0.73 | 1.06 | 3.7 | 1.7 | 0.46 | 1.0 | 57.9 |
| N: | 8 | 8 | 8 | 8 | 8 | 8 | 8 | 8 | 8 |
| | | | | Week 10 | | | | | |
| Mean: | 137 | 10.9 | 8.8 | 11.6 | 40 | 45 | 13.3 | 29 | 329 |
| SD: | 76.9 | 3.82 | 0.89 | 1.45 | 4.5 | 1.9 | 0.43 | 1.2 | 63.7 |
| N: | 8 | 8 | 8 | 8 | 8 | 8 | 8 | 8 | 8 |
| | | | | Final Results | | | | | |
| Mean: | 126 | 12.5 | 9.0 | 11.8 | 39 | 43 | 13.3 | 31 | 289 |
| SD: | 40.0 | 4.56 | 1.11 | 1.46 | 5.6 | 2.6 | 0.64 | 1.4 | 54.5 |
| N: | 8 | 8 | 8 | 8 | 8 | 8 | 8 | 8 | 8 |

TABLE 74

Summary of hematology and serum chemistry results - Part 4

| | Abs Polys | % Polys | Abs Bands | % Bands | Abs Lymphs | % Lymphs | Abs Monos | % Monos | Abs Eos | % Eos | Abs Basos | % Basos |
|---|---|---|---|---|---|---|---|---|---|---|---|---|
| | | | | | | Initial Results | | | | | | |
| Mean: | 7980 | 56 | 0 | 0 | 4481 | 32 | 428 | 3 | 1149 | 9 | 0 | 0 |
| SD: | 3059.8 | 9.0 | 0.0 | 0.0 | 1466.5 | 7.0 | 138.0 | 1.0 | 417.8 | 3.4 | 0.0 | 0.0 |
| N: | 8 | 8 | 8 | 8 | 8 | 8 | 8 | 8 | 8 | 8 | 8 | 8 |
| | | | | | | Week 2 | | | | | | |
| Mean: | 7762 | 64 | 0 | 0 | 2988 | 26 | 495 | 4 | 817 | 7 | 0 | 0 |
| SD: | 2917.9 | 7.0 | 0.0 | 0.0 | 902.2 | 7.0 | 255.7 | 1.4 | 392.0 | 2.1 | 0.0 | 0.0 |
| N: | 8 | 8 | 8 | 8 | 8 | 8 | 8 | 8 | 8 | 8 | 8 | 8 |
| | | | | | | Week 4 | | | | | | |
| Mean: | 8993 | 65 | 0 | 0 | 3315 | 25 | 417 | 3 | 876 | 7 | 0 | 0 |
| SD: | 3181.7 | 4.0 | 0.0 | 0.0 | 781.7 | 5.3 | 187.0 | 0.8 | 395.3 | 2.7 | 0.0 | 0.0 |
| N: | 8 | 8 | 8 | 8 | 8 | 8 | 8 | 8 | 8 | 8 | 8 | 8 |
| | | | | | | Week 6 | | | | | | |
| Mean: | 7032 | 57 | 0 | 0 | 4264 | 35 | 440 | 3 | 539 | 5 | 0 | 0 |
| SD: | 2704.4 | 7.4 | 0.0 | 0.0 | 1366.9 | 3.6 | 296.7 | 1.2 | 539.6 | 5.1 | 0.0 | 0.0 |
| N | 8 | 8 | 8 | 8 | 8 | 8 | 8 | 8 | 8 | 8 | 8 | 8 |

TABLE 74-continued

Summary of hematology and serum chemistry results - Part 4

|  | Abs Polys | % Polys | Abs Bands | % Bands | Abs Lymphs | % Lymphs | Abs Monos | % Monos | Abs Eos | % Eos | Abs Basos | % Basos |
|---|---|---|---|---|---|---|---|---|---|---|---|---|
| Week 8 | | | | | | | | | | | | |
| Mean: | 7394 | 56 | 0 | 0 | 3856 | 31 | 545 | 4 | 1026 | 8 | 30 | 0 |
| SD: | 3061.4 | 7.0 | 0.0 | 0.0 | 802.9 | 8.3 | 388.9 | 2.1 | 601.2 | 3.2 | 54.9 | 0.5 |
| N: | 8 | 8 | 8 | 8 | 8 | 8 | 8 | 8 | 8 | 8 | 8 | 8 |
| Week 10 | | | | | | | | | | | | |
| Mean: | 6159 | 57 | 0 | 0 | 3732 | 34 | 355 | 4 | 603 | 5 | 0 | 0 |
| SD: | 2300.3 | 7.2 | 0.0 | 0.0 | 1464.7 | 8.1 | 108.3 | 1.1 | 451.0 | 2.2 | 0.0 | 0.0 |
| N: | 8 | 8 | 8 | 8 | 8 | 8 | 8 | 8 | 8 | 8 | 8 | 8 |
| Final Results | | | | | | | | | | | | |
| Mean: | 7847 | 61 | 0 | 0 | 3614 | 31 | 364 | 3 | 650 | 6 | 0 | 0 |
| SD: | 3819.8 | 9.8 | 0.0 | 0.0 | 1051.7 | 9.3 | 207.7 | 0.7 | 258.2 | 2.9 | 0.0 | 0.0 |
| N: | 8 | 8 | 8 | 8 | 8 | 8 | 8 | 8 | 8 | 8 | 8 | 8 |

Clinical Observations

During the study, occasional instances of loose stool and emesis were recorded, as shown in Table 75. Cat ID #13CCL1 was observed having five instances of food emesis. Cat ID #13CNL3 was observed having one instance of hairball emesis and one instance of hair and bile emesis. Cat ID #131RD3 was observed having one instance of food emesis. Cat ID #15EGA5 was observed having three instances of food vomit and one instance of hair and bile emesis. Cat ID #GJY3 was observed having two instances of hairball emesis and one instance of food emesis. Occasional episodes of hairball and food emesis are not unusual in the cat colony and were not considered to be related to the test article.

TABLE 75

Clinical observations

| Cat Id | Date | Observation |
|---|---|---|
| 13CCL1 | Jan. 19, 2018 | Very calm, relaxed prior to dosing in am and pm |
| 13CCL1 | Jan. 21, 2018 | Very calm, relaxed prior to dosing in pm |
| 13CCL1 | Jan. 25, 2018 | Food vomit |
| 13CCL1 | Jan. 31, 2018 | Food vomit |
| 13CCL1 | Feb. 9, 2018 | Food vomit |
| 13CCL1 | Mar. 2, 2018 | Food vomit |
| 13CCL1 | Apr. 8, 2018 | Food vomit |
| 13CNL3 | Jan. 19, 2018 | Very calm, relaxed prior to dosing in pm |
| 13CNL3 | Jan. 21, 2018 | Very calm, relaxed prior to dosing in pm |
| 13CNL3 | Jan. 22, 2018 | Very relaxed |
| 13CNL3 | Feb. 4, 2018 | Hairball vomit |
| 13CNL3 | Mar. 6, 2018 | Bile vomit and hairball vomit |
| 13IRD3 | Feb. 8, 2018 | Semi digested food vomit |
| 15EGA5 | Jan. 26, 2018 | Food vomit |
| 15EGA5 | Feb. 8, 2018 | Semi digested food vomit |
| 15EGA5 | Mar. 9, 2018 | Bile vomit and hairball vomit |
| 15EGA5 | Mar. 19, 2018 | Digested food vomit |
| 15KGA2 | Jan. 19, 2018 | Very calm, relaxed prior to dosing in am and pm |
| 15KGA2 | Jan. 21, 2018 | Very calm, relaxed prior to dosing in am and pm |
| 15KGA2 | Jan. 22, 2018 | Very relaxed |
| GJY3 | Jan. 31, 2018 | Hairball vomit |
| GJY3 | Feb. 18, 2018 | Digested food vomit |
| GJY3 | Mar. 19, 2018 | Hairball vomit |

PK Data

Table 76 shows the quantification of cannabidiol in feline serum and Table 77 shows cat cannabadiol pharmacokinetics.

TABLE 76

Cannabidiol quantification in feline serum.

| PMF No. | Animal ID | Species | Time Point | Replicate (A or B) | ppb in Serum |
|---|---|---|---|---|---|
| 53 | 13CCL1 | Feline | 1 day prior | A | ND |
| 53 | | | 1 day prior | B | ND |

TABLE 76-continued

Cannabidiol quantification in feline serum.

| PMF No. | Animal ID | Species | Time Point | Replicate (A or B) | ppb in Serum |
|---|---|---|---|---|---|
| 59 | | | 60 min | B | 32.85 |
| 59 | | | 60 min | A | 34.26 |
| 65 | | | 4 hr | B | 1.69** |
| 65 | | | 4 hr | A | 1.82** |
| 71 | | | 8 hr | B | 65.42 |
| 71 | | | 8 hr | A | 79.30 |
| 77 | | | 24 hr | B | 42.76 |
| 77 | | | 24 hr | A | 44.88 |
| 52 | 13CNL3 | Feline | 1 day prior | A | ND |
| 52 | | | 1 day prior | B | ND |
| 58 | | | 60 min | B | 24.44 |
| 58 | | | 60 min | A | 26.32 |
| 64 | | | 4 hr | A | ND |
| 64 | | | 4 hr | B | ND |
| 70 | | | 8 hr | B | 1.82** |
| 70 | | | 8 hr | A | 2.22* |
| 76 | | | 24 hr | A | 141.92 |
| 76 | | | 24 hr | B | 147.74 |
| 50 | 13IRD3 | Feline | 1 day prior | A | ND |
| 50 | | | 1 day prior | B | ND |
| 56 | | | 60 min | B | 44.14 |
| 56 | | | 60 min | A | 45.40 |
| 62 | | | 4 hr | B | 1.53** |
| 62 | | | 4 hr | A | ND |
| 68 | | | 8 hr | A | ND |
| 68 | | | 8 hr | B | ND |
| 74 | | | 24 hr | A | 10.28 |
| 74 | | | 24 hr | B | 10.31 |
| 49 | 15EGA5 | Feline | 1 day prior | A | ND |
| 49 | | | 1 day prior | B | ND |
| 55 | | | 60 min | B | 28.10 |
| 55 | | | 60 min | A | 31.02 |
| 61 | | | 4 hr | A | ND |
| 61 | | | 4 hr | B | ND |
| 67 | | | 8 hr | A | 44.23 |
| 67 | | | 8 hr | B | 46.05 |
| 73 | | | 24 hr | A | 13.95 |
| 73 | | | 24 hr | B | 17.17 |
| 51 | 15KGA2 | Feline | 1 day prior | A | ND |
| 51 | | | 1 day prior | B | ND |
| 57 | | | 60 min | A | ND |
| 57 | | | 60 min | B | ND |
| 63 | | | 4 hr | A | ND |
| 63 | | | 4 hr | B | ND |
| 69 | | | 8 hr | B | 365.18 |
| 69 | | | 8 hr | A | 376.28 |
| 75 | | | 24 hr | B | 0.18** |
| 75 | | | 24 hr | A | 0.36** |
| 54 | GJY3 | Feline | 1 day prior | A | ND |
| 54 | | | 1 day prior | B | ND |
| 60 | | | 60 min | A | 378.59 |
| 60 | | | 60 min | B | 535.08 |
| 66 | | | 4 hr | A | 51.48 |
| 66 | | | 4 hr | B | 68.31 |
| 72 | | | 8 hr | A | 71.64 |
| 72 | | | 8 hr | B | 79.59 |
| 78 | | | 24 hr | B | 33.12 |
| 78 | | | 24 hr | A | 35.88 |

Cannabidiol quantification in Feline Serum is reported as ng/mL (ppb).
ND = Not Detected (no quantifiable value).
*= values below calculated Limit of Quantification (6.2 ppb).
**= values below calculated Limit of Detection (1.9 ppb).

TABLE 77

Cat cannabadiol pharmacokinetics

| Cat # | Cmax | Tmax | T½ el | AUC 0 -> t | MRT |
|---|---|---|---|---|---|
| 15EGA5 | 75.3 | 1 | 1.2 | 212.2 | 2.1 |
| 13IRD3 | 40.5 | 1 | 1.3 | 125.0 | 2.4 |
| 15KGA2 | 53.3 | 1 | 1.7 | 194.1 | 2.9 |
| 13CNL3 | 21.2 | 4 | 1.7 | 134.2 | 5.4 |
| 13CCL1 | 20.4 | 1 | 1.7 | 60.2 | 2.7 |
| GJY3 | 47.6 | 4 | 1.2 | 265.0 | 5.7 |
| 15KGC3 | 8.8 | 1 | 2.3 | 54.2 | 3.8 |
| 13CPJ7 | 12.1 | 1 | 2.3 | 42.4 | 2.4 |

Oral administration of 2/mg/kg cannabidiol in capsule form
Cmax = Maximum concentration (ng/ml)
Tmax = Time of maximum concentration (hr)
T½ el = Half-life of elimination (hr)
AUC 0-t = Area under the curve (0 time to time of last collection [24 hr]) (ng-hr/ml)
MRT = Mean residence time (hr)

The LOD for CBD in feline serum was calculated to be 1.9 ng/mL (ppb in serum). The LOQ for CBD in feline serum was calculated to be 6.2 ng/mL (ppb in serum).

Conclusions

There were no adverse effects on body weights or food consumption. Group mean alanine aminotransferase values exhibited elevations during the study that peaked at Week 2. Levels decreased during the following weeks, but did not return to baseline levels. ALT levels of one cat (13CNL3) remained significantly elevated throughout the study, exceeding normal reference ranges for the duration of the treatment period. The remaining group mean hematology and serum chemistry values remained within normal reference limits throughout the study and apparent trends were not observed over time. No adverse clinical observations that were considered to be related to the administration of the test article were observed for any of the cats during the course of the study. However, acceptance of the test article was considered to be poor.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A pharmaceutical composition comprising hemp extract and a carrier, wherein the hemp extract comprises:
    cannabidiol;
    cannabidiolic acid;
    cannabigerolic acid; and
    D9-tetrahydrocannabinol,
wherein the cannabidiol and the cannabidiolic acid are present in the pharmaceutical composition at a first ratio, and the D9-tetrahydrocannabinol and total cannabinoids are present in the pharmaceutical composition at a second ratio, wherein the first ratio is from about 0.6:1 to about 1:0.6, and wherein the second ratio is from about 1:50 to about 1:20.

2. The pharmaceutical composition of claim 1, wherein the hemp extract further comprises cannabichromene.

3. The pharmaceutical composition of claim 1, wherein the hemp extract further comprises four or more of the following:
α-pinene;
β-myrcene;
β-pinene;
δ-limonene;
linalool
β-caryophyllene;
α-humulene;
nerolidol 2;
guaiol;
caryophyllene oxide; and
α-bisabolol.

4. The pharmaceutical composition of claim 1, wherein the concentration of D9-tetrahydrocannabinol is less than about 2 mg/mL.

5. The pharmaceutical composition of claim 1, wherein the concentration of D9-tetrahydrocannabinol is less than about 1.5 mg/mL.

6. The pharmaceutical composition of claim 1, wherein the concentration of D9-tetrahydrocannabinol is less than about 1.0 mg/mL.

7. The pharmaceutical composition of claim 3, wherein the hemp extract further comprises one or more of:
camphene;
β-ocimene;
eucalyptol;
isopulegol; and/or
nerolidol 1.

8. A pharmaceutical composition for oral delivery comprising hemp extract and a carrier, wherein the hemp extract comprises:
cannabidiol;
cannabidiolic acid; and
D9-tetrahydrocannabinol,
wherein the cannabidiol and the cannabidiolic acid are present in the pharmaceutical composition at a first ratio, and the D9-tetrahydrocannabinol and total cannabinoids are present in the pharmaceutical composition at a second ratio, wherein the first ratio is from about 0.6:1 to about 1:0.6, wherein the second ratio is from about 1:50 to about 1:20, and wherein the carrier is selected from the group consisting of linseed oil, olive oil, fish oil, salmon oil, coconut oil, catnip oil, sesame oil, and grapeseed oil.

9. The pharmaceutical composition of claim 8, wherein the hemp extract further comprises cannabigerolic acid and cannabichromene.

10. The pharmaceutical composition of claim 8, wherein the hemp extract further comprises four or more of the following:
α-pinene;
β-myrcene;
β-pinene;
δ-limonene;
linalool;
β-caryophyllene;
α-humulene;
nerolidol 2;
guaiol;
caryophyllene oxide; and
α-bisabolol.

11. The pharmaceutical composition of claim 8, wherein the concentration of D9-tetrahydrocannabinol is less than about 2 mg/mL.

12. The pharmaceutical composition of claim 8, wherein the concentration of D9-tetrahydrocannabinol is less than about 1.5 mg/mL.

13. The pharmaceutical composition of claim 8, wherein the concentration of D9-tetrahydrocannabinol is less than about 1.0 mg/mL.

14. The pharmaceutical composition of claim 10, wherein the hemp extract further comprises one or more of:
camphene;
β-ocimene;
eucalyptol;
isopulegol; and/or
nerolidol 1.

15. The pharmaceutical composition of claim 8, wherein the carrier is grapeseed oil.

16. The pharmaceutical composition of claim 8, wherein the carrier is catnip oil.

17. A pharmaceutical composition formulated as a chew comprising hemp extract and a carrier, wherein the hemp extract comprises:
cannabidiol;
cannabidiolic acid; and
D9-tetrahydrocannabinol,
wherein the cannabidiol and the cannabidiolic acid are present in the pharmaceutical composition at a first ratio, and the D9-tetrahydrocannabinol and total cannabinoids are present in the pharmaceutical composition at a second ratio, wherein the first is from about 0.6:1 to about 1:0.6, and wherein the second ratio is from about 1:50 to about 1:20.

18. The pharmaceutical composition of claim 17, wherein the hemp extract further comprises cannabigerolic acid and cannabichromene.

19. The pharmaceutical composition of claim 17, wherein the hemp extract further comprises four or more of the following:
α-pinene;
β-myrcene;
β-pinene;
δ-limonene;
linalool;
β-caryophyllene;
α-humulene;
nerolidol 2;
guaiol;
caryophyllene oxide; and
α-bisabolol.

20. The pharmaceutical composition of claim 17, wherein the concentration of D9-tetrahydrocannabinol is less than about 2 mg/mL.

21. The pharmaceutical composition of claim 17, wherein the concentration of D9-tetrahydrocannabinol is less than about 1.5 mg/mL.

22. The pharmaceutical composition of claim 17, wherein the concentration of D9-tetrahydrocannabinol is less than about 1.0 mg/mL.

23. The pharmaceutical composition of claim 17, wherein the hemp extract further comprises one or more of:
camphene;
β-ocimene;
eucalyptol;
isopulegol; and/or
nerolidol 1.

24. The pharmaceutical composition of claim 17, wherein the weight of the chew is about 0.5-10 g.

* * * * *